US00RE51126E

(19) United States
(12) Reissued Patent
Pomper et al.

(10) Patent Number: US RE51,126 E
(45) Date of Reissued Patent: Nov. 17, 2026

(54) PSMA-BINDING AGENTS AND USES THEREOF

(71) Applicant: The Johns Hopkins University, Baltimore, MD (US)

(72) Inventors: Martin Gilbert Pomper, Baltimore, MD (US); Ronnie Charles Mease, Fairfax, VA (US); Ying Chen, Timmonium, MD (US)

(73) Assignee: The Johns Hopkins University, Baltimore, MD (US)

(21) Appl. No.: 19/414,120

(22) Filed: Dec. 9, 2025

Related U.S. Patent Documents

Reissue of:
(64) Patent No.: 8,778,305
Issued: Jul. 15, 2014
Appl. No.: 13/057,044
PCT Filed: Jul. 31, 2009
PCT No.: PCT/US2009/052456
§ 371 (c)(1),
(2) Date: Feb. 1, 2011
PCT Pub. No.: WO2010/014933
PCT Pub. Date: Feb. 4, 2010

U.S. Applications:
(60) Provisional application No. 61/111,791, filed on Nov. 6, 2008, provisional application No. 61/085,462, filed on Aug. 1, 2008.

(51) Int. Cl.

| | |
|---|---|
| ***A61K 51/04*** | (2006.01) |
| ***A61K 9/127*** | (2025.01) |
| ***C07C 275/16*** | (2006.01) |
| ***C07C 275/18*** | (2006.01) |
| ***C07D 213/61*** | (2006.01) |
| ***C07D 213/74*** | (2006.01) |
| ***C07D 213/82*** | (2006.01) |
| ***C07F 7/22*** | (2006.01) |

(52) U.S. Cl.
CPC ..... *A61K 51/0455* (2013.01); *A61K 9/127* (2013.01); *A61K 51/0402* (2013.01); *C07C 275/16* (2013.01); *C07C 275/18* (2013.01); *C07D 213/61* (2013.01); *C07D 213/74* (2013.01); *C07D 213/82* (2013.01); *C07F 7/2208* (2013.01); *C07B 2200/05* (2013.01); *Y02P 20/55* (2015.11)

(58) Field of Classification Search
CPC ..... A61K 51/0455; A61K 9/127; A61K 51/0402; C07C 275/16; C07C 275/18; C07D 213/61; C07D 213/74; C07D 213/82; C07F 7/2208; C07B 2200/05; Y02P 20/55
See application file for complete search history.

(56) References Cited

U.S. PATENT DOCUMENTS

| | | | | |
|---|---|---|---|---|
| 6,487,129 | B2 | 11/2002 | Hirata | |
| 8,487,129 | B2 | 7/2013 | Babich et al. | |
| 8,778,305 | B2 | 7/2014 | Pomper et al. | |
| 9,226,981 | B2 | 1/2016 | Pomper et al. | |
| 9,309,193 | B2 | 4/2016 | Babich et al. | |
| 9,861,713 | B2 | 1/2018 | Pomper et al. | |
| 9,878,980 | B2 | 1/2018 | Babich et al. | |
| 10,131,627 | B2 | 11/2018 | Babich et al. | |
| 10,500,292 | B2 | 12/2019 | Pomper et al. | |
| 10,640,461 | B2 | 5/2020 | Babich et al. | |
| 10,647,666 | B2 | 5/2020 | Babich et al. | |
| 10,947,197 | B2 | 3/2021 | Ravert et al. | |
| 12,070,513 | B2 | 8/2024 | Pomper et al. | |
| 12,534,429 | B2 | 1/2026 | Babich et al. | |
| 2004/0054190 | A1 | 3/2004 | Pomper et al. | |
| 2008/0193381 | A1* | 8/2008 | Babich et al. | 424/9.1 |
| 2008/0311037 | A1* | 12/2008 | Heston et al. | 424/1.85 |
| 2017/0044098 | A1 | 2/2017 | Babich et al. | |
| 2025/0177578 | A1 | 6/2025 | Pomper | |

FOREIGN PATENT DOCUMENTS

| | | | |
|---|---|---|---|
| RU | 2233269 | C2 | 7/2004 |
| WO | WO-2000064911 | A1 | 11/2000 |
| WO | WO-2002022627 | A2 | 3/2002 |
| WO | WO-2003060523 | A1 | 7/2003 |
| WO | WO-2006093991 | A1 | 9/2006 |
| WO | WO-2008/058192 | A2 | 5/2008 |

(Continued)

OTHER PUBLICATIONS

Bakker W.H., et al., "In Vivo Use of a Radioiodinated Somatostatin Analogue: Dynamics, Metabolism, and Binding to Somatostatin Receptor-positive Tumors in Man," The Journal of Nuclear Medicine, Jun. 1991, vol. 32, No. 6, pp. 1184-1189.

Bakker W.H., et al., "Receptor Scintigraphy With a Radioiodinated Somatostatin Analogue: Radiolabeling, Purification, Biologic Activity, and in Vivo Application in Animals," The Journal of Nuclear Medicine, Sep. 1990, vol. 31, No. 9, pp. 1501-1509.

Banerjee S.R., et al., "Synthesis and Evaluation of Technetium-99m- and Rhenium-labeled Inhibitors of the Prostate-specific Membrane Antigen (PSMA)", Journal of Medicinal Chemistry, vol. 51, No. 15, Aug. 14, 2008, pp. 4504-4517.

Barinka C., et al., "Interactions Between Human Glutamate Carboxypeptidase II and Urea-Based Inhibitors: Structural Characterizations," Journal of Medicinal Chemistry, Dec. 25, 2008, vol. 51, No. 24, pp. 7737-7743 (16 Pages).

(Continued)

*Primary Examiner* — Alan D Diamond
*Assistant Examiner* — Joseph R Kosack
(74) *Attorney, Agent, or Firm* — Casimir Jones, SC; Jeffrey W. Childers

(57) ABSTRACT

Prostate-specific membrane antigen (PSMA) binding compounds having radioisotope substituents are described, as well as chemical precursors thereof. Compounds include pyridine containing compounds, compounds having phenylhydrazine structures, and acylated lysine compounds. The compounds allow ready incorporation of radionuclides for single photon emission computed tomography (SPECT) and positron emission tomography (PET) for imaging, for example, prostate cancer cells and angiogenesis.

30 Claims, 5 Drawing Sheets

(56) References Cited

FOREIGN PATENT DOCUMENTS

| | | | |
|---|---|---|---|
| WO | WO-2008105773 | A2 | 9/2008 |
| WO | WO-2008121949 | A1 | 10/2008 |
| WO | WO-2009002529 | A2 | 12/2008 |
| WO | WO-2009026177 | A1 | 2/2009 |
| WO | WO-2009070302 | A1 | 6/2009 |
| WO | WO-2010014933 | A2 | 2/2010 |
| WO | WO-2010065899 | A2 | 6/2010 |
| WO | WO-2010065902 | A2 | 6/2010 |
| WO | WO-2010065906 | A2 | 6/2010 |
| WO | WO-2010108125 | A2 | 9/2010 |
| WO | WO-2010114723 | A1 | 10/2010 |
| WO | WO-2010147965 | A2 | 12/2010 |

OTHER PUBLICATIONS

Bouvet V., et al., "Automated synthesis of [18 F]DCFPyL via Direct Radiofluorination and Validation in Preclinical Prostate Cancer Models," EJNMMI Research, 2016, vol. 6, No. 40, May 4, 2016, pp. 1-15, XP055457120, DOI: 10.1186/s13550-016-0195-6, the whole document, in particular figures 2, 4, 8, p. 8 below figure 3 etc.

Bzdega T., et al., "The Cloning and Characterization of a Second Brain Enzyme With Naag Peptidase Activity," Journal of Neurochemistry, 2004, vol. 89, pp. 627-635.

Chang S.S., et al., "Five Different Anti-prostate-specific Membrane Antigen (PSMA) Antibodies Confirm PSMA Expression in Tumor-associated Neovasculature," Cancer Research, Jul. 1, 1999, vol. 59, No. 13, pp. 3192-3198 (8 Pages).

Chang S.S., et al., "Overview of Prostate-specific Membrane Antigen," Reviews in Urology, 2004, vol. 6, Supplement 10, pp. S13-S18.

Chen X., et al., "(18) F-labeled RGD Peptide: Initial Evaluation for Imaging Brain Tumor Angiogenesis," Nuclear Medicine and Biology, 2004, vol. 31, pp. 179-189.

Chen Y., et al., "2-(3-{1-Carboxy-5-[(6-[18F]Fluoro-Pyridine-3-Carbonyl)- Amino]- Pentyl}-Ureido)-Pentanedioic Acid, [18F]DCFPyL, a PSMA-Based PET Imaging Agent for Prostate Cancer", Clinical Cancer Research, vol. 17, No. 24, Dec. 15, 2011, pp. 7645-7653, XP055278472, US ISSN: 1078-0432, DOI: 10.1158/1078-0432. CCR-11-1357, p. 7645 -p. 7647 figures 1, 2, compounds 1, 3.

Chen Y., et al., "Radiohalogenated Prostate-specific Membrane Antigen (PSMA)-based Ureas As Imaging Agents for Prostate Cancer", Journal of Medicinal Chemistry, vol. 51, No. 24, 7933-7943, Dec. 25, 2008, pp. 1-28, XP002614473.

Cheng H.C., et al., "The Power Issue: Determination of K(B) or K(i) From IC(50) A Closer Look at the Cheng-Prusoff Equation, the Schild Plot and Related Power Equations," Journal of Pharmacological and Toxicological Methods, 2002, vol. 46, pp. 61-71.

Cho S.Y., et al., "Biodistribution, Tumor Detection, and Radiation Dosimetry of 18F-DCFBC, a Low-molecular-weight Inhibitor of Prostate-specific Membrane Antigen, in Patients with Metastatic Prostate Cancer," Journal of Nuclear Medicine, Dec. 2012, vol. 53, No. 12, pp. 1883-1891 (19 Pages).

De Geus-Oei L.F., et al., "Predictive and Prognostic Value of FOG-PET," Cancer Imaging, 2008, vol. 8, No. 1, pp. 70-80.

Dekker B., et al., "Functional Comparison of Annexin V Analogues Labeled Indirectly and Directly With Iodine-124," Nuclear Medicine and Biology, 2005, vol. 32, pp. 403-413.

Extended European Search Report for European Application No. 09803670.0, mailed Nov. 11, 2014, 6 Pages.

Extended European Search Report for European Application No. 17167057.3, mailed Jul. 18, 2017, 10 Pages.

Extended European Search Report for European Application No. 22163541.0, mailed Sep. 26, 2022, 11 Pages.

Foss C.A., et al., "Radiolabeled Small-molecule Ligands for Prostate-specific Membrane Antigen: In vivo Imaging in Experimental Models of Prostate Cancer," Clinical Cancer Research, Jun. 1, 2005, vol. 11, No. 11, pp. 4022-4028, (8 Pages).

Galsky M.D., et al., "Phase I Trial of the Prostate-Specific Membrane Antigen-Directed Immunoconjugate MLN2704 in Patients With Progressive Metastatic Castration-Resistant Prostate Cancer," Journal of Clinical Oncology, May 1, 2008, vol. 26, No. 13, pp. 2147-2154.

Garg S., et al., "N-succinimidyl 5-(Trialkylstannyl)-3-pyridinecarboxylates: A New Class of Reagents for Protein Radioiodination," Bioconjugate Chemistry, 1991, vol. 2, No. 1, pp. 50-56.

Garg S., et al., "Radioiodination of a Monoclonal Antibody Using N-succinimidyl 5-iodo-3-pyridinecarboxylate," Nuclear Medicine and Biology, 1993, vol. 20, No. 7, pp. 835-842.

Ghirmai S., et al., "Synthesis and Radioiodination of Some Daunorubicin and Doxorubicin Derivatives," Carbohydrate Research, 2005, vol. 340, pp. 15-24.

Guilarte T.R., et al., "Dysregulation of Glutamate Carboxypeptidase II in Psychiatric Disease," Schizophrenia Research, Feb. 2008, vol. 99, pp. 324-332, 15 Pages.

Haseman M.K., et al., "Capromab Pendetide Imaging of Prostate Cancer," Cancer Biotherapy and Radiopharmaceuticals, Nov. 2, 2000, vol. 15, pp. 131-141, 2001.

Hillier S.M., et al., "Abstract B143: Design and Evaluation of Novel Glutamate-Urea Heterodimers that Target PSMA as Molecular Imaging Agents for Prostate Cancer", Molecular Cancer Therapeutics, 2007, 1 page.

Hlouchova K., et al., "Biochemical Characterization of Human Glutamate Carboxypeptidase III," Journal of Neurochemistry, 2007, vol. 101, pp. 682-696.

International Preliminary Report on Patentability for International Application No. PCT/US2009/052456, mailed Feb. 10, 2011, 8 Pages.

International Search Report and Written Opinion for International Application No. PCT/US2017/036681, mailed Sep. 18, 2017, 16 Pages.

Jemal A., et al., "Cancer Statistics, 2003," CA: A Cancer Journal for Clinicians, Jan./Feb. 2003, vol. 53, No. 1, pp. 5-26.

Kozikowski A., LinkedIn post retrieved Aug. 9, 2024, 1 page.

Kozikowski A.P., et al., "Design of Remarkably Simple, Yet Potent Urea-Based Inhibitors of Glutamate Carboxypeptidase II (NAALADase)," Journal of Medicinal Chemistry, 2001, vol. 44, pp. 298-301.

Kozikowski A.P., et al., "How a Medicinal Chemistry Project Changed the Way Prostate Cancer is Diagnosed and Treated", Journal Of Medicinal Chemistry, 2025, vol. 68, pp. 20972-20978.

Kozikowski A.P., et al., "Synthesis of Urea-Based Inhibitors as Active Site Probes of Glutamate Carboxypeptidase II: Efficacy as Analgesic Agents," Journal of Medicinal Chemistry, 2004, vol. 47, No. 7, pp. 1729-1738.

Lange P.H., "ProstaScint Scan for Staging Prostate Cancer," Urology, 2001, vol. 57, pp. 402-406.

Larson S.M., et al., "Tumor Localization of 16(Beta)-18f-fluoro-5(Alpha)-dihydrotestosterone Versus 18f-fdg in Patients With Progressive, Metastatic Prostate Cancer," The Journal of Nuclear Medicine, Mar. 2004, vol. 45, No. 3, pp. 366-373.

Li B., et al., "Aqueous Phosphoric Acid as a Mild Reagent for Deprotection of Tert-Butyl Carbamates, Esters, and Ethers," The Journal of Organic Chemistry, vol. 71, No. 24, Nov. 1, 2006, pp. 9045-9050, XP055304529, United States ISSN: 0022-3263, DOI: 10.1021/jo061377b, in particular pp. 9046-9048, figure 1 and table 2.

Lupold S.E., et al., "Identification and Characterization of Nuclease-stabilized Rna Molecules That Bind Human Prostate Cancer Cells via the Prostate-specific Membrane Antigen," Cancer Research, Jul. 15, 2002, vol. 62, pp. 4029-4033.

Maresca K.P., et al., "A Series of Halogenated Heterodimeric Inhibitors of Prostate Specific Membrane Antigen (PSMA) as Radiolabeled Probes for Targeting Prostate Cancer," Journal of Medicinal Chemistry, Jan. 22, 2009, vol. 52, No. 2, pp. 347-357, (Published Online. Dec. 29, 2008).

Mease R.C., et al., "Synthesis and in vivo Evaluation of N-[N-[(S)-1,3-dicarboxypropyl]carbamoyl]-4-[18F]fluorobenzyl-L-cysteine, [18F]DCFBC: A New Imaging Probe for Prostate Cancer," Clinical Cancer Research, May 15, 2008, vol. 14, No. 10, pp. 3036-3043 (17 Pages).

(56) References Cited

OTHER PUBLICATIONS

Murphy G.P., et al., "Measurement of Serum Prostate-specific Membrane Antigen, a New Prognostic Marker for Prostate Cancer," Urology, 1998, vol. 51, Suppl. 5A, pp. 89-87.
Nan F., et al., "Dual Function Glutamate-related Ligands: Discovery of a Novel, Potent Inhibitor of Glutamate Carboxypeptidase II Possessing mGluR3 Agonist Activity", Journal of Medicinal Chemistry, 2000, vol. 43, No. 5, pp. 772-774.
Non-Final Office Action for U.S. Appl. No. 13/057,044, mailed Jun. 18, 2013, 14 Pages, (Now U.S. Pat. No. 8,778,305).
Oka S., et al., "A Preliminary Study of Anti-1-amino-3-18f-fluorocyclobutyl-1-carboxylic Acid for the Detection of Prostate Cancer," The Journal of Nuclear Medicine, Jan. 2007, vol. 48, No. 1, pp. 46-55.
Olberg D.E., et al., "One step Radiosynthesis of 6-[ 18F]Fluoronicotinic Acid 2,3,5,6-Tetrafluorophenyl Ester ([ 18 F]F-Py-TFP): A New Prosthetic Group for Efficient Labeling of Biomolecules with Fluorine-18," Journal of Medicinal Chemistry, 2010, vol. 53, No. 4, pp. 1732-1740.
Pomper M.G., et al., "11C-MCG: Synthesis, Uptake Selectivity, and Primate PET of a Probe for Glutamate Carboxypeptidase II (NAALADase)," Molecular Imaging, Apr. 2002-Jun. 2002, vol. 1, No. 2, pp. 96-101, (8 Pages).
Pomper M.G., et al., "Discussions with Leaders: A Conversation Between Martin Pomper and Peter Choyke", The Journal of Nuclear Medicine, Jan. 2020, vol. 61, No. 1, pp. 3-5.
Ponde D.E., et al., "18f-fluoroacetate: a Potential Acetate Analog for Prostate Tumor Imaging-in Vivo Evaluation of 18f-fluoroacetate Versus 11c-acetate," The Journal of Nuclear Medicine, Mar. 2007, vol. 48, No. 3, pp. 420-428.
Ravert H.T., et al., "An Improved Synthesis of The Radiolabeled Prostate-Specific Membrane Antigen Inhibitor, [18 F]DCFPyL," Journal of Labelled Compounds and Radiopharmaceuticals, Sep. 2016, vol. 59, No. 11, pp. 439-450 (21 Pages).
Reske S.N., et al., "Imaging Prostate Cancer With 11 C-choline PET/CT," The Journal of Nuclear Medicine, Aug. 2006, vol. 47, No. 8, pp. 1249-1254.
Response to Non-Final Office Action for U.S. Appl. No. 13/057,044, mailed Sep. 18, 2013, 15 Pages, (Now U.S. Pat. No. 8,778,305).
Robinson M.B., et al., "Hydrolysis of the Brain Dipeptide N-Acetyl-L-Aspartyl-L-Glutamate, Identification and Characterization of a Novel N-Acetylated (Alpha)-Linked Acidic Dipeptidase Activity from Rat Brain," The Journal of Biological Chemistry, Oct. 25, 1987, vol. 262, No. 30, pp. 14498-14506.
Rosenthal S.A., et al., "Utility of Capromab Pendetide (Prostascint(R)) Imaging in the Management of Prostate Cancer," Techniques in Urology, 2001, vol. 7, No. 1, pp. 27-37, (13 Pages).
Scher B., et al., "Value of 11 C-choline PET and PET/CT in Patients With Suspected Prostate Cancer," European Journal of Nuclear Medicine Molecular Imaging, 2007, vol. 34, pp. 45-53.
Schuster D.M., et al., "Initial Experience with the Radiotracer Anti-1-Amino-3-18F-Fluorocyclobutane-1-Carboxylic Acid with PET/CT in Prostate Carcinoma," The Journal of Nuclear Medicine, Jan. 2007, vol. 48, No. 1, pp. 56-63.
Silver D.A., et al., "Prostate-specific Membrane Antigen Expression in Normal and Malignant Human Tissues[1]," Clinical Cancer Research, Jan. 1997, vol. 3, No. 1, pp. 81-85 (6 Pages).
Slusher B.S., et al., "Immunocytochemical Localization of the N-acetyl-aspartyl-glutamate (Naag) Hydrolyzing Enzyme N-acetylated Alpha-linked Acidic Dipeptidase (NAALADase)," Journal of Comparative Neurology, 1992, vol. 315, pp. 217-229.
Tang H., et al., "Prostate Targeting Ligands Based on N-acetylated Alpha-linked Acidic Dipeptidase," Biochemical and Biophysical Research Communications, Jul. 18, 2003, vol. 307, No. 1, pp. 8-14.
Tehrani O.S., et al., "Tumor Imaging Using 1-(2'-deoxy-2'-18f-fluoro-beta-darabinofuranosyl) Thymine and PET," The Journal of Nuclear Medicine, Sep. 2007, vol. 48, No. 9, pp. 1436-1441.
Vaidyanathan G., et al., "Improved Synthesis of N-Succinimidyl 4-[(18)F]Fluorobenzoate and its Application to the Labeling of a Monoclonal Antibody Fragment," Bioconjugate Chemistry, vol. 5, No. 4, 1994, pp. 352-356.
Vaidyanathan G., et al., "Labeling Proteins With Fluorine-18 Using N-succinimidyl-4-[18f]fluorobenzoate," International Journal of Radiation Applications and Instrumentation. Part B. Nuclear Medicine and Biology, 1992, vol. 19, No. 3, pp. 275-281.
Vaidyanathan G., et al., "Synthesis of N-succinimidyl 4-[18f]fluorobenzoate, An Agent for Labeling Proteins and Peptides With 18F," Nature Protocol, 2006, vol. 1, No. 4, pp. 1655-1661.
Vees H., et al., "(18)F-Choline and/or (11) C-Acetate Positron Emission Tomography: Detection of Residual or Progressive Subclinical Disease at Very Low Prostate-Specific Antigen Values (less than 1 ng/mL) After Radical Prostatectomy," BJU International, 2007, vol. 99, pp. 1415-1420.
Zhou J., et al., "NAAG Peptidase Inhibitors and Their Potential for Diagnosis and Therapy," Nature Reviews/Drug Discovery, Dec. 2005, vol. 4, pp. 1015-1026.
Alsimaree, A. A., et al. "Pyrrolylquinoline-BF2 and BPh2 BODIPY-Type Analogues: Synthesis, Structural Analysis and Photophysical Properties," Crystals, 2021, vol. 11, No. 9, p. 1103, Sep. 10, 2021 [Retrieved on 2026-07-21], vol. 11, No. 9, Article 1103, 11 p. Retrieved from the Internet: URL: https://www.mdpi.com/2073-4352/11/9/1103.].
Barinka, C, et al. "Structural Basis of Interactions between Human Glutamate Carboxypeptidase II and Its Substrate Analogs," Journal of Molecular Biology, 2008, vol. 376, No. 5, pp. 1438-1450. doi: 10.1016/j.jmb.2007.12.066.
Bruckner, C, et al., "Synthesis of meso-phenyl-4,6-dipyrrins, preparation of their Cu(II), Ni(II), and Zn(II) chelates, and structural characterization of bis[meso-phenyl- 4,6-dipyrrinato]Ni(II)," Canadian Journal of Chemistry, 1996, vol. 74, No. 11, pp. 2182-2193Ni(II).
Chandran S.S., et al., "Characterization of a Targeted Nanoparticle Functionalized With a Urea-based Inhibitor of Prostate-specific Membrane Antigen (PSMA)", Cancer Biology & Therapy, vol. 7, No. 6, Jun. 2008, pp. 974-982.
Dusich, C, et al. "General Approach for the Preparation of Fluorescent PSMA/GCPII Inhibitors," [Abstract ID: 470, Poster Board Space: 29]. Molecular Imaging, 2006, vol. 5, No. 3, pp. 322-323.
Dusich, C, et al., "Synthesis and Validation of a Novel Small-Molecule Fluorescent Probe for PSMA Expression in Human Tumor Neovasculature [Abstract ID: 362]," Molecular Imaging, 2005, vol. 4, No. 3, p. 321.
Foss, C, et al. "Synthesis and Validation of a Novel Small-Molecule Fluorescent Probe for PSMA Expression in Human Tumor Neovasculature, " [Abstract ID: 362]. Molecular Imaging, 2005, vol. 4, No. 3, p. 321.
Guilarte, T. R., et al. "Peripheral benzodiazepine receptor imaging in a trans- synaptic model of neurodegeneration," Neuroscience Letters, 2005, vol. 387, No. 3, pp. 141-144.
Han, M., et al., "Current Clinical Applications of the 111In-Capromab Pendetide Scan (ProstaScint Scan, CYT-356)," Reviews in Urology, 2001, vol. 3, No. 4, pp. 165-171.
Hillier, S. M., "Preclinical evaluation of novel glutamate-urea-lysine analogues that target prostate-specific membrane antigen as molecular imaging pharmaceuticals for prostate cancer," Cancer Research, 2009, vol. 69, pp. 6932-6940.
Hinkle, G. H., et al., "Prostate cancer abdominal metastases detected with indium- 111 capromab pendetide," Journal of Nuclear Medicine, 1998, vol. 39, No. 4, pp. 650-652.
Hofmann, M., et al., "Feasibility of Ga-68-DOTABOM PET in prostate carcinoma patients," European Journal of Nuclear Medicine and Molecular Imaging, 2004, vol. 31, p. S253.
James, S., et al. "Extension of the Single Amino Acid Chelate Concept (SAAC) to Bifunctional Biotin Analogues for Complexation of the M(CO)3+1 Core (M = Tc and Re): Syntheses, Characterization, Biotinidase Stability, and Avidin Binding," Bioconjugate Chemistry, 2006, vol. 17, No. 3, pp. 579-589.

(56) References Cited

OTHER PUBLICATIONS

James, S., et al., "Urea Based Rhenium Tricarbonyl Dipeptide Compounds as Potential Radiopharmaceuticals for PSMA Imaging," [Abstract 258, INOR 258]. 229th ACS National Meeting, 2005, San Diego, CA, 1 page.
Jayaprakash, S., et al. "Design and Synthesis of a PSMA Inhibitor-Doxorubicin Conjugate for Targeted Prostate Cancer Therapy," ChemMedChem, 2006, vol. 1, No. 3, pp. 299-302.
Kularatne S.A., et al., "Design, Synthesis, and Preclinical Evaluation of Prostate- specific Membrane Antigen (PSMA)-targeted-99mtc Radioimaging Agents," Molecular Pharmaceutics, May-Jun. 2009, vol. 6, No. 3, pp. 790-800 (29 pages).
Kularatne S.A., et al., "Prostate-Specific Membrane Antigen Targeted Imaging and Therapy of Prostate Cancer Using a PSMA Inhibitor as a Homing Ligand," Molecular Pharmaceutics, May-Jun. 2009, vol. 6, No. 3, pp. 780-789.
Liu T., et al., "Cell-surface Labeling and Internalization by a Fluorescent Inhibitor of Prostate-specific Membrane Antigen," The Prostate, 2008, vol. 68, pp. 955-964.
Maecke, H. R., et al. "68Ga Labeled Peptides in Tumor Imaging," Journal of Nuclear Medicine, 2005, 46(1 Suppl), pp. 172S-178S.
Maresca, K., et al., "Molecular targeting of prostate cancer with small molecule inhibitors of prostate specific membrane antigen (PSMA)," Journal of Nuclear Medicine, 2007, vol. 48(Supplement 2), p. 25P.
Ragab, S. S. "Synthesis and photolysis of new BODIPY derivatives with chelated boron centre," Journal of Porphyrins and Phthalocyanines, 2021, vol. 25, No. 09, pp. 818-824.
Rong, J. J., et al., "Molecular Modeling of the Interactions of Glutamate Carboxypeptidase II with Its Potent NAAG-Based Inhibitors," Journal of Medicinal Chemistry, 2002, vol. 45, pp. 4140-4152.
Scher, B., "Pet/Ct imaging of recurrent prostate cancer," European Journal of Nuclear Medicine and Molecular Imaging, 2008, vol. 35, pp. 5-8.
Shuttle Pharma. "Shuttle Pharma Developing Pretreatment Diagnostic Blood Tests for Prostate Cancer," Files Provisional Patent for PSMA Ligand Conjugates to Treat Prostate Cancer. GlobeNewswire, Apr. 10, 2025, 5 pages.
Treibs, A., "Difluorboryl-Komplexe von Di- und Tripyrrylmethenen," Liebigs Annalen der Chemie, 1968, vol. 718, No. 1, pp. 208-223.
Tsukamoto T., et al., "Progress in the Discovery and Development of Glutamate Carboxypeptidase II Inhibitors", Drug Discovery Today, vol. 12, No. 17-18, Sep. 2007, pp. 767-776.
Wikipedia of bombesin, 4 pages.—httQs:LLen.wikiQedia.orgLwikiLBombesin. Date Unknown.
Wikipedia page of GYK-DTPA, 3 pages.—httQs:LLen.wikiQedia.orgLwikiL Pendetide. Date Unknown.
Bakker et al., "In vivo use of a radioiodinated somatostatin analogue: dynamics, metabolism, and binding to somatostatin receptor-positive tumors in man," The Journal of Nuclear Medicine, vol. 32, pp. 1184-1189, 1991.
Bakker et al., "Receptor scintigraphy with a radioiodinated somatostatin analogue: radiolabeling, purification, biologic activity, and in vivo application in animals," The Journal of Nuclear Medicine, vol. 31, pp. 1501-1509, 1990.
Banerjee et al., "Synthesis and evaluation of technetium-99m- and rhenium-labeled inhibitors of the prostate-specific membrane antigen (PSMA)," J. Med. Chem., vol. 51, pp. 4504-4517, 2008.
Barinka et al., "Interactions between human glutamate carboxypeptidase II and urea-based inhibitors: Structural Characterizations," J. Med. Chem, vol. 51, pp. 7737-7743, 2008.
Bzdega et al., "The cloning and characterization of a second brain enzyme with NAAG peptidase activity," Journal of Neurochemistry, vol. 89, pp. 627-635, 2004.
Chang "Overview of prostate-specific membrane antigen," Reviews in Urology, vol. 6, Suppl. 10, pp. S13-S18, 2004.
Chang et al., "Five different anti-prostate-specific membrane antigen (PSMA) antibodies confirm PSMA expression in tumor-associated neovasculature," Cancer Research, vol. 59, pp. 3192-3198, 1999.
Chen et al., "$^{18}$F-labeled RGD peptide: initial evaluation for imaging brain tumor angiogenesis," Nuclear Medicine and Biology, vol. 31, pp. 179-189, 2004.
Chen et al., "Radiohalogenated prostate-specific membrane antigen (PSMA)-based ureas as imaging agents for prostate cancer," J. Med. Chem. vol. 51, pp. 7933-7943, 2008.
Cheng, "The power issue: determination of $K_B$ or $K_i$ from $IC_{50}$. A closer look at the Cheng-Prusoff equation, the Schild plot and related power equations," Journal of Pharmacological and Toxicological Methods, vol. 46, pp. 61-71, 2001.
Dekker et al., "Functional comparison of annexin V analogues labeled indirectly and directly with iodine-124," Nuclear Medicine and Biology, vol. 32, pp. 403-413, 2005.
Foss et al., "Radiolabeled small-molecule ligands for prostate-specific membrane antigen: In vivo imaging in experimental models of prostate cancer," Clin. Cancer Res., vol. 11, No. 11, pp. 4022-4028, 2005.
Galsky et al., "Phase I trial of the prostate-specific membrane antigen-directed immunoconjugate MLN2704 in patients with progressive metastatic castration-resistant prostate cancer," Journal of Clinical Oncology, vol. 26, pp. 2147-2154, 2008.
Garg et al., "N-succinimidyl 5-(trialkylstannyl)-3-pyridinecarboxylates: a new class of reagents for protein radioiodination," Bioconjugate Chem., vol. 2, pp. 50-56, 1991.
Garg et al., "Radioiodination of a monoclonal antibody using N-succinimidyl 5-iodo-3-pyridinecarboxylate," Nucl. Med. Biol., vol. 20, pp. 835-842, 1993.
Geus-Oei et al., "Predictive and prognostic value of FDG-PET," Cancer Imaging, vol. 8, pp. 70-80, 2008.
Ghirmai et al., "Synthesis and radioiodination of some daunorubicin and doxorubicin derivatives," Carbohydrate Research, vol. 340, pp. 15-24, 2005.
Haseman et al., "Capromab Pendetide imaging of prostate cancer," Cancer Biother Radiopharm, vol. 15, pp. 131-140, 2001.
Hlouchova et al., "Biochemical characterization of human glutamate carboxypeptidase III," Journal of Neurochemistry, vol. 101, pp. 682-696, 2007.
International Search Report issued in PCT/US2009/052456 dated Mar. 29, 2010.
Jemal et al., "Cancer statistics, 2003," CA Cancer J. Clin., vol. 53, pp. 5-26, 2003.
Kozikowski et al., "Design of remarkably simple, yet potent urea-based inhibitors of glutamate carboxypeptidase II (NAALADase)," J. Med. Chem., vol. 44, pp. 298-301, 2001.
Kozikowski et al., "Synthesis of urea-based inhibitors as active site probes of glutamate carboxypeptidase II: efficacy as analgesic agents," J. Med. Chem., vol. 47, pp. 1729-1738, 2004.
Lange, "Prostascint scan for staging prostate cancer," Urology, vol. 57, pp. 402-406, 2001.
Larson et al., "Tumor localization of 16beta-$^{18}$F-fluoro-5alpha-dihydrotestosterone versus $^{18}$F-FDG in patients with progressive, metastatic prostate cancer," The Journal of Nuclear Medicine, vol. 45, pp. 366-373, 2004.
Lupold et al., "Identification and characterization of nuclease-stabilized RNA molecules that bind human prostate cancer cells via the prostate-specific membrane antigen," Cancer Research, vol. 62, pp. 4029-4033, 2002.
Maresca et al., "A series of halogenated heterodimeric inhibitors of prostate specific membrane antigen (PSMA) as radiolabeled probes for targeting prostate cancer," J. Med. Chem., vol. 52, pp. 347-357, 2009.
Murphy et al., "Measurement of serum prostate-specific membrane antigen, a new prognostic marker for prostate cancer," Urology, vol. 51, pp. 89-97, 1998.
Oka et al., "A preliminary study of anti-1-amino-3-$^{18}$F-fluorocyclobutyl-1-carboxylic acid for the detection of prostate cancer," The Journal of Nuclear Medicine, vol. 48, pp. 46-55, 2007.

(56) References Cited

OTHER PUBLICATIONS

Ponde et al., "$^{18}$F-fluoroacetate: a potential acetate analog for prostate tumor imaging—in vivo evaluation of $^{18}$F-fluoroacetate versus $^{11}$C-acetate," The Journal of Nuclear Medicine, vol. 48, pp. 420-428, 2007.
Reske et al., "Imaging prostate cancer with $^{11}$C-choline PET/CT," J. Nucl. Med., vol. 47, pp. 1249-1254, 2006.
Robinson et al., "Hydrolysis of the brain dipeptide N-acetyl-L-aspartyl-L-glutamate. Identification and characterization of a novel N-acetylated alpha-linked acidic dipeptidase activity from rat brain," The Journal of Biological Chemistry, vol. 262, pp. 14498-14506, 1987.
Scher et al., "Value of $^{11}$C-choline PET and PET/CT in patients with suspected prostate cancer," European Journal of Nuclear Medicine Molecular Imaging, vol. 34, pp. 45-53, 2007.
Schuster et al., "Initial experience with the radiotracer anti-1-amino-3-$^{18}$F-fluorocyclobutane-1-carboxylic acid with PET/CT in prostate carcinoma," The Journal of Nuclear Medicine, vol. 48, pp. 56-63, 2007.
Silver et al., "Prostate-specific membrane antigen expression in normal and malignant human tissues," Clinical Cancer Research, vol. 3, pp. 81-85, 1997.
Slusher et al., "Immunocytochemical localization of the N-acetyl-aspartyl-glutamate (NAAG) hydrolyzing enzyme N-acetylated alpha-linked acidic dipeptidase (NAALADase)," J.Comp. Neuro., vol. 315, pp. 217-229, 1992.
Tang et al., "Prostate targeting ligands based on n-acetylated $\alpha$-linked acidic dipeptidase," Biochemical and Biophysical Research Communications, vol. 307, pp. 8-14, 2003.
Tehrani et al., "Tumor imaging using 1-(2'-deoxy-2'-$^{18}$F-fluoro-beta-D-arabinofuranosyl)thymine and PET," The Journal of Nuclear Medicine, vol. 48, pp. 1436-1441, 2007.
Vaidyanathan et al., "Improved synthesis of N-succinimidyl 4-[$^{18}$F]fluorobenzoate and its application to the labeling of a monoclonal antibody fragment," Bioconjugate Chem., vol. 5, pp. 352-356, 1994.
Vaidyanathan et al., "Labeling proteins with fluorine-18 using N-succinimidyl-4-[$^{18}$F]fluorobenzoate", Int. J. Rad. Appl. Instrum., Part B, vol. 19, pp. 275-281, 1992.
Vaidyanathan et al., "Synthesis of N-succinimidyl 4-[$^{18}$F]fluorobenzoate, an agent for labeling proteins and peptides with $^{18}$F," Nature Protocols, vol. 1, pp. 1655-1661, 2006.
Vees et al., "$^{18}$F-choline and/or $^{11}$C-acetate positron emission tomography: detection of residual or progressive subclinical disease at very low prostate-specific antigen values (<1ng/mL) after radical prostatectomy," BJU International, vol. 99, pp. 1415-1420, 2007.
Zhou et al., "NAAG peptidase inhibitors and their potential for diagnosis and therapy," Nature Reviews/Drug Discovery, vol. 4, pp. 1015-1026, 2005.
Rosenthal et al., "Utility of capromab pendetide (prostascint®) imaging in the management of prostate cancer," Techniques in Urology, vol. 7, No. 1, pp. 27-37, 2001.

* cited by examiner

PSMA-BINDING AGENTS AND USES THEREOF

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*STATEMENT OF GOVERNMENTAL INTEREST*

This invention was made with government support under grant numbers CA092871,CA114111, CA111982, awarded by the National Institutes of Health, and grant number W81XWH-06-1-0134,awarded by ARMY/MRMC. The government has certain rights in the invention.

CROSS-REFERENCE TO RELATED APPLICATION

This application claims priority to U.S. Provisional Application Nos. 61/085,462 filed Aug. 1, 2008, and 61/111,791 file Nov. 6, 2008, the entire contents of which are hereby incorporated by reference.

BACKGROUND

1. Field of the Invention

The present invention relates generally to radioisotope labeled prostate specific membrane antigen (PSMA) binding compounds, chemical precursors of radioisotope labeled PSMA binding compounds and imaging methods using the radioisotope labeled compounds.

2. Background

Prostate cancer (PCa) is the second leading cause of cancer-related death in men (1). Only one half of tumors due to PCa are clinically localized at diagnosis and one half of those represent extracapsular spread. Localization of that spread as well as determination of the total body burden of PCa have important implications for therapy, particularly as new combination and focal therapies become available. Also critically needed are targeted agents that can provide a readout on the biology of the tumor, with the ability to predict which tumors will lie dormant and which will develop into aggressive, metastatic disease. The current clinical standard for localizing cancer—including PCa—is shifting from the anatomic techniques such as computed tomography (CT) and magnetic resonance (MR) imaging to more physiologically relevant methods that employ molecular imaging, such as MR spectroscopy, single photon emission computed tomography (SPECT) and positron emission tomography (PET) (2). Such newer methods that utilize molecular imaging may provide the biological readout necessary for understanding tumor physiology, enabling more accurate prognosis and therapeutic monitoring. Molecular imaging may provide a way to not only detect tumors in vivo, but also to provide information regarding the biology of the lesion, if a mechanism-specific agent is used. For example, [$^{18}$F]FDHT can be used to study the androgen receptor status of tumors (3).

Unlike many other cancers, PCa is particularly difficult to detect using existing molecular imaging tracers. There are several reasons for this, including the relatively slow growth and metabolic rate of PCa compared to other malignancies as well as the small size of the organ and proximity to the urinary bladder, into which most radiopharmaceuticals are eventually excreted.

Because of the relatively low metabolism of PCa, PET with [$^{18}$F]fluorodeoxyglucose (FDG-PET) has proved ineffectual for diagnostic imaging of this disease. Other promising, experimental radiopharmaceuticals for imaging PCa are emerging, including those of the choline series (4)(5)(6), radiolabeled acetates (7), anti-1-amino-3-[$^{18}$F]fluorocyclobutyl-1-carboxylic acid (anti[$^{18}$F]F-FACBC) (8)(9), 1-(2-deoxy-2-[$^{18}$F]fluoro-L-arabinofuranosyl)-5-methyluracil ([$^{18}$F]FMAU) (10) and [$^{18}$F]fluorodihydrotestosterone ([$^{18}$F]FDHT) (3). Each has its benefits and detriments, with no single agent ideal, i.e., easy to synthesize, little metabolism and demonstrating tumor-specific uptake, in all PCa phenotypes.

Overexpressed on most solid tumor neovasculature (11) as well as in prostate cancer, the prostate-specific membrane antigen (PSMA) is becoming an attractive target for cancer imaging and therapy (12)(13). PSMA-based agents can report on the presence of this marker, which is increasingly recognized as an important prognostic determinate in PCa (14). It is also the target for a variety of new PCa therapies (15). ProstaScint™ is an $^{111}$In-labeled monoclonal antibody against PSMA that is clinically available for imaging PCa. ProstaScint™ and radiolabeled variations of this antibody are fraught with long circulation times and poor target to nontarget tissue contrast, limiting the utility of these agents (16)(17)(18).

SUMMARY OF THE INVENTION

The present invention satisfies the long standing and unmet need for new tissue-specific compounds for imaging prostate cancer and angiogenesis. The present invention, in particular, provides imaging agents which differ from the prior art in modifications which were not previously known or suggested. Furthermore, the invention provides imaging agents that offer better contrast between target tissues and non-target tissues.

The invention relates to compounds having the structure (I) shown below.

(I)

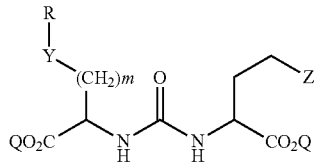

wherein Z is tetrazole or $CO_2Q$; each Q is independently selected from hydrogen or a protecting group.

In some embodiments of Formula I, m is 0, 1, 2, 3, 4, 5, or 6; R is a pyridine ring with the structure

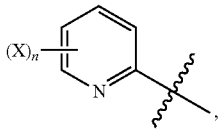

,

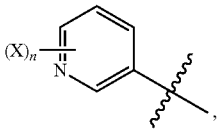

, or

-continued

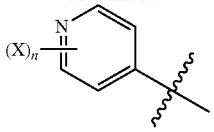

wherein X is fluorine, iodine, a radioisotope of fluorine, a radioisotope of iodine, chlorine, bromine, a radioisotope of bromine, a radioisotope of astatine, $NO_2$, $NH_2$, $N^+(R^2)_3$, $Sn(R^2)_3$, $Si(R^2)_3$, $Hg(R^2)$, $B(OH)_2$, —$NHNH_2$, —NHN═$CHR^3$, —NHNH—$CH_2R^3$; n is 1, 2, 3, 4, or 5; Y is O, S, N(R'), C(O), NR'C(O), C(O)N(R'), OC(O), C(O)O, NR'C(O)NR', NR'C(S)NR', NR'$S(O)_2$, $S(CH_2)_p$, NR'$(CH_2)_p$, $O(CH_2)_p$, OC(O)$CHR^8$NHC(O), NHC(O)$CHR^8$NHC(O), or a covalent bond; wherein p is 1, 2, or 3, R' is H or $C_1$-$C_6$ alkyl, and $R^8$ is alkyl, aryl or heteroaryl, each of which may be substituted; $R^2$ is $C_1$-$C_6$ alkyl; and $R^3$ is alkyl, alkenyl, alkynyl, aryl, or heteroaryl each of which is substituted by fluorine, iodine, a radioisotope of fluorine, a radioisotope of iodine, bromine, a radioisotope of bromine, a radioisotope of astatine, $NO_2$, $NH_2$, $N^+(R^2)_3$, $Sn(R^2)_3$, $Si(R^2)_3$, $Hg(R^2)$, or $B(OH)_2$.

In some embodiments of Formula I, m is 0, 1, 2, 3, 4, 5, or 6; Y is O, S, N(R'), C(O), NR'C(O), C(O)N(R'), OC(O), C(O)O, NR'C(O)NR', NR'C(S)NR', NR'$S(O)_2$, $S(CH_2)_p$, NR'$(CH_2)_p$, $O(CH_2)_p$, OC(O)$CHR^8$NHC(O), NHC(O)$CHR^8$NHC(O), or a covalent bond; wherein p is 1, 2, or 3, R' is H or $C_1$-$C_6$ alkyl, and $R^8$ is alkyl, aryl or heteroaryl, each of which may be substituted; R is

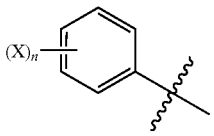

wherein X' is selected from the group consisting of $NHNH_2$, —NHN═$CHR^3$, and —NHNH—$CH_2R^3$; wherein $R^3$ is alkyl, alkenyl, alkynyl, aryl, or heteroaryl each of which is substituted by fluorine, iodine, a radioisotope of fluorine, a radioisotope of iodine, chlorine, bromine, a radioisotope of bromine, or a radioisotope of astatine, $NO_2$, $NH_2$, $N^+(R^2)_3$, $Sn(R^2)_3$, $Si(R^2)_3$, $Hg(R^2)$, or $B(OH)_2$; and n is 1, 2, 3, 4, or 5.

In other embodiments of Formula I, m is 4, Y is NR', and R is

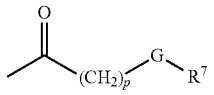

wherein G is O, NR' or a covalent bond; R' is H or $C_1$-$C_6$ alkyl; p is 1, 2, 3, or 4, and $R^7$ is selected from the group consisting of $NH_2$, N═$CHR^3$, NH—$CH_2R^3$, wherein $R^3$ is alkyl, alkenyl, alkynyl, aryl, or heteroaryl each of which is substituted by fluorine, iodine, a radioisotope of fluorine, a radioisotope of iodine, chlorine, bromine, a radioisotope of bromine, a radioisotope of astatine, $NO_2$, $NH_2$, $N^+(R^2)_3$, $Sn(R^2)_3$, $Si(R^2)_3$, $Hg(R^2)$, or $B(OH)_2$.

Some compounds of the present invention interact with the prostate-specific membrane antigen (PSMA). As a result, when the compounds comprise a radioisotope, they may be suitable as imaging agents, diagnostic agents, and/or therapeutic agents.

In many cases, the radioisotope used in the compound is short-lived. Therefore, radioisotopically labeled compounds are prepared immediately or shortly before use, or only in sufficient quantity for administration. For this reason, the invention also includes precursors to radioisotopically labeled compounds, which may be chemically converted into the radioisotopically labeled compounds of the invention.

DETAILED DESCRIPTION OF EXEMPLARY EMBODIMENTS

Figure 1:
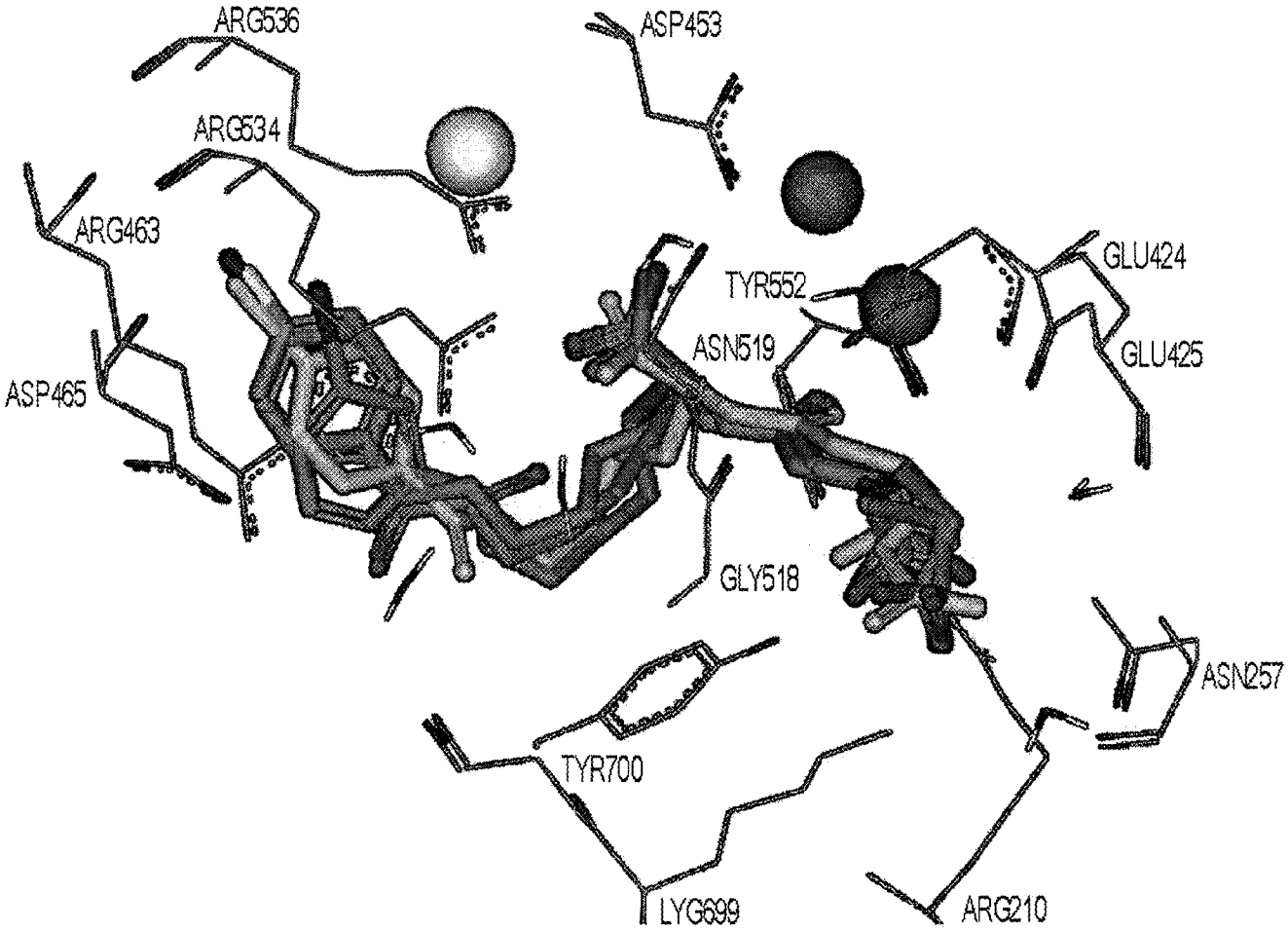
FIG. 1 shows an overlay of the best poses for 3, 6 and 8 with the crystal ligand, i.e., 3 as it is co-crystallized with PSMA, in the presence of water molecule in the active site of PSMA (PDB ID: 3D7H). Dark spheres (zinc ions), light sphere (chloride ion).

Embodiments of the invention include compounds according to formula I, shown below:

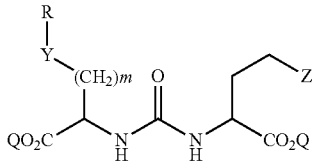

(I)

wherein Z is tetrazole or $CO_2Q$, and each Q is independently selected from hydrogen or a protecting group.

In exemplary embodiments (A), m is 0, 1, 2, 3, 4, 5, or 6, R is a pyridine ring selected from the group consisting of

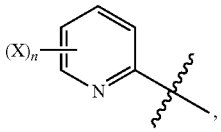

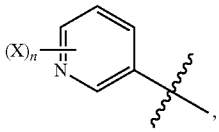

and

-continued

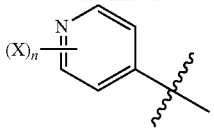

wherein X is fluorine, iodine, a radioisotope of fluorine, a radioisotope of iodine, chlorine, bromine, a radioisotope of bromine, a radioisotope of astatine, $NO_2$, $NH_2$, $N^+(R^2)_3$, $Sn(R^2)_3$, $Si(R^2)_3$, $Hg(R^2)$, $B(OH)_2$, —$NHNH_2$, —NHN═$CHR^3$, —NHNH—$CH_2R^3$; n is 1, 2, 3, 4, or 5; Y is O, S, N(R'), C(O), NR'C(O), C(O)N(R'), OC(O), C(O)O, NR'C(O)NR', NR'C(S)NR', NR'S$(O)_2$, S$(CH_2)_p$, NR'$(CH_2)_p$, O$(CH_2)_p$, OC(O)$CHR^8$NHC(O), NHC(O)$CHR^8$NHC(O), or a covalent bond; p is 1, 2, or 3, R' is H or $C_1$-$C_6$ alkyl, and $R^8$ is alkyl, aryl or heteroaryl, each of which may be substituted; $R^2$ is $C_1$-$C_6$ alkyl; and $R^3$ is alkyl, alkenyl, alkynyl, aryl, or heteroaryl each of which is substituted by fluorine, iodine, a radioisotope of fluorine, a radioisotope of iodine, chlorine, bromine, a radioisotope of bromine, or a radioisotope of astatine, $NO_2$, $NH_2$, $N^+(R^2)_3$, $Sn(R^2)_3$, $Si(R^2)_3$, $Hg(R^2)$, or $B(OH)_2$; or a pharmaceutically acceptable salt thereof.

In other embodiments (B), m is 0, 1, 2, 3, 4, 5, or 6; Y is O, S, N(R'), C(O), NR'C(O), C(O)N(R'), OC(O), C(O)O, NR'C(O)NR', NR'C(S)NR', NR'S$(O)_2$, S$(CH_2)_p$, NR'$(CH_2)_p$, O$(CH_2)_p$, OC(O)$CHR^8$NHC(O), NHC(O)$CHR^8$NHC(O), or a covalent bond; p is 1, 2, or 3; R' is H or $C_1$-$C_6$ alkyl; $R^8$ is alkyl, aryl or heteroaryl, each of which may be substituted; R is

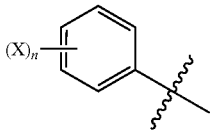

wherein X' is selected from the group consisting of $NHNH_2$, —NHN═$CHR^3$, and —NHNH—$CH_2R^3$; wherein $R^3$ is alkyl, alkenyl, alkynyl, aryl, or heteroaryl each of which is substituted by fluorine, iodine, a radioisotope of fluorine, a radioisotope of iodine, chlorine, bromine, a radioisotope of bromine, or a radioisotope of astatine; $NO_2$, $NH_2$, $N^+(R^2)_3$, $Sn(R^2)_3$, $Si(R^2)_3$, $Hg(R^2)$, or $B(OH)_2$; $R^2$ is $C_1$-$C_6$ alkyl; n is 1, 2, 3, 4, or 5; or a pharmaceutically acceptable salt thereof.

In yet other embodiments (C), m is 4; Y is NR'; and R is

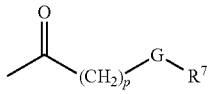

wherein G is O, NR' or a covalent bond; R' is H or $C_1$-$C_6$ alkyl; p is 1, 2, 3, or 4, and $R^7$ is selected from the group consisting of $NH_2$, N═$CHR^3$, NH—$CH_2R^3$, wherein $R^3$ is alkyl, alkenyl, alkynyl, aryl, or heteroaryl each of which is substituted by fluorine, iodine, a radioisotope of fluorine, a radioisotope of iodine, bromine, a radioisotope of bromine, or a radioisotope of astatine; $NO_2$, $NH_2$, $N^+(R^2)_3$, $Sn(R^2)_3$, $Si(R^2)_3$, $Hg(R^2)$, or $B(OH)_2$; $R^2$ is $C_1$-$C_6$ alkyl; or a pharmaceutically acceptable salt thereof.

The compounds herein described may have one or more asymmetric centers or planes. Compounds of the present invention containing an asymmetrically substituted atom may be isolated in optically active or racemic forms. It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

The compounds herein described may have one or more charged atoms. For example, the compounds may be zwitterionic, but may be neutral overall. Other embodiments may have one or more charged groups, depending on the pH and other factors. In these embodiments, the compound may be associated with a suitable counter-ion. It is well known in the art how to prepare salts or exchange counter-ions. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Counter-ions may be changed, for example, by ion-exchange techniques such as ion-exchange chromatography. All zwitterions, salts and counter-ions are intended, unless the counter-ion or salt is specifically indicated. In certain embodiments, the salt or counter-ion may be pharmaceutically acceptable, for administration to a subject. Pharmaceutically acceptable salts are discussed later.

When any variable occurs more than one time in any constituent or formula for a compound, its definition at each occurrence is independent of its definition at every other occurrence. Thus, for example, if a group is shown to be substituted with $(X)_n$, where n is 1, 2, 3, 4, or 5, then said group may optionally be substituted with up to five X groups and each occurrence is selected independently from the definition of X. Also, combinations of substituents and/or variables are permissible only if such combinations result in stable compounds.

As indicated above, various substituents of the various formulae are "substituted" or "may be substituted." The term "substituted," as used herein, means that any one or more hydrogens on the designated atom or group is replaced with a substituent, provided that the designated atom's normal valence is not exceeded, and that the substitution results in a stable compound. When a substituent is oxo (keto, i.e., =0), then 2 hydrogens on an atom are replaced. The present invention is intended to include all isotopes (including radioisotopes) of atoms occurring in the present compounds. When the compounds are substituted, they may be so substituted at one or more available positions, typically 1, 2, 3 or 4 positions, by one or more suitable groups such as those disclosed herein. Suitable groups that may be present on a "substituted" group include e.g., halogen; cyano; hydroxyl; nitro; azido; amino; alkanoyl (such as a $C_1$-$C_6$ alkanoyl group such as acyl or the like); carboxamido; alkyl groups (including cycloalkyl groups, having 1 to about 8 carbon atoms, for example 1, 2, 3, 4, 5, or 6 carbon atoms); alkenyl and alkynyl groups (including groups having one or more unsaturated linkages and from 2 to about 8, such as 2, 3, 4, 5 or 6, carbon atoms); alkoxy groups having one or more oxygen linkages and from 1 to about 8, for example 1, 2, 3, 4, 5 or 6 carbon atoms; aryloxy such as phenoxy; alkylthio groups including those having one or more thioether linkages and from 1 to about 8 carbon atoms, for example 1, 2, 3, 4, 5 or 6 carbon atoms; alkylsulfinyl groups including those having one or more sulfinyl linkages and from 1 to about 8 carbon atoms, such as 1, 2, 3, 4, 5, or 6 carbon atoms; alkylsulfonyl groups including those having one or more sulfonyl linkages and from 1 to about 8 carbon atoms, such as 1, 2, 3, 4, 5, or 6 carbon atoms; aminoalkyl groups including groups having one or more N atoms and from 1 to about 8, for example 1, 2, 3, 4, 5 or 6, carbon atoms; carbocyclic aryl having 4, 5, 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, (e.g. benzyl); arylalkoxy having 1 to 3 separate or fused rings and from 6 to about 18 ring carbon atoms (e.g. O-benzyl); or a saturated, unsaturated, or aromatic heterocyclic group having 1 to 3 separate or fused rings with 3 to about 8 members per ring and one or more N, O or S atoms, (e.g. coumarinyl, quinolinyl, isoquinolinyl, quinazolinyl, pyridyl, pyrazinyl, pyrimidyl, furanyl, pyrrolyl, thienyl, thiazolyl, triazinyl, oxazolyl, isoxazolyl, imidazolyl, indolyl, benzofuranyl, benzothiazolyl, tetrahydropyranyl, tetrahydropyranyl, piperidinyl, morpholinyl, piperazinyl, and pyrrolidinyl). Such heterocyclic groups may be further substituted, e.g. with hydroxy, alkyl, alkoxy, halogen and amino.

As used herein, "alkyl" is intended to include branched, straight-chain, and cyclic saturated aliphatic hydrocarbon groups. Examples of alkyl include, but are not limited to, methyl, ethyl, n-propyl, iso-propyl, n-butyl, sec-butyl, tent-butyl, n-pentyl, and sec-pentyl. In certain embodiments, alkyl groups are $C_1$-$C_6$ alkyl groups or $C_1$-$C_4$ alkyl groups. Particular alkyl groups are methyl, ethyl, propyl, butyl, and 3-pentyl. The term "$C_1$-$C_6$ alkyl" as used herein means straight-chain, branched, or cyclic $C_1$-$C_6$ hydrocarbons which are completely saturated and hybrids thereof such as (cycloalkyl)alkyl. Examples of $C_1$-$C_6$ alkyl substituents include methyl (Me), ethyl (Et), propyl (including n-propyl (n-Pr, $^n$Pr), iso-propyl (i-Pr, $^i$Pr), and cyclopropyl (c-Pr, $^c$Pr)), butyl (including n-butyl (n-Bu, $^n$Bu), iso-butyl (i-Bu, $^i$Bu), sec-butyl (s-Bu, $^s$Bu), tert-butyl (t-Bu, $^t$Bu), or cyclobutyl (c-Bu, $^c$Bu)), and so forth. "Cycloalkyl" is intended to include saturated ring groups, such as cyclopropyl, cyclobutyl, cyclopentyl, or cyclohexyl. Cycloalkyl groups typically will have 3 to about 8 ring members. In the term "(cycloalkyl)alkyl", cycloalkyl, and alkyl are as defined above, and the point of attachment is on the alkyl group. This term encompasses, but is not limited to, cyclopropylmethyl, cyclopentylmethyl, and cyclohexylmethyl.

As used herein, "alkenyl" is intended to include hydrocarbon chains of either a straight or branched configuration comprising one or more unsaturated carbon-carbon bonds, which may occur in any stable point along the chain, such as ethenyl and propenyl. Alkenyl groups typically will have 2 to about 8 carbon atoms, more typically 2 to about 6 carbon atoms.

As used herein, "alkynyl" is intended to include hydrocarbon chains of either a straight or branched configuration comprising one or more carbon-carbon triple bonds, which may occur in any stable point along the chain, such as ethynyl and propynyl. Alkynyl groups typically will have 2 to about 8 carbon atoms, more typically 2 to about 6 carbon atoms.

As used herein, "haloalkyl" is intended to include both branched and straight-chain saturated aliphatic hydrocarbon groups having the specified number of carbon atoms, substituted with 1 or more halogen atoms. Examples of haloalkyl include, but are not limited to, mono-, di-, or tri-fluoromethyl, mono-, di-, or tri-chloromethyl, mono-, di-, tri-, tetra-, or penta-fluoroethyl, and mono-, di-, tri-, tetra-, or penta-chloroethyl, etc. Typical haloalkyl groups will have 1 to about 8 carbon atoms, more typically 1 to about 6 carbon atoms.

As used herein, "alkoxy" represents an alkyl group as defined above attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Alkoxy groups typically have 1 to about 8 carbon atoms, more typically 1 to about 6 carbon atoms.

As used herein, "haloalkoxy" represents a haloalkyl group as defined above with the indicated number of carbon atoms attached through an oxygen bridge. Haloalkoxy groups will have 1 to about 8 carbon atoms, more typically 1 to about 6 carbon atoms.

As used herein, "alkylthio" includes those groups having one or more thioether linkages and typically from 1 to about 8 carbon atoms, more typically 1 to about 6 carbon atoms.

As used herein, the term "alkylsulfinyl" includes those groups having one or more sulfoxide (SO) linkage groups and typically from 1 to about 8 carbon atoms, more typically 1 to about 6 carbon atoms.

As used herein, the term "alkylsulfonyl" includes those groups having one or more sulfonyl ($SO_2$) linkage groups and typically from 1 to about 8 carbon atoms, more typically 1 to about 6 carbon atoms.

As used herein, the term "alkylamino" includes those groups having one or more primary, secondary and/or tertiary amine groups and typically from 1 to about 8 carbon atoms, more typically 1 to about 6 carbon atoms.

As used herein, "Halo" or "halogen" refers to fluoro, chloro, bromo, or iodo; and "counter-ion" is used to represent a small, negatively charged species such as chloride, bromide, hydroxide, acetate, sulfate, and the like.

As used herein, "carbocyclic group" is intended to mean any stable 3- to 7-membered monocyclic or bicyclic or 7-to 13-membered bicyclic or tricyclic group, any of which may be saturated, partially unsaturated, or aromatic. In addition to those exemplified elsewhere herein, examples of such carbocycles include, but are not limited to, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, and tetrahydronaphthyl.

As used herein, the term "aryl" includes groups that contain 1 to 3 separate or fused rings and from 6 to about 18 ring atoms, without hetero atoms as ring members. Example os aryl groups include include but are not limited to phenyl, and naphthyl, including 1-naphthyl and 2-naphthyl.

As used herein, "heterocyclic group" is intended to include saturated, partially unsaturated, or unsaturated (aromatic) groups having 1 to 3 (possibly fused) rings with 3 to about 8 members per ring at least one ring containing an atom selected from N, O or S. The nitrogen and sulfur heteroatoms may optionally be oxidized. The term or "heterocycloalkyl" is used to refer to saturated heterocyclic groups.

A heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized.

As used herein, the term "heteroaryl" is intended to include any stable 5-to 7-membered monocyclic or 10- to 14-membered bicyclic heterocyclic aromatic ring system which comprises carbon atoms and from 1 to 4 heteroatoms independently selected from the group consisting of N, O and S. In exemplary embodiments, the total number of S and O atoms in the aromatic heterocycle is not more than 2, and typically not more than 1.

Examples of heteroaryl include, but are not limited to, those exemplified elsewhere herein and further include acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H.6HA,5,2-dithiazinyl, dihydrofuro[2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; −1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Exemplary heteroaryl groups include, but are not limited to, pyridinyl, pyrimidinyl, furanyl, thienyl, pyrrolyl, pyrazolyl, pyrrolidinyl, morpholinyl, piperidinyl, piperazinyl, and imidazolyl.

In certain embodiments, Z is tetrazole or $CO_2Q$. When Z is tetrazole, the tetrazole ring is attached through the carbon atom, as shown below.

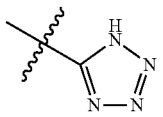

In certain embodiments, Q is a protecting group. As used herein, a "protecting group" is a chemical substituent which can be selectively removed by readily available reagents which do not attack the regenerated functional group or other functional groups in the molecule. Suitable protecting groups may be found, for example in Wutz et al. ("Greene's Protective Groups in Organic Synthesis, Fourth Edition," Wiley-Interscience, 2007). Protecting groups for protection of the carboxyl group, as described by Wutz et al. (pages 533-643), are used in certain embodiments. In some embodiments, the protecting group is removable by treatment with acid. Specific examples of protecting groups include but are not limited to, benzyl, p-methoxybenzyl (PMB), tertiary butyl ($^t$Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr).

In some embodiments, $R^8$ is alkyl, aryl or heteroaryl, each of which may be substituted. In certain embodiments, $R^8$ describes the sidechain of a natural or synthetic α-amino acid. Specific examples of $R^8$ include hydrogen, methyl ($CH_3$), isopropyl ($CH(CH_3)_2$), 2,2-dimethylethyl ($CH_2CH(CH3)_2$), 2-methylpropyl ($CH(CH_3)CH_2CH_3$), phenyl, 4-hydroxyphenyl, hydroxymethyl ($CH_2OH$), carboxymethyl ($CH_2CO_2H$), thiomethyl ($CH_2SH$), imidazolylmethyl, indolylmethyl, and so forth.

Certain embodiments include compounds according to formula I where Z is $CO_2Q$. In other embodiments, Q is hydrogen. In some specific embodiments, Z is $CO_2Q$ and Q is hydrogen.

Certain embodiments include compounds according to formula I, where m is 1, 2, 3, or 4.

Other embodiments include compounds according to formula I wherein m is 0, 1, 2, 3, 4, 5, or 6; R is a pyridine ring selected from the group consisting of

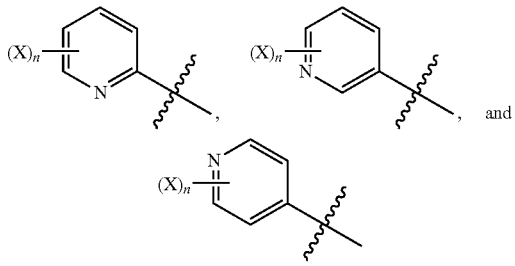

wherein X is fluorine, iodine, a radioisotope of fluorine, a radioisotope of iodine, chlorine, bromine, a radioisotope of bromine, a radioisotope of astatine, $NO_2$, $NH_2$, $N^+(R^2)_3$, $Sn(R^2)_3$, $Si(R^2)_3$, $Hg(R^2)$, $B(OH)_2$, —$NHNH_2$, —NHN═$CHR^3$, —NHNH—$CH_2R^3$. In certain embodiments, n is 1. Each Q is independently selected from hydrogen or a protecting group; Z is tetrazole or $CO_2Q$; Y is O, S, N(R'), C(O), NR'C(O), C(O)N(R'), OC(O), C(O)O, NR'C(O)NR', NR'C(S)NR', NR'S$(O)_2$, S$(CH_2)_p$, NR'$(CH_2)_p$, O$(CH_2)_p$, OC(O)CH$R^8$NHC(O), NHC(O)CH$R^8$NHC(O), or a covalent bond; wherein p is 1, 2, or 3, R' is H or $C_1$-$C_6$ alkyl, and $R^8$ is alkyl, aryl or heteroaryl, each of which may be substituted; $R^2$ is $C_1$-$C_6$ alkyl; and $R^3$ is alkyl, alkenyl, alkynyl, aryl, or heteroaryl each of which is substituted by fluorine, iodine, a radioisotope of fluorine, a radioisotope of iodine, chlorine bromine, a radioisotope of bromine, or a radioisotope of astatine; $NO_2$, $NH_2$, $N^+(R^2)_3$, $Sn(R^2)_3$, $Si(R^2)_3$, $Hg(R^2)$, or $B(OH)_2$. In certain embodiments, $R^3$ is aryl, substituted by fluorine, iodine, a radioisotope of fluorine, a radioisotope of iodine, bromine, a radioisotope of bromine, or a radioisotope of astatine.

Other embodiments include compounds having the structure

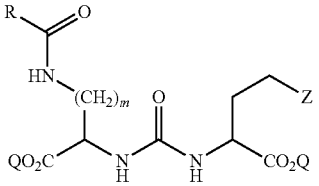

wherein m is not 0. R is a pyridine ring selected from the group consisting of

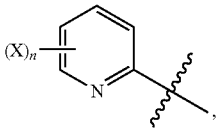

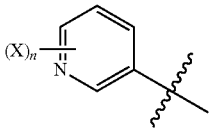

and

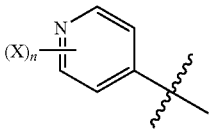

wherein X is fluorine, iodine, a radioisotope of fluorine, a radioisotope of iodine, chlorine, bromine, a radioisotope of bromine, a radioisotope of astatine, $NO_2$, $NH_2$, $N^+(R^2)_3$, $Sn(R^2)_3$, $Si(R^2)_3$, $Hg(R^2)$, $B(OH)_2$, —$NHNH_2$, —NHN═$CHR^3$, or —NHNH—$CH_2R^3$. $R^2$ is $C_1$-$C_6$ alkyl; and $R^3$ is alkyl, alkenyl, alkynyl, aryl, or heteroaryl each of which is substituted by fluorine, iodine, a radioisotope of fluorine, a radioisotope of iodine, chlorine bromine, a radioisotope of bromine, or a radioisotope of astatine; $NO_2$, $NH_2$, $N^+(R^2)_3$, $Sn(R^2)_3$, $Si(R^2)_3$, $Hg(R^2)$, or $B(OH)_2$. In certain embodiments, n is 1. Other specific embodiments include compounds where X is fluorine, iodine, or a radioisotope of fluorine, a radioisotope of iodine, chlorine, bromine, a radioisotope of bromine, or a radioisotope of astatine. In certain embodiments, $R^3$ is aryl, substituted by fluorine, iodine, a radioisotope of fluorine, a radioisotope of iodine, bromine, a radioisotope of bromine, or a radioisotope of astatine. Specific embodiments include compounds having the structure shown above, where Z is $CO_2Q$, Q is hydrogen, and m is 4.

Compounds according to this embodiment can be prepared, for example, from p-methoxybenzyl (PMB) protected precursor Lys-C(O)-Glu according to Scheme 1 shown below.

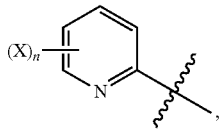

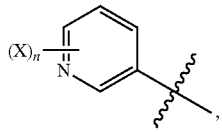

and

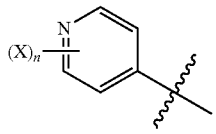

Other embodiments include compounds having the structure

Scheme 1

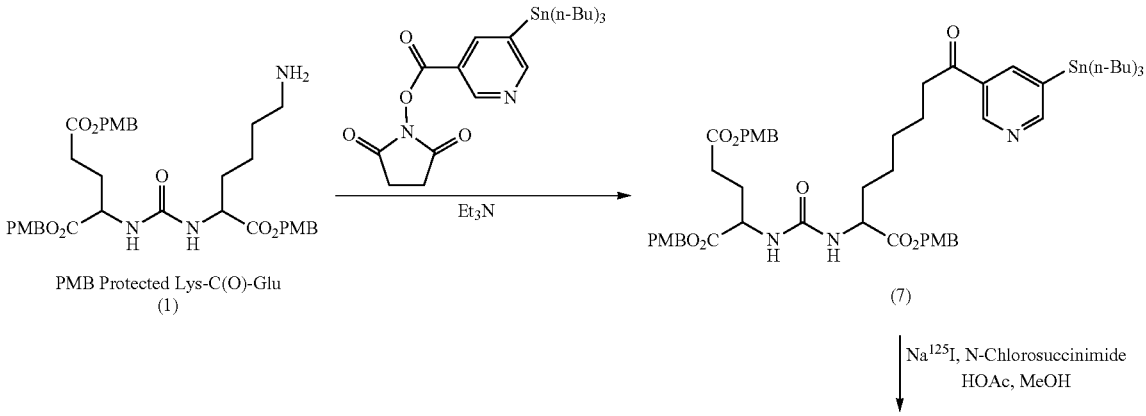

-continued

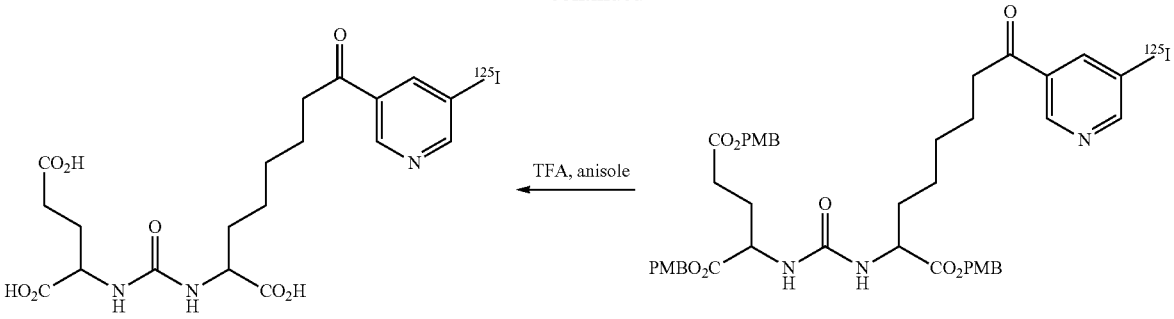

([$^{125}$I]8)

wherein m is not 0. R is a pyridine ring selected from the group consisting of

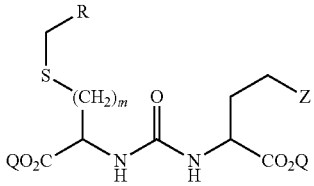

wherein X is fluorine, iodine, a radioisotope of fluorine, a radioisotope of iodine, chlorine, bromine, a radioisotope of bromine, a radioisotope of astatine, $NO_2$, $NH_2$, $N^+(R^2)_3$, $Sn(R^2)_3$, $Si(R^2)_3$, $Hg(R^2)$, $B(OH)_2$, —$NHNH_2$, —NHN═$CHR^3$, —NHNH—$CH_2R^3$. $R^2$ is $C_1$-$C_6$ alkyl; and $R^3$ is alkyl, alkenyl, alkynyl, aryl, or heteroaryl each of which is substituted by fluorine, iodine, a radioisotope of fluorine, a radioisotope of iodine, chlorine bromine, a radioisotope of bromine, or a radioisotope of astatine; $NO_2$, $NH_2$, $N^+(R^2)_3$, $Sn(R^2)_3$, $Si(R^2)_3$, $Hg(R^2)$, or $B(OH)_2$. In certain embodiments, n is 1. Other specific embodiments include compounds where X is fluorine, iodine, or a radioisotope of fluorine, a radioisotope of iodine, chlorine, bromine, a radioisotope of bromine, or a radioisotope of astatine. In certain embodiments, $R^3$ is aryl, substituted by fluorine, iodine, a radioisotope of fluorine, a radioisotope of iodine, bromine, a radioisotope of bromine, or a radioisotope of astatine. Specific embodiments include compounds having the structure shown above, where Z is $CO_2Q$, Q is hydrogen, and m is 1, 2, or 3.

Other embodiments include compounds according to formula I wherein R is the structure below

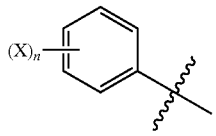

wherein X' is selected from the group consisting of —$NHNH_2$, —NHN═$CHR^3$, —NHNH—$CH_2R^3$. In such embodiments, $R^3$ is alkyl, alkenyl, alkynyl, aryl, or heteroaryl each of which is substituted by fluorine, iodine, a radioisotope of fluorine, a radioisotope of iodine, bromine, a radioisotope of bromine, or a radioisotope of astatine; $NO_2$, $NH_2$, $N^+(R^2)_3$, $Sn(R^2)_3$, $Si(R^2)_3$, $Hg(R^2)$, $B(OH)_2$. $R^2$ is $C_1$-$C_6$ alkyl; and $R^3$ is alkyl, alkenyl, alkynyl, aryl, or heteroaryl each of which is substituted by fluorine, iodine, a radioisotope of fluorine, a radioisotope of iodine, chlorine bromine, a radioisotope of bromine, or a radioisotope of astatine; $NO_2$, $NH_2$, $N^+(R^2)_3$, $Sn(R^2)_3$, $Si(R^2)_3$, $Hg(R^2)$, or $B(OH)_2$. In certain embodiments, $R^3$ is aryl, substituted by fluorine, iodine, a radioisotope of fluorine, a radioisotope of iodine, bromine, a radioisotope of bromine, or a radioisotope of astatine. Specific embodiments include compounds where n is 1.

Compounds according to this embodiment can be prepared, for example, from hydrazine substituted phenyl precursors, followed by derivatization with an alkyl, alkenyl, alkynyl, aryl, or heteroaryl reagent, each of which is substituted by fluorine, iodine, a radioisotope of fluorine, a radioisotope of iodine, chlorine bromine, a radioisotope of bromine, or a radioisotope of astatine $NO_2$, $NH_2$, $N^+(R^2)_3$, $Sn(R^2)_3$, $Si(R^2)_3$, $Hg(R^2)$, and $B(OH)_2$ as illustrated in Scheme 2 below.

Scheme 2

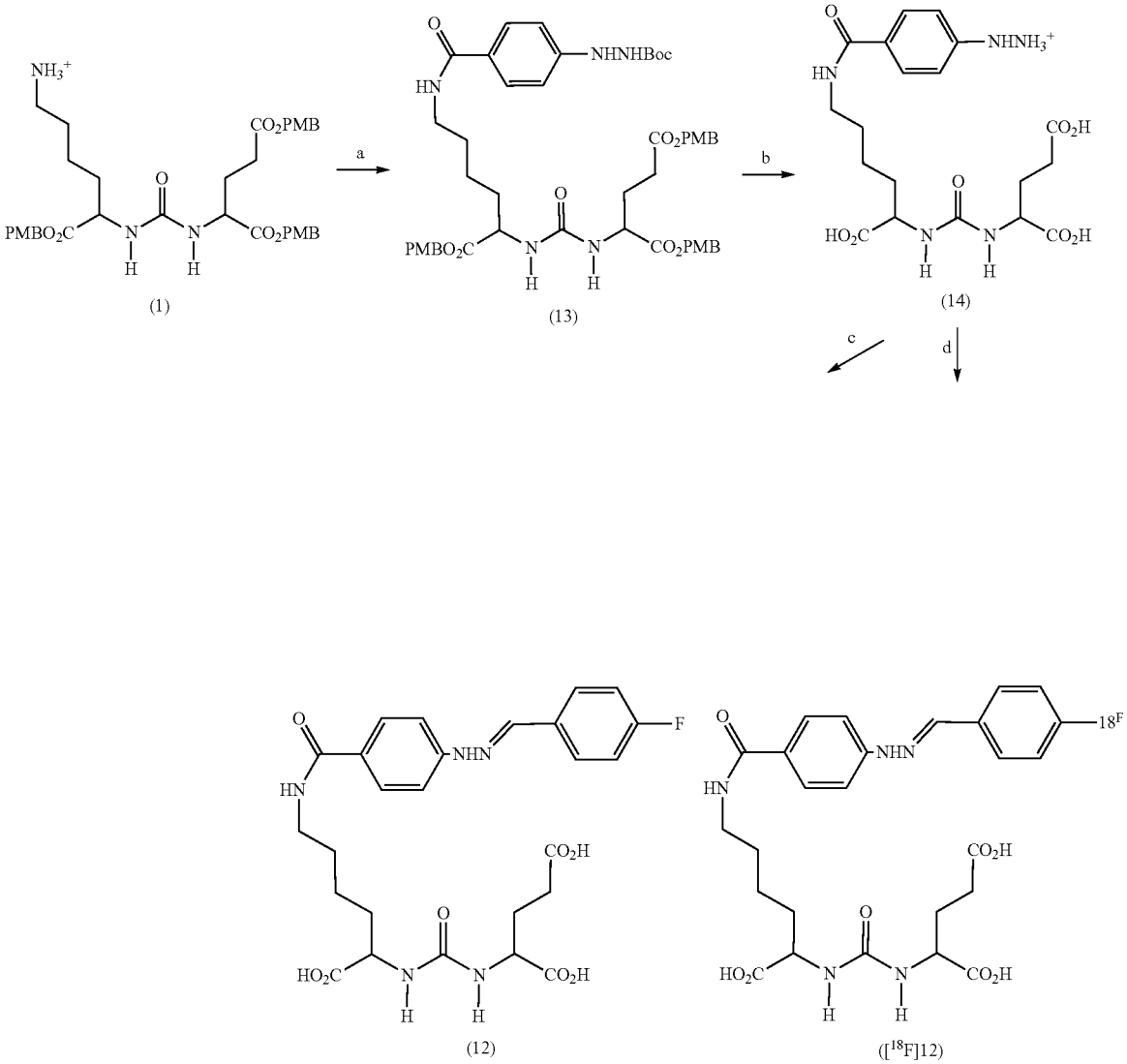

a. succinimidyl 4-[2-(tert-butoxycarbonyl)hydrazino benzoate, triethylamine, DMF, $CH_2Cl_2$;
b. TFA, $CH_2Cl_2$;
c. 4-fluorobenzaldehyde, 50 mM $KH_2PO_4$, $CH_3CN$;
d. 4-[$^{18}$F]fluorobenzaldehyde, 50 mM $KH_2PO_4$.

Other embodiments include compounds according to formula I wherein m is 4, Y is NR', and R is

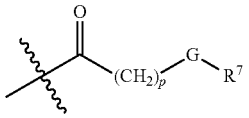

wherein G is O, NR' or a covalent bond, R' is H or $C_1$-$C_6$ alkyl, and p is 1, 2, 3, or 4. $R^7$ can be selected from $NH_2$, N═CHR$^3$, and NH—$CH_2R^3$, wherein $R^3$ is alkyl, alkenyl, alkynyl, aryl, or heteroaryl, each of which is substituted by fluorine, iodine, a radioisotope of fluorine, a radioisotope of iodine, bromine, a radioisotope of bromine, a radioisotope of astatine, $NO_2$, $NH_2$, $N^+(R^2)_3$, $Sn(R^2)_3$, $Si(R^2)_3$, $Hg(R^2)$, or $B(OH)_2$, where $R^2$ is $C_1$-$C_6$ alkyl. In certain embodiments, $R^3$ is aryl, substituted by fluorine, iodine, a radioisotope of fluorine, a radioisotope of iodine, chlorine, bromine, a radioisotope of bromine, or a radioisotope of astatine. In certain embodiments, G is O or NR'.

Compounds according to this embodiment can be prepared, for example, by acylation of PMB protected Lys-C(O)-Glu with an acylating agent bearing a free or protected amine, followed by deprotection of the amine, if necessary, and derivatization with an alkyl, alkenyl, alkynyl, aryl, or heteroaryl reagent, each of which is substituted by fluorine, iodine, a radioisotope of fluorine, a radioisotope of iodine, chlorine, bromine, a radioisotope of bromine, or a radioisotope of astatine, $NO_2$, $NH_2$, $N^+(R^2)_3$, $Sn(R^2)_3$, $Si(R^2)_3$, $Hg(R^2)$, or $B(OH)_2$, as illustrated by Scheme 3 shown below.

Scheme 3

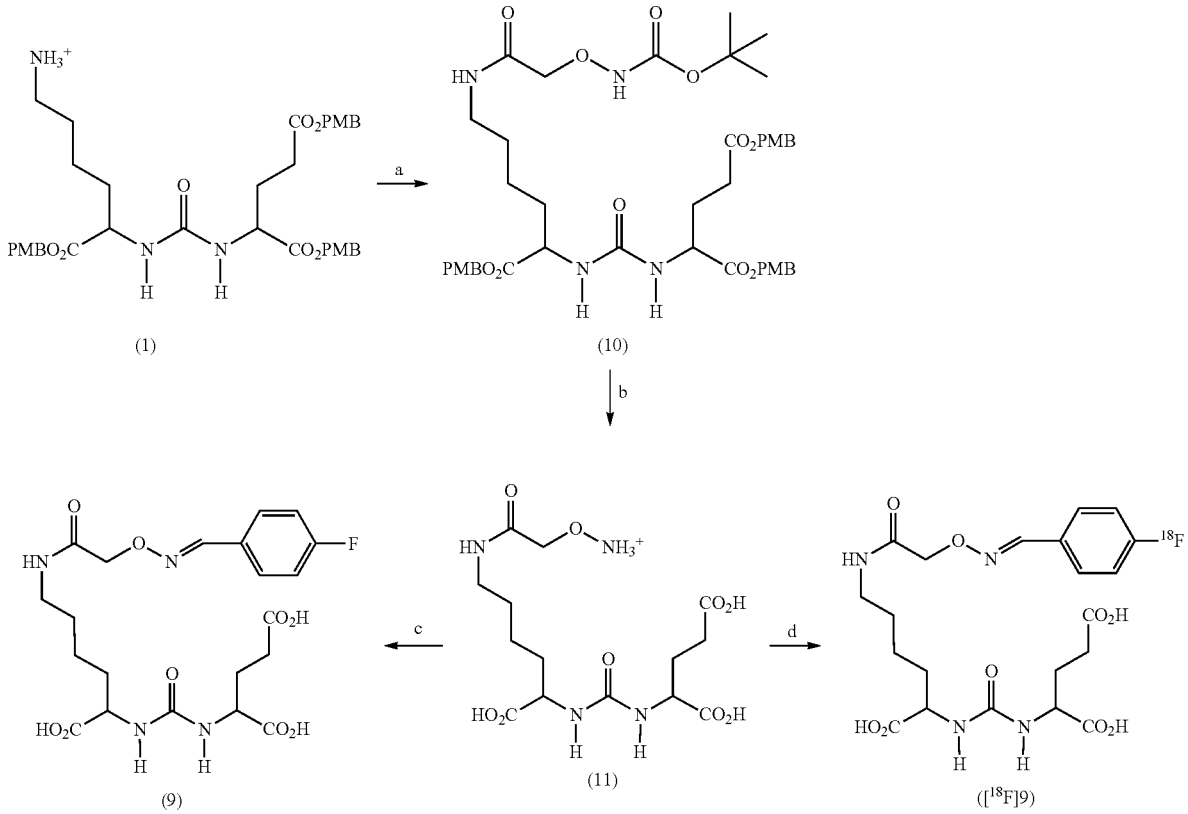

a. N-tert-butoxycarbonyl-O-(carboxymethyl)hydroxyamine hydroxysuccinimidyl ester, triethylamine, $CH_2Cl_2$;

b. TFA, anisole;

c. p-fluorobenzaldehyde, triethylamine, methanol;

d. p-[$^{18}$F]fluorobenzaldehyde, triethylamine, emthanol.

Other embodiments include compounds according to any of the embodiments discussed herein, which comprise a radioisotope. Specific exemplary radioisotopes include $^{18}$F, $^{123}$I, $^{124}$I, $^{125}$I, $^{126}$I, $^{131}$I, $^{75}$Br, $^{76}$Br, $^{77}$Br, $^{80}$Br, $^{80m}$Br, $^{82}$Br, $^{83}$Br and $^{211}$At. Radioisotope containing compounds of any embodiment of the present invention can be prepared with sufficient radiolabel to be used in imaging applications. In other words, the compounds can be prepared with radioisotope concentrations greater than natural abundance, when a particular radioisotope occurs naturally.

Specific examples of compounds according to the previous embodiments include the structures shown below

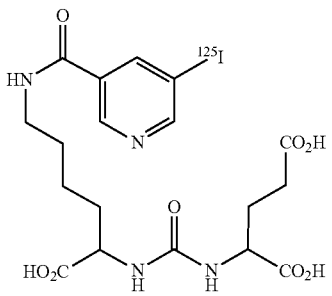

-continued

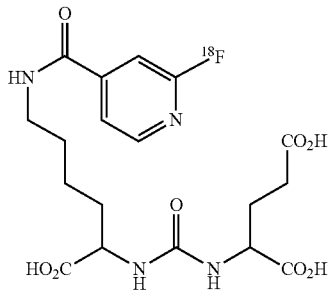

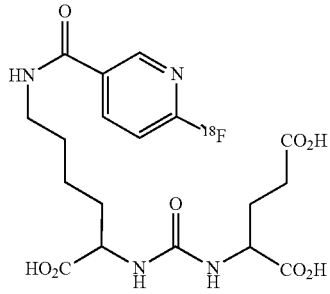

-continued

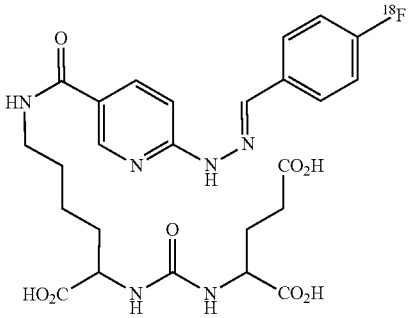

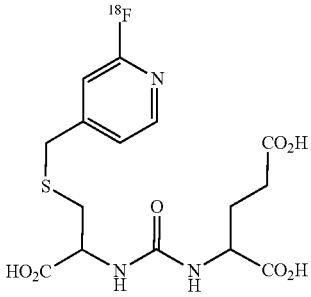

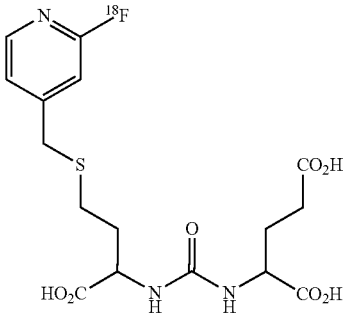

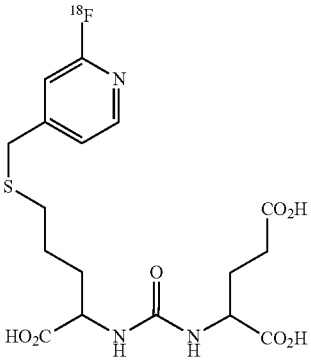

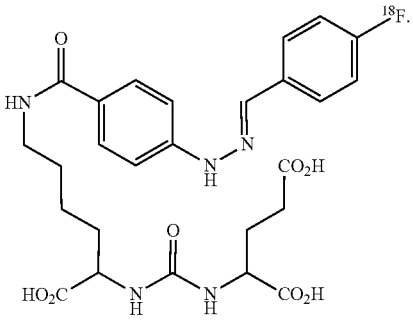

-continued

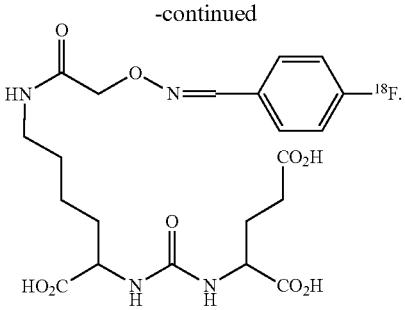

Other embodiments include pharmaceutically acceptable salts of the compounds described in the previous embodiments.

Compounds according to the invention, in particular various radiolabeled compounds, may be used for diagnostic, imaging, or therapeutic purposes. For example, some compounds, e.g. those labeled with $^{125}I$ and $^{123}I$, are designed for SPECT imaging, while some compounds, e.g. those labeled with $^{18}F$ and $^{124}I$, are designed for PET imaging, and some radioisotopically labeled compounds may be used therapeutically. In general, the suitability of a particular radioisotope for a particular purpose is well understood in the art. Other exemplary embodiments are compounds used as precursors for radiolabeled compounds, in which a substituent may be directly exchanged for a radioisotope in one or more steps. Unless described otherwise, the terms "converted," derivatized," "exchanged," or "reacted" are intended to encompass one or more steps. Examples of substituents that may be exchanged for radioisotopes include halogens, $NO_2$, $N^+(R^2)_3$, $Sn(R^2)_3$, $Si(R^2)_3$, $Hg(R^2)$, and $B(OH)_2$. Other compounds are precursors which may be chemically reacted with a radioisotopically labeled reagent to produce a stable radioisotopically labeled compound. Compounds bearing substituents such as halogen, $—NH_2$, $—NHNH_2$, $Sn(R^2)_3$, and $B(OH)_2$, for example, may be converted into radioisotopically labeled compounds by chemical reactions known to those in the art.

Compounds of the present invention may be made by methods known in the art. For example, the asymmetrical ureas used as precursors may be produced by the general scheme shown below, where R is the sidechain of a natural or synthetic amino acid, which bears a group that can be further derivatized. Specific examples of amino acids include lysine, cysteine, homocysteine, serine, threonine, tyrosine, phenylalanine and substituted phenylalanine. Substituted phenylalanine has the structure of phenylalanine where the phenyl sidechain is substituted by, for example, nitro, amino or halogen.

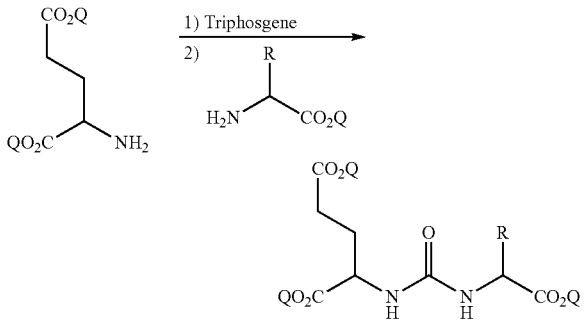

Protected urea precursors Cys-C(O)-Glu, and Lys-C(O)-Glu (shown below), where Q is p-methoxybenzyl (PMB) are used to synthesize exemplary compounds. Preparation of precursor Cys-C(O)-Glu is described, for example by Kozikowski et al. (29), while the preparation of Lys-C(O)-Glu is described, for example, by Banerjee et al. (19).

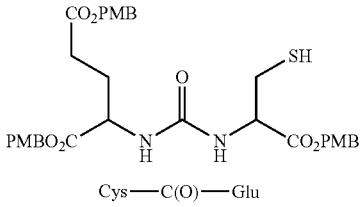

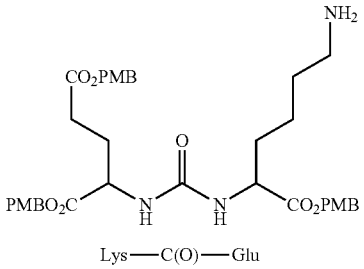

Compounds of the present invention may be prepared, for example, by reaction of a protected urea precursor with a reagent substituted with a radioisotope or other substituent which may be converted or derivatized into a radioisotope containing compound. A protected urea precursor, such as those described above may be reacted, for example with an activated benzoate or pyridine carboxylate. The synthesis of both the halobenzoate and pyridine carboxylate radionuclide-bearing precursors have been described (20)(21)(22)(23)(25)(37)(38).

Pyridinecarboxylate $^{18}F$ precursors, such as n-hydroxysuccinimide-activated pyridine carboxylates, can be prepared, for example, by the scheme shown below.

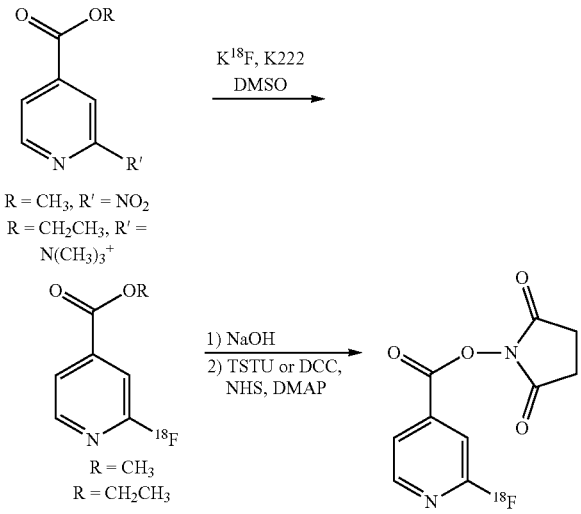

Other $^{18}F$ pyridine precursors may be prepared by methods described by Olberg et al. (J. Labeled Compd. Radiopharm, vol. 52:Supplement 1, p. S160, 2009), shown below.

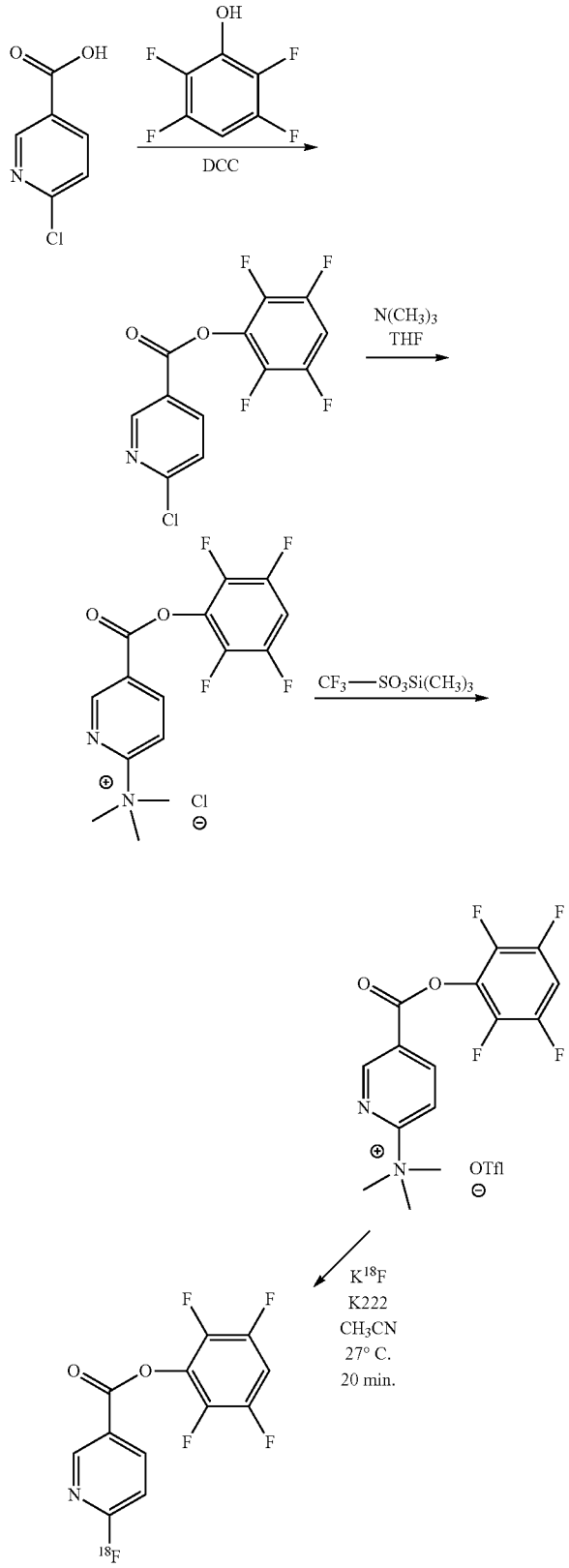

An $^{18}F$ pyridinecarboxylate precursor may be used to prepare compounds according to the present invention, for example, according to the scheme shown below.

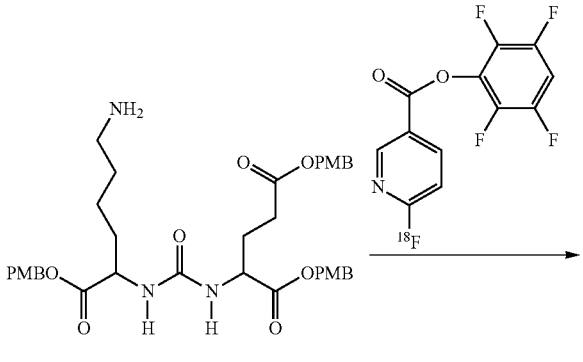

-continued

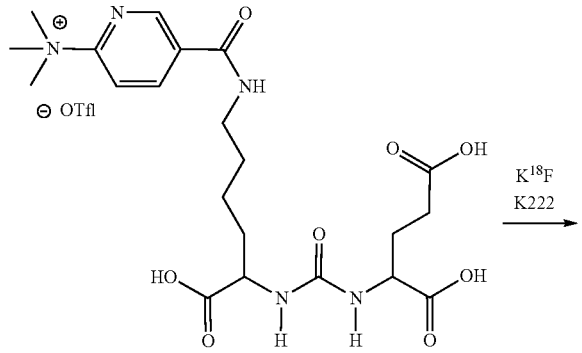

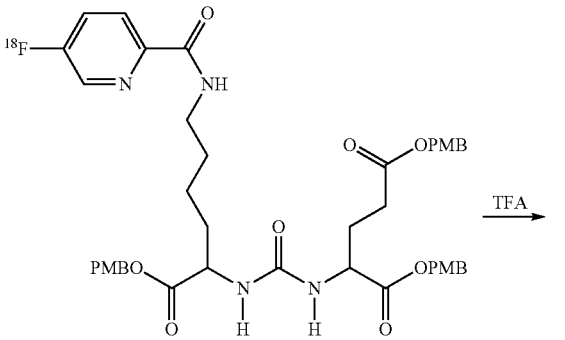

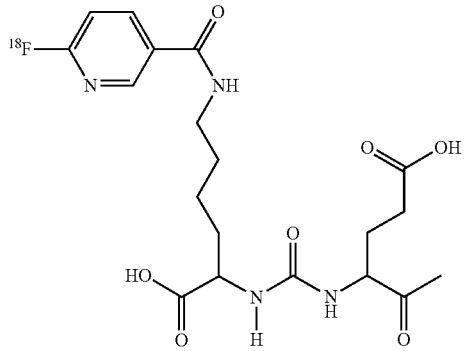

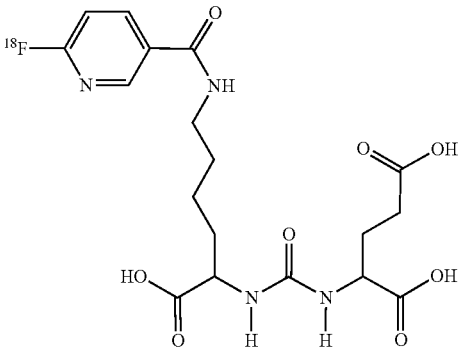

Similarly, a precursor may be prepared, which can then be converted into an $^{18}F$-substituted compound. For example, compounds may be prepared according to the scheme below.

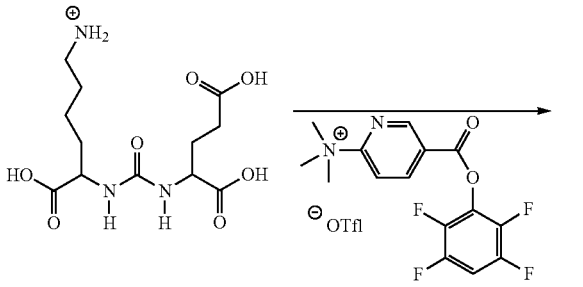

Other compounds may be produced from a suitable protected precursor, such as those discussed above, by reaction with bromomethyl pyridine compounds bearing radioisotope substituents, or substituents which may be converted to radioisotopes or derivatized with radioisotope containing compounds. For example, the scheme below shows preparation of an exemplary compound from PMB protected precursor Cys-C(O)-Glu.

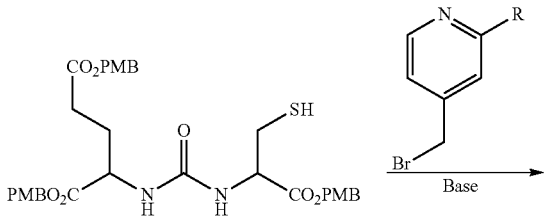

-continued

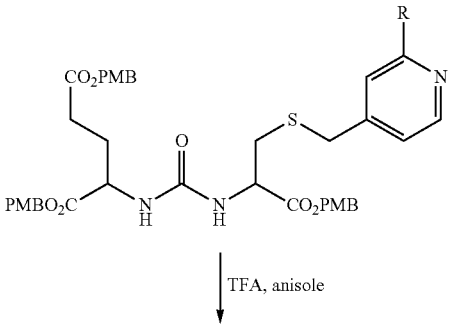

-continued

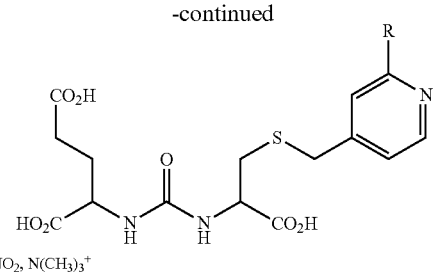

Bromomethyl pyridine compounds, such as $^{18}F$, $NO_2$ or $N(CH_3)_3^+$ substituted bromomethyl pyridine, suitable for preparation of compounds according to the present invention can be prepared, for example, according to the scheme shown below.

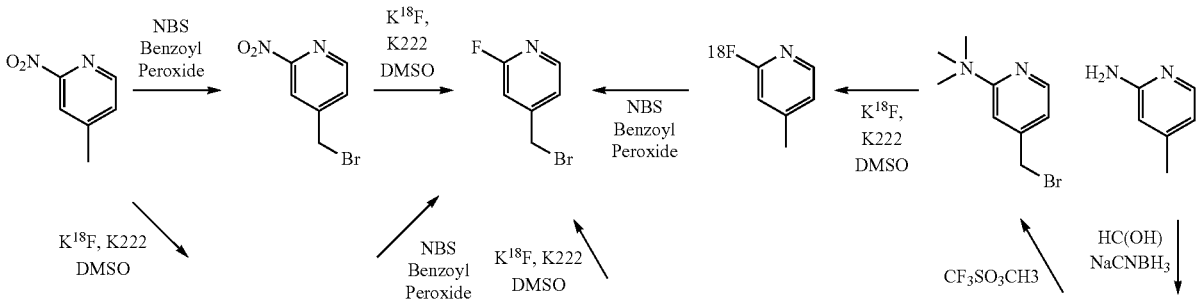

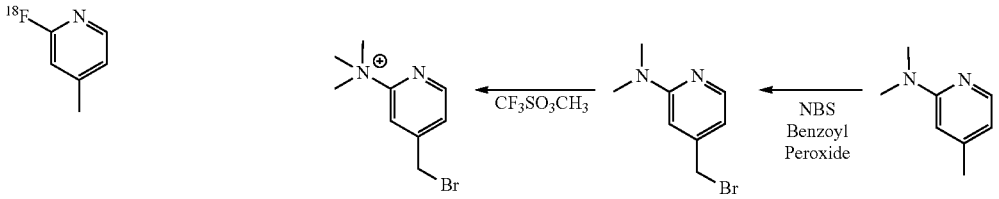

Other compounds can be prepared, for example, from hydrazine (—$NHNH_2$) substituted pyridine precursors, followed by derivatization with an alkyl, alkenyl, alkynyl, aryl, or heteroaryl reagent each of which is substituted by fluorine, iodine, a radioisotope of fluorine, a radioisotope of iodine, chlorine, bromine, a radioisotope of bromine, or a radioisotope of astatine, $NO_2$, $NH_2$, $N^+(R^2)_3$, $Sn(R^2)_3$, $Si(R^2)_3$, $Hg(R^2)$, and $B(OH)_2$. For example, an aldehyde reagent may be reacted with the hydrazine substituent, as illustrated in Scheme 4 shown below. The resulting imine may also be reduced, for example, by sodium cyanoborohydride or other reducing agent, to produce a reduced compound.

Scheme 4

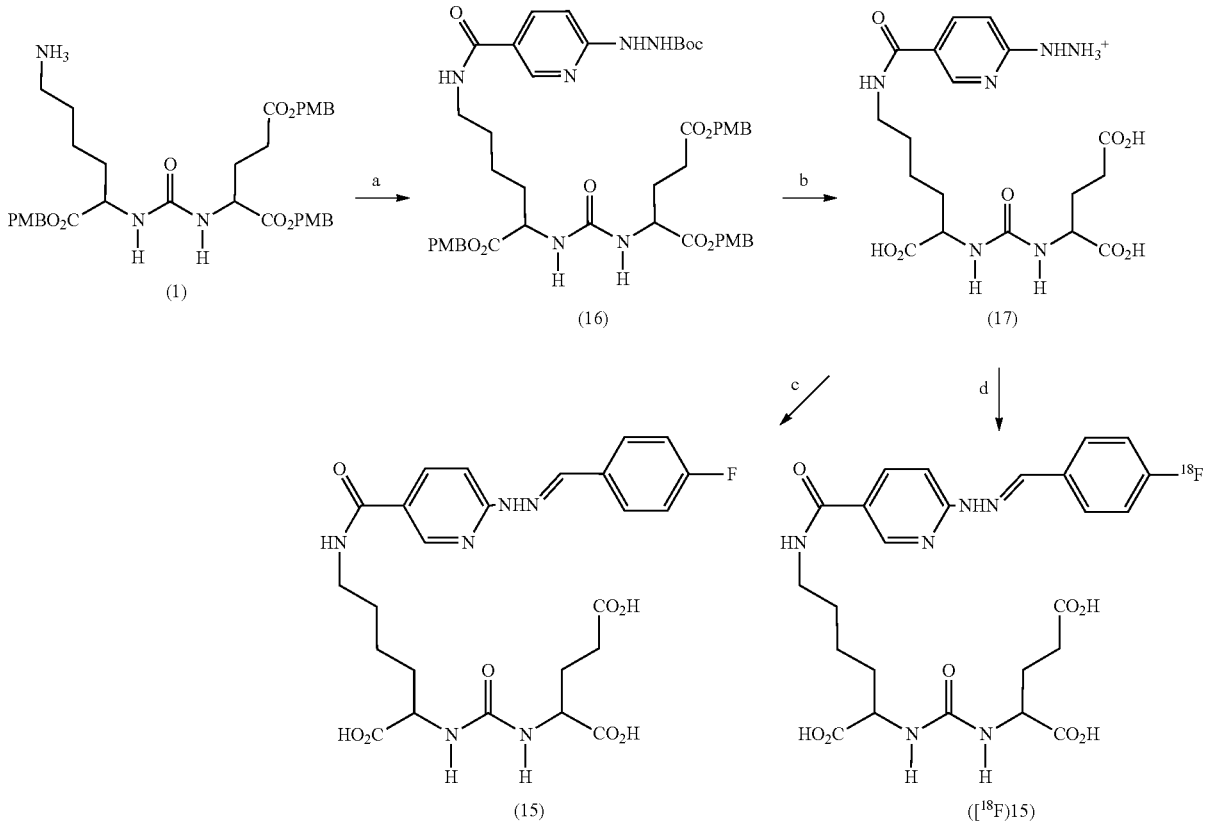

a. succinimidyl 6-(Nε-tert-butoxycarbonyl-hydrazino)-nicotinate. triethylamine, $CH_2Cl_2$;
b. TFA, $CH_2Cl_2$;
c. 4-fluorobenzaldehyde, 50 mM $KH_2PO_4$, $CH_3CN$;
d. 4-[$^{18}$F]fluorobenzaldehyde, 50 mM $KH_2PO_4$.

Other embodiments include compounds having the formula

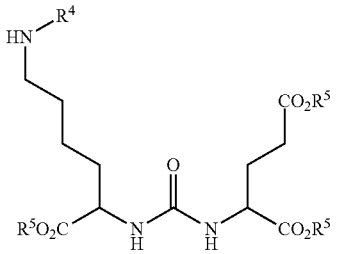

wherein $R^5$ is hydrogen or p-methoxybenzyl; $R^4$ is selected from the group consisting of hydrogen,

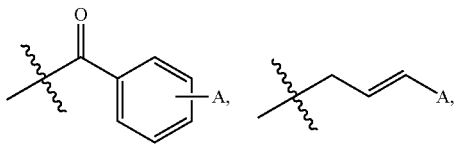

-continued

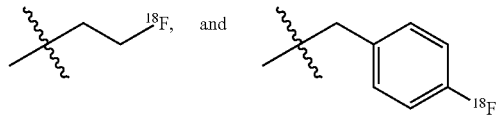

wherein A is fluorine, iodine, a radioisotope of fluorine, a radioisotope of iodine, bromine, a radioisotope of bromine, a radioisotope of astatine, $Sn(R^2)_3$, $Si(R^2)_3$, or HgCl. Further embodiments include compounds according to the structure above, which comprise a radioisotope. One specific embodiment includes the compound having the formula shown below, also known as PMB protected Lys-C(O)-Glu.

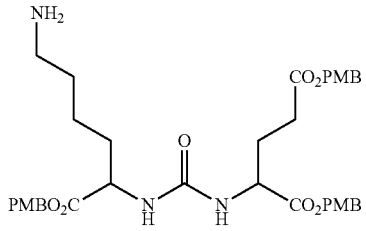

wherein PMB is p-methoxybenzyl. Another specific embodiment includes the compound 2-[3-(5-amino-1-carboxy-pentyl)-ureido]-pentanedioic acid, also known as Lys-C(O)-Glu. Other exemplary embodiments include compounds shown below.

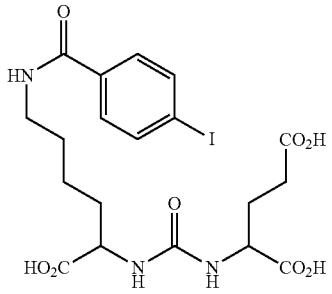

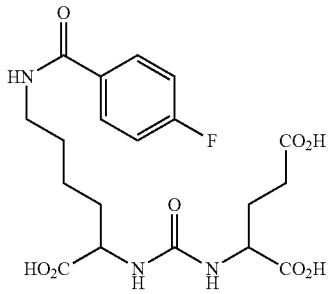

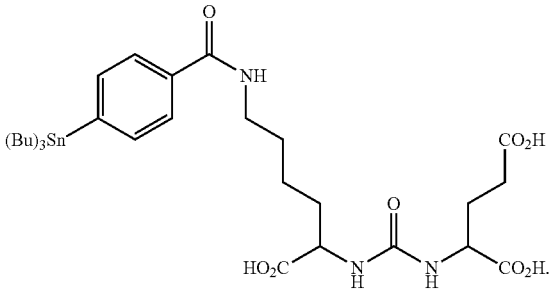

Exemplary radioisotope containing compounds include the compounds shown below.

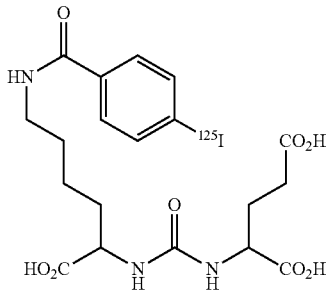

-continued

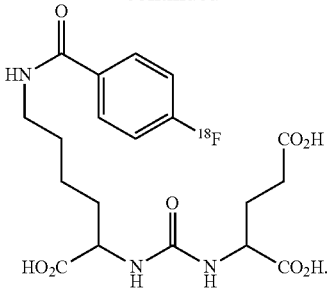

Other embodiments of the inventions include methods of imaging one or more cells, organs or tissues comprising exposing cells to or administering to a subject an effective amount of a compound with an isotopic label suitable for imaging. In some embodiments, the one or more organs or tissues include prostate tissue, kidney tissue, brain tissue, vascular tissue or tumor tissue.

In another embodiment, the imaging method is suitable for imaging studies of PSMA inhibitors, for example, by studying competitive binding of non-radiolabeled inhibitors. In still another embodiment, the imaging method is suitable for imaging of cancer, tumor or neoplasm. In a further embodiment, the cancer is selected from eye or ocular cancer, rectal cancer, colon cancer, cervical cancer, prostate cancer, breast cancer and bladder cancer, oral cancer, benign and malignant tumors, stomach cancer, liver cancer, pancreatic cancer, lung cancer, corpus uteri, ovary cancer, prostate cancer, testicular cancer, renal cancer, brain cancer (e.g., gliomas), throat cancer, skin melanoma, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, and lymphangiogenesis.

The imaging methods of the invention are suitable for imaging any physiological process or feature in which PSMA is involved. Typically, imaging methods are suitable for identification of areas of tissues or targets which express high concentrations of PSMA. Typical applications include imaging glutamateric neurotransmission, presynaptic glutamatergic neurotransmission, malignant tumors or cancers that express PSMA, prostate cancer (including metastasized prostate cancer), and angiogenesis. Essentially all solid tumors express PSMA in the neovasculture. Therefore, methods of the present invention can be used to image nearly all solid tumors including lung, renal cell, glioblastoma, pancreas, bladder, sarcoma, melanoma, breast, colon, germ cell, pheochromocytoma, esophageal and stomach. Also, certain benign lesions and tissues including endometrium, schwannoma and Barrett's esophagus can be imaged according to the present invention.

The methods of imaging angiogenesis provided by the present invention are suitable for use in imaging a variety of diseases and disorders in which angiogenesis takes place. Illustrative, non-limiting, examples include tumors, collagen vascular disease, cancer, stroke, vascular malformations, retinopathy. Methods of imaging angiogenesis provided by the present invention are also suitable for use in diagnosis and observation of normal tissue development.

PSMA is frequently expressed in endothelial cells of capillary vessels in peritumoral and endotumoral areas of various malignancies such that compounds of the invention and methods of imaging using same are suitable for imaging such malignancies.

In certain embodiments, the radiolabeled compound is stable in vivo.

In certain embodiments, the radiolabeled compound is detected by positron emission tomography (PET) or single photon emission computed tomography (SPECT).

In one embodiment, the invention provides a method wherein the subject is a human, rat, mouse, cat, dog, horse, sheep, cow, monkey, avian, or amphibian. In another embodiment, the cell is in vivo or in vitro. Typical subjects to which compounds of the invention may be administered will be mammals, particularly primates, especially humans. For veterinary applications, a wide variety of subjects will be suitable, e. g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids and cell samples of the above subjects will be suitable for use such as mammalian, particularly primate such as human, blood, urine or tissue samples, or blood urine or tissue samples of the animals mentioned for veterinary applications.

In certain methods of the invention the compounds of the invention are excreted from tissues of the body quickly to prevent prolonged exposure to the radiation of the radiolabeled compound administered to the patient. Typically compounds of the invention are eliminated from the body in less than about 24 hours. More typically, compounds of the invention are eliminated from the body in less than about 16 hours, 12 hours, 8 hours, 6 hours, 4 hours, 2 hours, 90 minutes, or 60 minutes. Exemplary compounds are eliminated in between about 60 minutes and about 120 minutes.

In some embodiments, the compounds bind strongly to the PSMA protein, for instance by incorporating structural features which reside in an accessory binding site. For example, in compound 3, the 4-iodobenzoyl group resides in a hydrophobic pocket accessory to the Si binding site (39).

In certain embodiments, compounds of the invention are stable in vivo such that substantially all, e.g., more than about 50%, 60%, 70%, 80%, or 90% of the injected compound is not metabolized by the body prior to excretion. Typical subjects to which compounds of the invention may be administered will be mammals, particularly primates, especially humans. For veterinary applications, a wide variety of subjects will be suitable, e.g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids and cell samples of the above subjects will be suitable for use such as mammalian, particularly primate such as human, blood, urine or tissue samples, or blood urine or tissue samples of the animals mentioned for veterinary applications.

Other embodiments of the invention provide methods of treating tumors comprising administering to a subject a therapeutically effective amount of a compound according to the present invention comprising a therapeutically effective radioisotope. In certain embodiments, the tumor cells may express PSMA, such as prostate tumor cells or metastasized prostate tumor cells. In other embodiments, a tumor may be treated by targeting adjacent or nearby cells which express PSMA. For example, vascular cells undergoing angiogenesis associated with a tumor may be targeted. Essentially all solid tumors express PSMA in the neovasculture. Therefore, methods of the present invention can be used to treat nearly all solid tumors including lung, renal cell, glioblastoma, pancreas, bladder, sarcoma, melanoma, breast, colon, germ cell, pheochromocytoma, esophageal and stomach. Also, certain benign lesions and tissues including endometrium, schwannoma and Barrett's esophagus can be treated according to the present invention. Examples of therapeutically effective radioisotopes include $^{131}$I and $^{211}$At.

Other embodiments provide kits comprising a compound according to the invention. In certain embodiments, the kit provides packaged pharmaceutical compositions comprising a pharmaceutically acceptable carrier and a compound of the invention. In certain embodiments the packaged pharmaceutical composition will comprise the reaction precursors necessary to generate the compound of the invention upon combination with a radiolabeled precursor. Other packaged pharmaceutical compositions provided by the present invention further comprise indicia comprising at least one of: instructions for preparing compounds according to the invention from supplied precursors, instructions for using the composition to image cells or tissues expressing PSMA, or instructions for using the composition to image glutamatergic neurotransmission in a patient suffering from a stress-related disorder, or instructions for using the composition to image prostate cancer.

In certain embodiments, a kit according to the invention contains from about 1 to about 30 mCi of the radionuclide-labeled imaging agent described above, in combination with a pharmaceutically acceptable carrier. The imaging agent and carrier may be provided in solution or in lyophilized form. When the imaging agent and carrier of the kit are in lyophilized form, the kit may optionally contain a sterile and physiologically acceptable reconstitution medium such as water, saline, buffered saline, and the like. The kit may provide a compound of the invention in solution or in lyophilized form, and these components of the kit of the invention may optionally contain stabilizers such as NaCl, silicate, phosphate buffers, ascorbic acid, gentisic acid, and the like. Additional stabilization of kit components may be provided in this embodiment, for example, by providing the reducing agent in an oxidation-resistant form. Determination and optimization of such stabilizers and stabilization methods are well within the level of skill in the art.

In certain embodiments, a kit provides a non-radiolabeled precursor to be combined with a radiolabeled reagent on-site. Examples of radioactive reagents include Na[$^{125}$I], Na[$^{131}$I], Na[$^{123}$I], Na[$^{124}$I], K[$^{18}$F], Na[$^{76}$Br], Na[$^{75}$Br], Na[$^{211}$At]. Other radiolabeled reagents include activated radiolabeled benzoyl compounds, radiolabeled pyridine carboxylates, radiolabeled bromomethyl pyridine compounds, and radiolabeled aldehydes discussed previously.

Imaging agents of the invention may be used in accordance with the methods of the invention by one of skill in the art. Images can be generated by virtue of differences in the spatial distribution of the imaging agents which accumulate at a site when contacted with PSMA. The spatial distribution may be measured using any means suitable for the particular label, for example, a gamma camera, a PET apparatus, a SPECT apparatus, and the like. The extent of accumulation of the imaging agent may be quantified using known methods for quantifying radioactive emissions. A particularly useful imaging approach employs more than one imaging agent to perform simultaneous studies.

In general, a detectably effective amount of the imaging agent of the invention is administered to a subject. In accordance with the invention, "a detectably effective amount" of the imaging agent of the invention is defined as an amount sufficient to yield an acceptable image using equipment which is available for clinical use. A detectably effective amount of the imaging agent of the invention may be administered in more than one injection. The detectably effective amount of the imaging agent of the invention can vary according to factors such as the degree of susceptibility of the individual, the age, sex, and weight of the individual, idiosyncratic responses of the individual, and the dosimetry. Detectably effective amounts of the imaging agent of the invention can also vary according to instrument and film-related factors. Optimization of such factors is well within the level of skill in the art. The amount of imaging agent used for diagnostic purposes and the duration of the imaging study will depend upon the radionuclide used to label the agent, the body mass of the patient, the nature and severity of the condition being treated, the nature of therapeutic treatments which the patient has undergone, and on the idiosyncratic responses of the patient. Ultimately, the attending physician will decide the amount of imaging agent to administer to each individual patient and the duration of the imaging study.

A "pharmaceutically acceptable carrier" refers to a biocompatible solution, having due regard to sterility, p[Eta], isotonicity, stability, and the like and can include any and all solvents, diluents (including sterile saline, Sodium Chloride Injection, Ringer's Injection, Dextrose Injection, Dextrose and Sodium Chloride Injection, Lactated Ringer's Injection and other aqueous buffer solutions), dispersion media, coatings, antibacterial and antifungal agents, isotonic agents, and the like. The pharmaceutically acceptable carrier may also contain stabilizers, preservatives, antioxidants, or other additives, which are well known to one of skill in the art, or other vehicle as known in the art.

As used herein, "pharmaceutically acceptable salts" refer to derivatives of the disclosed compounds wherein the parent compound is modified by making non-toxic acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, malefic, hydroxymaleic, phenylacetic, glutamic, benzoic, salicylic, mesylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. The pharmaceutically acceptable salts of the present invention can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are used, where practicable. Lists of additional suitable salts may be found, e.g., in Remington's Pharmaceutical Sciences, 17th ed., Mack Publishing Company, Easton, Pa., p. 1418 (1985).

The contents of all cited references (including literature references, issued patents, published patent applications) as cited throughout this application are hereby expressly incorporated by reference. The invention and the manner and process of making and using it, are described in such full, clear, concise and exact terms as to enable any person skilled in the art to which it pertains, to make and use the same.

It is to be understood that the foregoing describes exemplary embodiments of the present invention and that modifications may be made therein without departing from the spirit or scope of the present invention as set forth in the appended claims.

EXAMPLES

The present invention is further illustrated by the following examples which should not be construed as limiting in any way. The practice of the present invention will employ, unless otherwise indicated, conventional techniques, which are within the skill of the art. Such techniques are explained fully in the literature.

Synthesis

General Procedures.

All reagents and solvents were purchased from either Sigma-Aldrich (Milwaukee, Wis.) or Fisher Scientific (Pittsburgh, Pa.). The tosylate salt of PMB-protected Lys-C(O)-Glu (compound 1) was prepared according to a reported procedure (19). $^1$H NMR spectra were obtained on a Varian Mercury 400 mHz or a Bruker Avance 400 mHz Spectrometer. ESI mass spectra were obtained on an API 15OEX™ or a Bruker Esquire 3000 plus system. High-resolution mass spectra (HRMS) were performed on a JEOL JMS-AX505HA mass spectrometer in the Mass Spectrometry Facility at the University of Notre Dame. HPLC purification of reference compounds was performed on a Waters 625 LC system with a Waters 490E multiwavelength UV/Vis detector (Milford, Mass.).

[$^{125}$I]NaI was purchased from MP Biomedicals (Costa Mesa, Calif.). [$^{18}$F]Fluoride was produced by 18 MeV proton bombardment of a high pressure [$^{18}$O]$H_2O$ target using a General Electric PETtrace biomedical cyclotron (Milwaukee, Wis.). Solid-phase extraction cartridges ($C_{18}$ plus, Sep-Pak) were purchased from Waters Associates. Radioactivity was measured in a Capintec CRC-10R dose calibrator (Ramsey, N.J.). The specific radioactivity was calculated as the radioactivity eluting at the retention time of product during the semi-preparative HPLC purification divided by the mass corresponding to the area under the curve of the UV absorption.

Example 1

2-{3-[5-(4-Iodo-benzoylamino)-1-(4-methoxy-benzyloxycarbonyl)-pentyl]-ureido}-pentanedioic acid bis-(4-methoxy-benzyl)ester (2)

To a solution of 1 (0.126 g, 0.148 mmol) in $CH_2Cl_2$ (4 mL) was added triethylamine (0.1 mL, 0.712 mmol), followed by N-hydroxysuccinimidyl-4-iodobenzoate (24) (0.073 g, 0.212 mmol). After stirring for 2 h at room temperature, the solvent was evaporated on a rotary evaporator. The crude material was purified on a silica column using methanol/methylene chloride (5:95) to afford 0.127 g (94%) of 2. $^1$H NMR (400 MHz, $CDCl_3$) δ 7.69 (d, J=8.8 Hz, 2H), 7.49 (d, J=8.8 Hz, 2H), 7.17-7.26 (m, 6H), 6.77-6.86 (m, 7H), 5.37-5.46 (m, 2H), 4.93-5.09 (m, 6H), 4.32-4.40 (m, 2H), 3.76-3.77 (m, 9H), 3.30-3.33 (m, 2H), 2.30-2.36 (m, 2H), 2.07-2.12 (m, 1H), 1.84-1.92 (m, 1H), 1.70-1.79 (m, 1H), 1.49-1.57 (m, 3H), 1.25-1.33 (m, 2H). ESI-Mass calcd for $C_{43}H_{48}IN_3O_{11}Na$ $[M+Na]^+$ 932.2, found 932.7.

Example 2

2-{3-[1-Carboxy-5-(4-iodo-benzoylamino)-pentyl] ureido}-pentanedioic acid (3)

A solution of 3% anisole in TFA (15 mL) was added to 2 (0.117 g, 0.129 mmol) at 0° C. The mixture was stirred at room temperature for 30 min then concentrated on a rotary evaporator. The crude material was purified by HPLC (Econosil C18 10μ, 250×10 mm, $H_2O/CH_3CN$/TFA (70/30/0.1), 4 mL/min, 3 eluting at 11 min) to afford 0.040 g (57%) of 3. $^1$H NMR (400 MHz, $D_2O$:$CD_3CN$=1:1 (v/v)) δ 7.79 (d, J=8.0 Hz, 2H), 7.46 (d, J=8.0 Hz, 2H), 4.08-4.16 (m, 2H), 3.26 (m, 2H), 2.35 (m, 2H), 2.00-2.03 (m, 1H), 1.72-1.84 (m, 2H), 1.52-1.62 (m, 3H), 1.34-1.36 (m, 2H). ESI-Mass calcd for $C_{19}H_{24}IN_3O_8Na$ $[M+Na]^+$ 572.1. found 572.0. FAB-HRMS calcd for $C_{19}H_{25}IN_3O_8$ $[M+H]^+$ 550.0686. found 550.0648.

Example 3

2-{3-[1-(4-Methoxy-benzyloxycarbonyl)-5-(4-tributylstannanyl-benzoylamino)-pentyl]-ureido}-pentanedioic acid bis-(4-methoxy-benzyl)ester (4)

To a solution of 1 (0.120 g, 0.148 mmol) in $CH_2Cl_2$ (6 mL) was added triethylamine (0.1 ml, 0.712 mmol), followed by N-hydroxysuccinimidyl-4-tributylstannylbenzoate (24) (0.075 g, 0.147 mmol). After stirring for 2 h at room temperature, the reaction mixture was condensed on a rotary evaporator. The crude material was purified on a silica column using methanol/methylene chloride (5:95) to afford 0.130 g (86%) of 4. $^1$H NMR (400 MHz, $CDCl_3$) δ 7.68 (d, J=8.4 Hz, 2H), 7.49 (d, J=7.6 Hz, 2H), 7.18-7.24 (m, 6H), 6.80-6.85 (m, 6H), 6.47 (m, 1H), 5.44-5.47 (m, 2H), 4.95-5.09 (m, 6H), 4.41-4.45 (m, 2H), 3.76-3.77 (m, 9H), 3.32-3.38 (m, 2H), 2.35-2.37 (m, 2H), 2.08-2.16 (m, 1H), 1.90-1.94 (m, 1H), 1.70-1.79 (m, 1H), 1.45-1.64 (m, 9H), 1.24-1.30 (m, 8H), 1.01-1.06 (m, 6H), 0.85-0.87 (m, 9H). ESI-Mass calcd for $C_{55}H_{75}N_3O_{11}SnNa$ $[M+Na]^+$ 1096.4. found 1096.7.

Example 4

2-{3-[5-(4-Fluoro-benzoylamino)-1-(4-methoxy-benzyloxycarbonyl)-pentyl]-ureido}-pentanedioic acid bis-(4-methoxy-benzyl)ester (5)

To a solution of 1 (0.120 g, 0.164 mmol) in $CH_2Cl_2$ (4 mL) was added triethylamine (0.1 mL, 0.712 mmol), followed by N-hydroxysuccinimidyl-4-fluorobenzoate (22) (0.043 g, 0.181 mmol). After stirring for 2 h at room temperature, the solvent was evaporated on a rotary evaporator. The crude material was purified by on a silica column using methanol/methylene chloride (5:95) to afford 0.120 g (91%) of 5. $^1$H NMR (400 MHz, $CDCl_3$) δ 7.78 (m, 2H), 7.16-7.24 (m, 6H), 7.01 (m, 2H), 6.80-6.85 (m, 7H), 5.51-5.64 (m, 2H), 4.93-5.09 (m, 6H), 4.34-4.40 (m, 2H), 3.75-3.77 (m, 9H), 3.28-3.34 (m, 2H), 2.26-2.38 (m, 2H), 2.04-2.15 (m, 1H), 1.82-1.91 (m, 1H), 1.68-1.74 (m, 1H), 1.44-1.57 (m, 3H), 1.25-1.33 (m, 2H). ESI-Mass calcd for $C_{43}H_{48}FN_3O_{11}Na$ $[M+Na]^+$ 824.3. found 824.7.

Example 5

2-{3-[1-Carboxy-5-(4-fluoro-benzoylamino)-pentyl]-ureido}-pentanedioic acid (6)

A solution of 3% anisole in TFA (15 mL) was added to 5 (0.081 g, 0.1 mmol) at 0° C. The mixture was stirred at room temperature for 20 min then concentrated on a rotary evaporator. The crude material was purified by HPLC (Econosil C18 10 μm, 250×10 mm, $H_2O/CH_3CN$/TFA (75/25/0.1), 4 mL/min, with purified 6 eluting at about 9 min) to afford 0.035 g (79%) of 6. $^1$H-NMR (400 MHz, $D_2O$) δ 7.66-7.69 (m, 2H), 7.11-7.16 (m, 2H), 4.12-4.19 (m, 2H), 3.28-3.31 (m, 2H), 2.39-2.43 (m, 2H), 2.07-2.09 (m, 1H), 1.79-1.90 (m, 2H), 1.55-1.69 (m, 3H), 1.39-1.40 (m, 2H). ESI-Mass calcd for $C_{19}H_{24}FN_3O_8Na$ $[M+Na]^+$ 464.1. found 464.4. FAB-HRMS calcd for $C_{19}H_{25}FN_3O_8$ $[M+H]^+$ 442.1626. found 442.1646.

Example 6

2-(3-{1-(4-methoxy-benzyloxycarbonyl)-5-[(5-tributylstannanyl-pyridine-3-carbonyl)-amino]-pentyl}-ureido)-pentanedioic acid bis-(4-methoxy-benzyl) ester (7)

To a solution of 1(0.120 g, 0.148 mmol) in $CH_2Cl_2$ (2 mL) was added triethylamine (0.1 mL, 0.712 mmol), followed by N-hydroxysuccinimidyl-5-(tri-n-butylstannyl)-3-pyridinecarboxylate (25) (0.075 g, 0.147 mmol). After stirring for 30 min at room temperature, the crude material was purified on a silica column using methanol/methylene chloride (5:95) to afford 0.115 g (76%) of 7. $^1$H NMR (400 MHz, $CDCl_3$) δ 8.85 (s, 1H), 8.65 (s, 1H), 8.19 (s, 1H), 7.19-7.24 (m, 6H), 6.81-6.85 (m, 6H), 6.65 (m, 1H), 5.32-5.35 (m, 1H), 5.22-5.25 (m, 1H), 4.96-5.10 (m, 6H), 4.40-4.47 (m, 2H), 3.70-3.77 (m, 9H), 3.34 (m, 2H), 2.35-2.39 (m, 2H), 2.10-2.15 (m, 1H), 1.90-1.94 (m, 1H), 1.72-1.79 (m, 1H), 1.46-1.59 (m, 9H), 1.27-1.36 (m, 8H), 1.02-1.25 (m, 6H), 0.84-0.87 (m, 9H). ESI-Mass calcd for $C_{54}H_{75}IN_4O_{11}Sn$ $[M+H]^+$ 1075.4. found 1075.5.

Example 7

2-(3-{1-carboxy-5-[(5-iodo-pyridine-3-carbonyl)-amino]-pentyl}-ureido)-pentanedioic acid (8)

To a solution of 7 (0.025 g, 0.023 mmol) in 2 mL methanol was added 0.020 mL acetic acid and sodium iodide (0.017 g, 0.113 mmol), followed by N-chlorosuccinimide (0.025 g, 0.187 mmol). After 20 min at room temperature, the solvent was removed under a stream of nitrogen. A solution of TFA in $CH_2Cl_2$ (1:1, 2 mL) was then added to the residue. After 1 h at room temperature, 8 (0.008 g, 62%) was isolated by HPLC (Econosphere C18 10μ., 250×10 mm, $H_2O/CH_3CN$/TFA (85/15/0.1), 4 mL/min, product peak eluting at 10 min). $^1$H NMR (400 MHz, $D_2O$) δ 9.00-9.15 (m, 3H), 4.18-4.24 (m, 2H), 3.40-3.41 (m, 2H), 2.45-2.49 (m, 2H), 2.12-2.13 (m, 1H), 1.85-1.97 (m, 2H), 1.64-1.73 (m, 3H), 1.44 (m, 2H). ESI-Mass calcd for $C_{18}H_{24}IN_4O_8$ $[M+H]^+$ 551.1. found 551.0. FAB-HRMS calcd for $C_{18}H_{24}IN_4O_8$ $[M+H]^+$ 551.0639. found 551.0607.

Example 8

2-{3-[1-carboxy-5-(4-[$^{125}$I]iodo-benzoylamino)-pentyl]-ureido}-pentanedioic acid ([$^{125}$I]3)

[$^{125}$I]3 was prepared via iododestannylation of the corresponding tri-n-butylstannyl precursor 4 followed by deprotection. To a solution of 4 (1 mg, 0.932 μmol) in 0.1 mL methanol was added 0.001 mL acetic acid and [$^{125}$I]NaI, followed by N-chlorosuccinimide (0.25 mg, 0.187 μmol) in 0.025 mL of methanol. After stirring at room temperature for 20 min, the solvent was removed under a stream of $N_2$. A solution of 3% anisole in TFA (0.1 mL) was then added to the residue. After 5 min at room temperature, [$^{125}$I]3 was isolated by HPLC (Econosil C18 10μ., 250×4.6 mm, $H_2O/CH_3CN$/TFA (72/28/0.1), 1 mL/min). Reverse phase radio-HPLC purification of [$^{125}$I]3 was performed using a Waters 510 pump, Waters 490E variable wavelength UV/Vis detector at 254 nm and a Bioscan Flow Count PMT radioactivity detector (Washington, D.C.). The yields of this reaction were 65-80% (three separate determinations). Specific radioactivity was always >700 Ci/mmol (25.9 GBq/μmol).

Example 9

N-Hydroxysuccinimidyl-4-[$^{18}$F]fluorobenzoate [$^{18}$F] SFB

N-hydroxysuccinimidyl-4-[$^{18}$F]iodobenzoate ([$^{18}$F]SFB) was prepared by a literature procedure (23) and purified by HPLC (Econosphere C18 10μ, 250×10 mm, $H_2O/CH_3CN$/TFA (75/25/0.1), 5 mL/min, product peak eluting at 19 min).

2-{3-[1-carboxy-5-(4-[$^{18}$F]fluoro-benzoylamino)-pentyl]-ureido}-pentanedioic acid ([$^{18}$F]6)

In a vial containing 2 mg of 1 and 0.002 mL of $Et_3N$ was added [$^{18}$F]SFB in $CH_2Cl_2$. The reaction mixture was heated at 45° C. for 20 min, and then the solvent was removed under a stream of nitrogen. 0.1 mL of 3% anisole/TFA was then added and the reaction mixture was heated at 45° C. for 5 min. The final product ([$^{18}$F]6) was obtained after HPLC purification (Econosphere C18 10μ., 250×10 mm, $H_2O/CH_3CN$/TFA [80/20/0.1], 4 mL/min). The decay-corrected yields of [$^{18}$F]6 were 30-35%, based on starting [$^{18}$F] fluoride (three separate determinations). The mean synthesis time was 180 min from the time of addition of [$^{18}$F]fluoride. Starting from 40 mCi [$^{18}$F]fluoride, the specific radioactivity of [$^{18}$F]6 was found to be 250-300 Ci/mmol (9.1-11.1 GBq/μmol).

Example 10

2-(3-{1-carboxy-5-[(5-[$^{125}$I]iodo-pyridine-3-carbonyl)-amino]pentyl}-ureido)-pentanedioic acid ([$^{125}$I] 8)

[$^{125}$I]8 as prepared using iododestannylation of the corresponding tri-n-butylstannyl precursor 7 followed by deprotection. To a solution of 7 (0.05 mg, 0.047 μmol) in 0.05 mL of methanol was added 0.002 mL acetic acid, [$^{125}$I]NaI, followed by N-chlorosuccinimide (0.1 mg, 0.749 μmol) in 0.010 mL of methanol. After 20 min at room temperature, the solvent was removed under a stream of nitrogen. A solution of 3% anisole in TFA (0.1 mL) was then added to the residue. After 5 min at room temperature, [$^{125}$I]8 was isolated by HPLC (Econosil C18 10μ., 250×4.6 mm, $H_2O/CH_3CN$/TFA [85/15/0.1], 1 mL/min). Reverse phase radio-HPLC purification of [$^{125}$I]8 was performed using a Waters 510 pump, Waters 490E variable wavelength UV/Vis detector at 354 nm and a Bioscan Flow Count PMT radioactivity detector (Washington D.C.). The yields of this reaction were 59-75% (three separate determinations). Specific radioactivity was >2,000 Ci/mmol (74.0 GBq/μmol) in each case.

Example 11

Synthesis of 2-(3-{1-carboxy-5-[2-(4-fluoro-benzylideneaminooxy)-acetylamino]-pentyl}-ureido)-pentanedioic acid (9)

To a solution of compound 1 (0.062 g, 0.073 mmol) in $CH_2Cl_2$ (2 mL) was added triethylamine (0.045 mL, 0.320 mmol), followed by N-tert-butyloxycarbonyl-O-(carboxymethyl)hydroxyamine hydroxysuccinimidyl ester (0.025 g, 0.087 mmol, Bioconjugate Chemistry 1993, 4, 515-20). After stirring for 30 min at room temperature, the solvent was evaporated. The crude material was purified by a silica column using methanol/methylene chloride (5:95) to afford 0.055 g (89%) of compound 10. $^1$H NMR (400 MHz, $CDCl_3$) δ7.98 (bs, 1H), 7.91 (s, 1H), 7.25-7.27 (m, 6H), 6.85-6.88 (m, 6H), 5.56-5.63 (m, 2H), 5.01-5.11 (m, 6H), 4.47-4.53 (m, 1H), 4.27-4.38 (m, 3H), 3.79 (m, 9H), 3.30-3.38 (m, 1H), 3.15-3.21 (m, 1H), 2.36-2.41 (m, 2H), 2.10-2.15 (m, 1H), 1.89-1.95 (m, 1H), 1.74-1.81 (m, 1H), 1.23-1.61 (m, 14H). ESI-Mass calcd for $C_{43}H_{57}N_4O_{14}$ $[M+H]^+$ 853.4. found 853.5.

A solution of 3% anisole in TFA (1 mL) was added to compound 10 (0.031 g, 0.036 mmol). The mixture was stirred at room temperature for 5 min, then concentrated on a rotary evaporator. The crude material was purified by HPLC (Econosil C18 10μ, 250×10 mm, $H_2O/CH_3CN$/TFA (90/10/0.1), 4 mL/min) to afford 0.009 g (49%) of compound 11. $^1$H NMR (400 MHz, $D_2O$) δ4.68 (s, 2H), 4.28-4.35 (m, 2H), 3.34 (m, 2H), 2.58 (m, 2H), 2.24 (m, 1H), 1.78-2.13 (m, 3H), 1.62 (m, 2H), 1.49 (m, 2H). ESI-Mass calcd for $C_{14}H_{25}N_4O_9$ $[M]^+$ 393.2, found 393.3.

To a solution of compound 11 (0.005 g, 0.010 mmol) in methanol (0.3 mL) was added triethylamine (0.0075 ml, 0.05 mmol), followed by 4-fluorobenzaldehyde (0.0017 ml, 0.016 mmol). After 30 min at room temperature, the reaction mixture was purified by HPLC (Econosil C18 10μ, 250×10 mm, $H_2O/CH_3CN$/TFA (75/25/0.1) and compound 9 (0.002 g, 41%) was obtained. $^1$H NMR (400 MHz, $D_2O$:$CD_3CN$=1:1) δ 8.26 (s, 1H), 7.56-7.80 (m, 2H), 7.10-7.14 (m, 2H), 4.53 (s, 2H), 4.13-4.17 (m, 1H), 3.96-4.00 (m, 1H), 3.16 (m, 2H), 2.37 (m, 2H), 2.10-2.16 (m, 1H), 1.80-1.88 (m, 2H), 1.65 (m, 1H), 1.54 (m, 1H), 1.42 (m, 1H), 1.28 (m, 1H). ESI-Mass calcd for $C_{21}H_{27}F_4O_9Na$ $[M+Na]^+$ 521.2. found 521.3. FAB-HRMS calcd for $C_{21}H_{28}FN_4O_9$ $[M+H]^+$ 499.1840. found 499.1869.

Example 12

Synthesis of 2-(3-{1-carboxy-5-[2-(4-[$^{18}$F]fluoro-benzylideneaminooxy)-acetylamino]-pentyl}-ureido)-pentanedioic acid ([$^{18}$F]9)

4-[$^{18}$F]fluorobenzaldehyde was synthesized by using literature procedure (Nuclear Medicine and Biology 19 (1992)

275-281) and purified by HPLC ($H_2O/CH_3CN$/TFA 70/30/0.1). The HPLC eluent of 4-[$^{18}$F]fluorobenzaldehyde was diluted with $H_2O$, passed through a C18 Sep Pak, eluted with 2 mL of methanol. To a solution of compound 11 (1 mg) in methanol (0.05 mL) was added [$^{18}$F]4-fluorobenzaldehyde in 2 mL methanol. After stirred 30 min at room temperature, the reaction mixture was purified by HPLC to give compound [$^{18}$F]9. The radiochemical yield (decay corrected and based on starting [$^{18}$F]fluoride, n=2) was 6-9%. The specific activity of final compound was found to be 350-1300 mCi/μmol.

Example 13

Synthesis of 2-[3-(1-carboxy-5-{4-[N'-(4-fluorobenzylidene)-hydrazino]-benzoylamino}-pentyl)-ureido]-pentanedioic acid (12)

To a solution of compound 1 (0.030 g, 0.035 mmol) in $CH_2Cl_2$ (2 mL) was added triethylamine (0.020 mL, 0.142 mmol), followed by succinimidyl 4-[2-(tert-butoxycarbonyl)hydrazino benzoate (0.020 g, 0.057 mmol, Bioconjugate Chem. 1991, 2, 333-336) in DMF (0.2 mL). After stirred for 1 hour at room temperature, the solvent was evaporated. The crude material was purified by a silica column using methanol/methylene chloride (5:95) to afford 0.025 g (78%) of compound 13. $^1$H NMR (400 MHz, $CDCl_3$) δ7.63 (d, J=8.0 Hz, 2H), 7.19-7.23 (m, 6H), 6.81-6.85 (m, 6H), 6.68 (d, J=8.8 Hz, 2H), 6.61 (s, 2H), 6.15 (bs, 1H) 5.68 (m, 2H), 4.95-5.07 (m, 6H), 4.34-4.45 (m, 2H), 3.74 (m, 9H), 3.25 (m, 2H), 2.31 (m, 2H), 2.10 (m, 1H), 1.84 (m, 1H), 1.19-1.74 (m, 14H). ESI-Mass calcd for $C_{48}H_{59}N_5O_{13}Na$ $[M+Na]^+$ 936.4. found 935.9.

A solution of TFA/$CH_2Cl_2$ 1:1 (2 mL) was added to compound 13 (0.025 g, 0.027 mmol). The mixture was stirred at room temperature for 1 hour, then concentrated on a rotary evaporator. The crude material was purified by HPLC (Econosphere C18 10μ, 250×10 mm, $H_2O/CH_3CN$/TFA (92/8/0.1), 4 mL/min) to afford 0.010 g (64%) of compound 14. $^1$H NMR (400 MHz, $D_2O$) δ7.72 (d, J=8.8 Hz, 2H), 7.02 (d, J=8.8 Hz, 2H), 4.15-4.23 (m, 2H), 3.35 (m, 2H), 2.46 (m, 2H), 2.10-2.17 (m, 1H), 1.80-1.95 (m, 2H), 1.59-1.74 (m, 3H), 1.45 (m, 2H). ESI-Mass calcd for $C_{19}H_{28}N_5O_8$ $[M+H]^+$ 454.2. found 453.9.

To a solution of compound 14 (0.004 g, 0.009 mmol) in water (0.030 mL) was added 0.1 mL of 50 mM $KH_2PO_4$, followed by 4-fluorobenzaldehyde (0.0011 g, 0.009 mmol) in 0.05 mL acetonitrile. The reaction mixture was heated at 90° C. for 10 min, then purified by HPLC (Econosphere C18 10μ, 250×10 mm, $H_2O/CH_3CN$/TFA (65/35/0.1) and compound 12 (0.003 g, 76%) was obtained. $^1$H NMR (400 MHz, $D_2O$:$CD_3CN$=3:2) δ7.82 (s, 1H), 7.64 (m, 4H), 7.11 (m, 4H), 4.14 (m, 2H), 3.24 (m, 2H), 2.01 (m, 2H), 1.94 (m, 1H), 1.80 (m, 2H), 1.52-1.63 (m, 3H), 1.35 (m, 2H). ESI-Mass calcd for $C_{26}H_{31}FN_5O_8$ $[M+H]^+$ 560.2. found 560.1.

Example 14

Synthesis of 2-[3-(1-carboxy-5-{4-[N'-(4-[$^{18}$F]fluoro-benzylidene)-hydrazino]-benzoylamino}-pentyl)-ureido]-pentanedioic acid ([$^{18}$F]12)

4-[$^{18}$F]fluorobenzaldehyde was synthesized by using a known procedure (Nuclear Medicine and Biology 33 (2006) 677-683). To the crude DMSO solution of 4-[$^{18}$F]fluorobenzaldehyde was added 1-2 mg of compound 14, 0.2 mL of 50 mM $KH_2PO_4$. The vial was closed and heated at 90° C. for 15 min. The reaction mixture was then purified by HPLC (Econosphere C18 10μ, 250×10 mm, $H_2O/CH_3CN$/TFA [70/30/0.1], 4 mL/min). The radiochemical yield (decay corrected and based on starting [$^{18}$F] fluoride, n=2) was 30-55%. The compound 12 decomposed soon after been made. The specific activity of final compound was not determined.

Example 15

Synthesis of 2-{3-[1-carboxy-5-({6-[N'-(4-fluorobenzylidene)-hydrazino]-pyridine-3-carbonyl}-amino)-pentyl]ureido}-pentanedioic acid (15)

To a solution of compound 1 (0.040 g, 0.047 mmol) in $CH_2Cl_2$ (2 mL) was added triethylamine (0.020 mL, 0.14 mmol), followed by succinimidyl 6-(N'-tert-butoxycarbonyl-hydrazino)-nicotinate (0.020 g, 0.057 mmol, Bioconjugate Chem. 1991, 2, 333-336). After stirred for 1 hour at room temperature, the solvent was evaporated. The crude material was purified by a silica column using methanol/methylene chloride (10:90) to afford 0.032 g (74%) of compound 16. $^1$H NMR (400 MHz, $CDCl_3$) δ8.54 (s, 1H), 7.90 (m, 1H), 7.17-7.23 (m, 6H), 6.90-7.05 (m, 3H), 6.79-6.84 (m, 6H), 6.55 (d, J=8.8 Hz, 2H), 5.79 (m, 2H), 4.94-5.07 (m, 6H), 4.38-4.45 (m, 2H), 3.74 (m, 9H), 3.26 (m, 2H), 2.33 (m, 2H), 2.07 (m, 1H), 1.85 (m, 1H), 1.68 (m, 1H), 1.18-1.55 (m, 13H). ESI-Mass calcd for $C_{47}H_{59}N_6O_{13}$ $[M+H]^+$ 915.4. found 914.9.

A solution of TFA/$CH_2Cl_2$ 1:1 (2 mL) was added to compound 16 (0.032 g, 0.035 mmol). The mixture was stirred at room temperature for 1 hour, then concentrated on a rotary evaporator. The crude material was purified by HPLC (Econosphere C 18 10μ, 250×10 mm, $H_2O/CH_3CN$/TFA (92/8/0.1), 4 mL/min) to afford 0.009 g (45%) of compound 17. $^1$H NMR (400 MHz, $D_2O$) δ8.07-8.40 (m, 2H), 7.00-7.13 (m, 1H), 4.18-4.24 (m, 2H), 3.38 (m, 2H), 2.48 (m, 2H), 2.14 (m, 1H), 1.86-1.98 (m, 2H), 1.62-1.65 (m, 3H), 1.44 (m, 2H). ESI-Mass calcd for $C_{18}H_{27}N_6O_8$ $[M+H]^+$ 455.2. found 455.0.

To a solution of compound 17 (0.005 g, 0.0011 mmol) in water (0.030 mL) was added 50 mM $KH_2PO_4$ 0.1 mL, followed by 4-fluorobenzaldehyde (0.002 g, 0.0016 mmol) in 0.05 mL acetonitrile. The reaction mixture was heated at 90° C. for 10 min, then purified by HPLC (Econosphere C18 10μ, 250×10 mm, $H_2O/CH_3CN$/TFA (80/20/0.1) and compound 15 (0.002 g, 41%) was obtained. $^1$H NMR (400 MHz, $D_2O$) δ8.38 (m, 1H), 8.22 (m, 2H), 7.83 (m, 2H), 7.20 (m, 3H), 4.26 (m, 2H), 3.41 (m, 2H), 2.52 (m, 2H), 2.11 (m, 1H), 1.92 (m, 2H), 1.73 (m, 3H), 1.47 (m, 2H). ESI-Mass calcd for $C_{25}H_{30}FN_6O_8$ $[M+H]^+$ 561.2. found 560.9.

Example 16

Synthesis of 2-{3-[1-carboxy-5-({6-[Nα-(4-[$^{18}$F]fluoro-benzylidene)-hydrazino]-pyridine-3-carbonyl}-amino)-pentyl]-ureido}-pentanedioic acid ([$^{18}$F]15)

4-[$^{18}$F]fluorobenzaldehyde was synthesized by using a known procedure (Nuclear Medicine and Biology 33 (2006) 677-683). To the crude DMSO solution of 4-[$^{18}$F]fluorobenzaldehyde was added 1-2 mg of compound 16, 0.2 mL of 50 mM $KH_2PO_4$. The vial was closed and heated at 90° C. for 15 min. The reaction mixture was then purified by HPLC (Econosphere C18 10μ, 250×10 mm, $H_2O/CH_3CN$/TFA [80/20/0.1], 4 mL/min). The radiochemical yield (decay corrected and based on starting [$^{18}$F]fluoride, n=1) was 49%.

Example 17

In Vitro Binding

NAALADase Assay.

NAAG hydrolysis was performed essentially as described previously (26)(27) Briefly, LNCaP cell extracts were prepared by sonication in NAALADase buffer (50 mM Tris [pH 7.4] and 0.5% Triton X-100). Cell lysates were incubated with or without inhibitor at 37° C. for 10 min. Following the incubation the radiolabeled substrate N-acetyl-L-aspartyl-L-(3,4-$^3$H)glutamate (NEN Life Science Products, Boston, Mass.) was added to a final concentration of 30 nM at 37° C. for 10-15 min. The reaction was stopped by the addition of an equal volume of ice-cold 100 mM sodium phosphate and 2 mM EDTA. Products were partitioned by AG 1-X8 formate resin (Bio-Rad Laboratories, Hercules, Calif.) anion exchange chromatography, eluted with 1 M sodium formate, and quantified by liquid scintillation counting. Inhibition curves were determined using semi-log plots and $IC_{50}$ values determined at the concentration at which enzyme activity was inhibited by 50%. Assays were performed in triplicate with the entire inhibition study being repeated at least once to confirm affinity and mode of inhibition. Data were collected during the linear phase of hydrolysis (i.e., <20% cleavage of total substrate). Enzyme inhibitory constants ($K_i$ values) were generated using the Cheng-Prusoff conversion (28). Data analysis was performed using GraphPad Prism version 4.00 for Windows (GraphPad Software, San Diego, Calif.).

PSMA activity was also determined using a fluorescence-based assay according to a previously reported procedure (29). Briefly, lysates of LNCaP cell extracts were incubated with inhibitor in the presence of 4 μM NAAG. The amount of reduced glutamate was measured by incubating with a working solution of the Amplex Red glutamic acid kit (Molecular Probes Inc., Eugene, Oreg., USA). The fluorescence was determined by reading with a VICTOR3V multilabel plate reader (Perkin Elmer Inc., Waltham, Mass., USA) with excitation at 490 nm and emission at 642 nm.

The NAALADase inhibition assay was undertaken to determine the $K_i$ value for 3, 6 and 8 (26). The concentration of each compound was varied from 0.01 nM to 1000 nM against a fixed amount of [$^3$H]NAAG (30 nM). The NAALADase (PSMA) was prepared from LNCaP cell lysates. The percentage of the enzymatic cleavage product, [$^3$H]glutamate, produced was measured by scintillation counting and was plotted against the logarithmic concentration of the compound under study. Linear regression of the resulting data were solved for 50% [$^3$H]glutamate production (50% inhibition) and resulted in $K_i$ values of 0.010 nM for 3, 0.256 nM for 6 and 0.351 nM for 8 (Table 1). That result is in keeping with other compounds of this class (30). When these compounds were evaluated through a fluorescence-based inhibition assay as a second check on affinity, $K_i$ values of 3, 6, and 8 were 0.010, 0.194, and 0.557 nM, respectively.

TABLE 1

PSMA in vitro Inhibitory Activities and Calculated ClogD values

| compd | $K_i$ [nM][a] | SD[b] | $K_i$ [nM][c] | SD[b] | ClogD |
|---|---|---|---|---|---|
| 3 | 0.010 | 0.003 | 0.010 | 0.004 | −5.16 |
| 6 | 0.256 | 0.038 | 0.194 | 0.134 | −5.64 |
| 8 | 0.351 | 0.257 | 0.557 | 0.265 | −5.88 |

[a]obtained from the NAALADase (radiometric) assay.
[b]95% confidence interval.
[c]obtained from a fluorescence-based assay.

Example 18

Modeling of Inhibitors in the Active Site of PSMA

Protein Preparation.

The 3-D coordinates of GCPII for docking studies were prepared as GCPII crystal structures in complex with 2-PMPA (PDB ID: 2PVW) or compound 3 (PDB ID:3D7H) through a clean-up process implemented in Discovery Studio 2.0 (DS 2.0), which can correct for structural disorder, fix bond order and connectivity of amino acid residues. The CHARMm forcefield that was applied to the protein and the binding site for docking studies was obtained through an automated method by using the option of finding sites from receptor cavities. Two zinc ions and one chloride ion in the active site were typed as $Zn^{2+}$ and $Cl^-$, with formal charges of +2 and −1, respectively.

Docking Studies with CDOCKER.

Docking studies of compounds 3, 6 and 8 were performed with two conformers of 2PVW using the CDOCKER module implemented in DS 2.0 by modifying the default settings (Top hits: 20, random conformations: 20, random conformation dynamics steps: 1000, random conformations dynamics target temperature: 1000, orientation to refine: 20, maximum bad orientations: 800, orientation vdW energy threshold: 300, simulation heating steps: 2000, heating target temperature: 700, cooling steps: 5000, cooling target temperature: 300, Grid extension: 8, ligand partial charge: CHARMm). The best pose of each ligand with high CDOCKER energy was used for generating the overlay structures (FIGS. 1 and 2) with crystal ligand 3 (shown in lighter color) from GCPII complex (PDB ID: 3D7H). Seven water molecules within 3 Å from crystal ligand 3 were included for docking studies with 3D7H.

Figure 2:
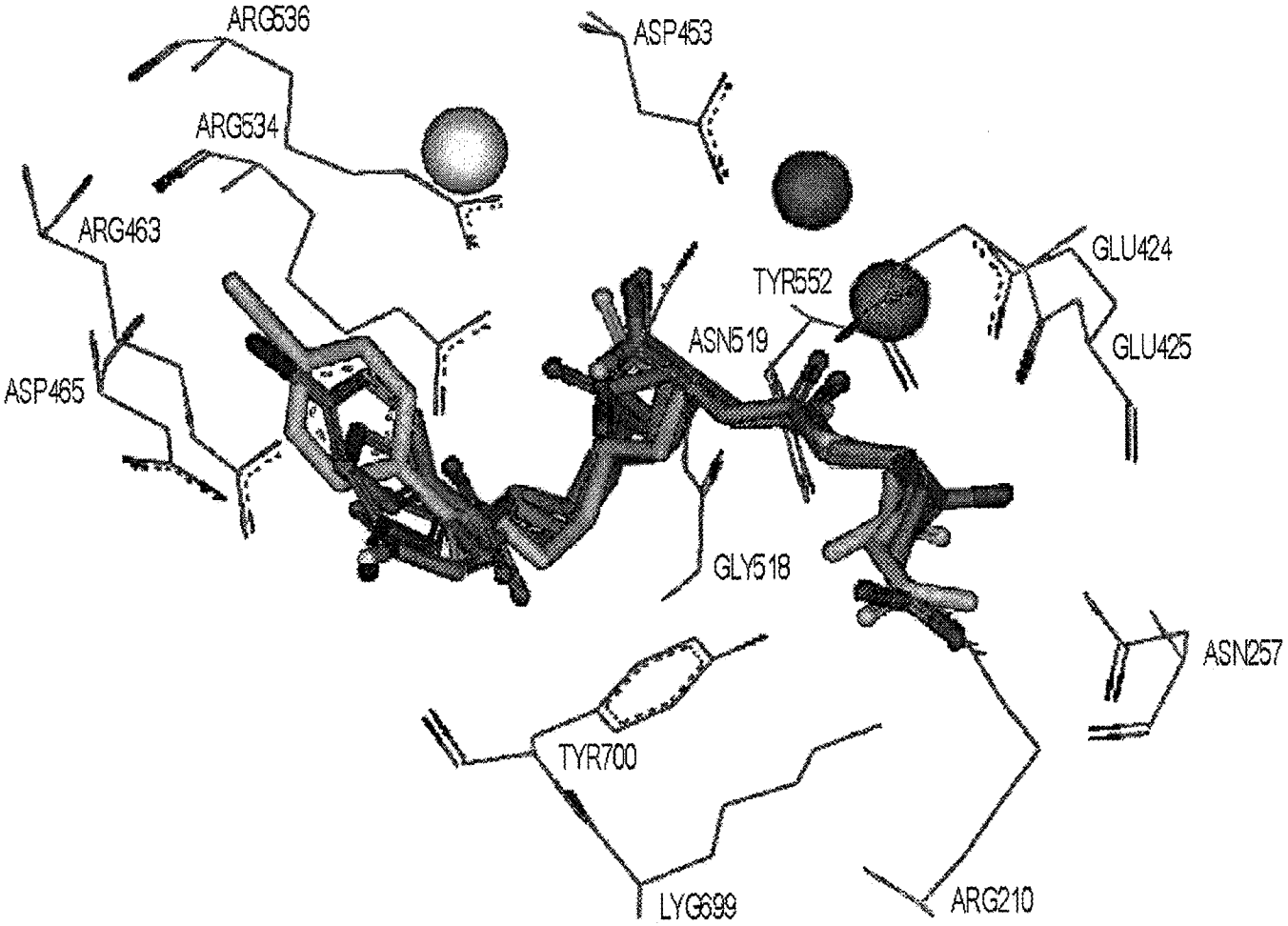
FIG. 2 shows an overlay of the best poses (3, 6 and 8) with the crystal ligand (3) in the absence of water molecule in the active site of PSMA. Dark sphere (zinc ions), light sphere (chloride ion).

The PSMA crystal structure complexed with 3, which was deposited in the protein data bank (PDB ID: 3D7H) was resolved. Details of PSMA co-crystallized with 3 as well as with other urea-based PSMA inhibitors such as DCIT, DCMC and DCFBC, are described by Barinka et al. (39). As predicted from modeling studies, only the binding conformation of the arginine patch region was found in the PSMA complex with 3. To elucidate potential binding modes of the other two compounds (6 and 8), docking studies using the 3-D coordinates of 3D7H in the presence or in the absence of water molecules in the active site were carried out. The best poses of 3, 6 and 8 from the docking studies using the CDOCKER module are shown in FIG. 1, overlaid with crystal ligand, i.e., the compound as it is co-crystallized with PSMA, of 3. As shown in FIG. 1, all of the radionuclide-bearing moieties (4-iodophenyl, 4-fluorophenyl, and 5-iodo-3-pyridyl) were located within the arginine patch of the S1 binding site. 4-Iodophenyl and 4-fluorophenyl groups protruded deeply within the subpocket compared to the 5-iodo-3-pyridyl moiety. CDOCKER scores of the three poses are ordered 3 (80.63)>6 (72.39)>8 (69.78). Aromatic rings of 3, 6, and 8 provide π-π interactions with the guanidine functions of Arg 463 and Arg 534, leading to stabilization of the ligand within the subpocket. In the case of 8, the nitrogen of the pyridine ring enables electrostatic interaction with the carboxylate of Asp 465 and hydrogen bonding with one water molecule. Docking results of PSMA without water molecules in the active site showed that the radionuclide-bearing moieties of 6 and 8 were outside of the subpocket and projected into the tunnel region (FIG. 2) while the 4-iodophenyl group of 3 was projected into the subpocket. Based on in vitro PSMA inhibitory activities and molecular modeling studies, it appears that ligand interaction with the subpocket of the S1 binding site contributes more to binding affinity than interaction with the tunnel region.

Figure 5:
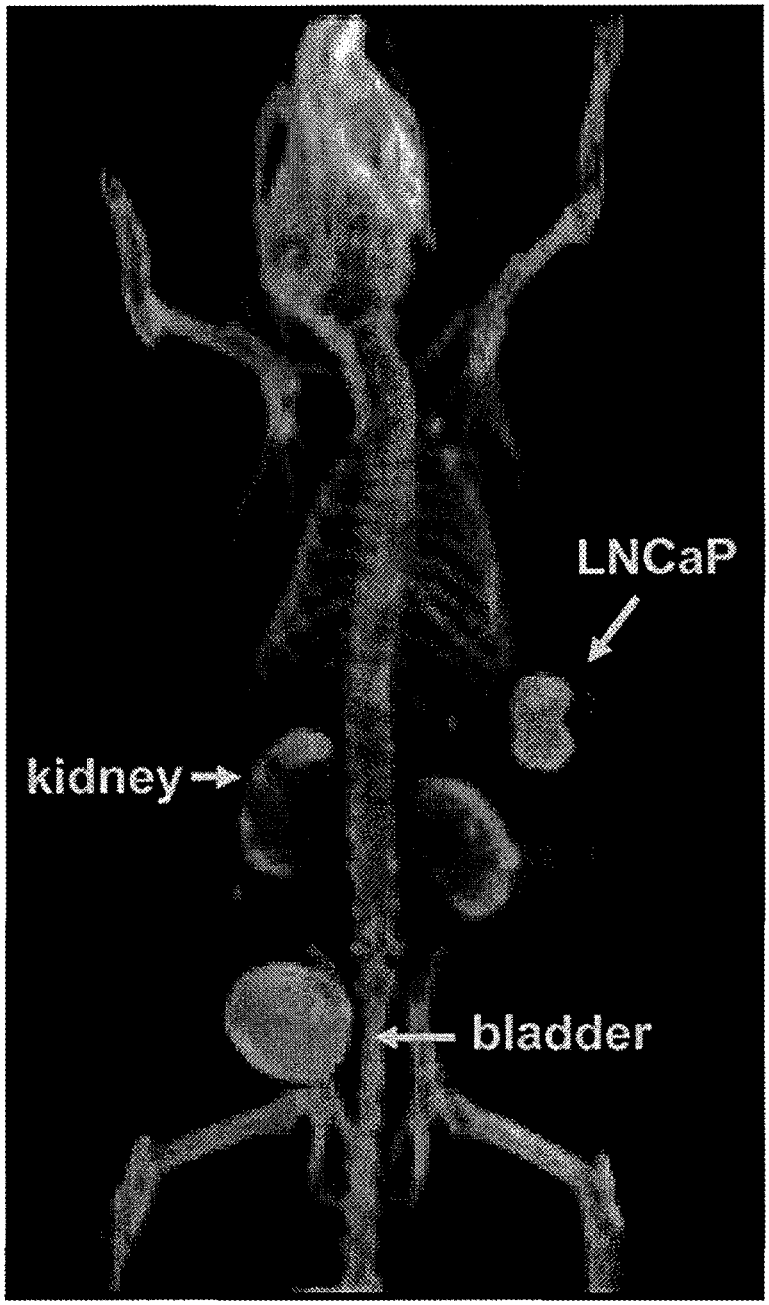
FIG. 5 shows [$^{125}$I]8 SPECT-CT in PSMA+ LNCaP tumors (4 h postinjection). Note intense uptake within tumor. A similar result was obtained for PSMA+ PIP but not PSMA-flu tumors (data not shown). There is less renal and liver uptake with this agent than the halobenzoylated analogues, [$^{125}$I]3 and [$^{18}$F]6, respectively.

Not surprisingly, 3, 6 and 8 assume similar conformations within the PSMA active site. The radionuclide-bearing moiety resides within the arginine patch region of the S1' binding site in each case, however, that of 8 is not as deep within the pocket (FIG. 1). Compound 3 has been co-crystallized with PSMA, and the binding conformation for that compound shows productive π-π stacking with Arg 463 and Arg 534 of the enzyme, whereas the pyridine moiety of 8 is unable to form a similarly productive π-π interaction. However, unlike 3 or 6, 8 is able to interact with Asp 465 (via the pyridine nitrogen), with Asp 453 (via the carbonyl oxygen) and a water molecule because the carbonyl group of the radionuclide-bearing moiety points toward the Si subpocket. Those additional interactions likely offset the less productive π-π bonding geometry of 8, providing a high-affinity interaction and an imaging agent that gives clear delineation of tumor (FIG. 5). While 6 adopts a very similar conformation within the active site as 3, it binds with significantly lower affinity, likely due to additional interactions of the iodine within the positively-charged arginine patch for 3. In all, the affinities of 3, 6 and 8 (Table 1) track with predications based on molecular modeling.

Biodistribution and Imaging

Cell Lines and Mouse Models:

PC-3 PIP ($PSMA^+$) and PC-3 flu ($PSMA^-$) cell lines were obtained from Dr. Warren Heston (Cleveland Clinic) and were maintained as previously described (19). All cells were grown to 80-90% confluence before trypsinization and formulation in Hank's Balanced Salt Solution (HBSS, Sigma, St. Louis, Mo.) for implantation into mice.

All animal studies were carried out in full compliance with institutional guidelines related to the conduct of animal experiments. Male severe-combined immunodeficient (SCID) mice (Charles River Laboratories, Wilmington, Mass.) were implanted subcutaneously with $1\text{-}5\times10^6$ cells forward of each shoulder. PC-3 PIP cells were implanted behind the left shoulder and PC-3 flu cells were implanted behind the right shoulder. Mice were imaged or used in biodistribution assays when the tumor xenografts reached 3-5 mm in diameter.

Ex Vivo Biodistribution and Imaging

Example 19

Compound [$^{125}$I]3

Xenograft-bearing SCID mice were injected via the tail vein with 74 Bq (2 μCi) of [$^{125}$I]3. Four mice each were sacrificed by cervical dislocation at 30, 60, 120, 300 min, 12, 24 and 48 hours p.i. The heart, lungs, liver, stomach, pancreas, spleen, fat, kidney, muscle, small and large intestines, urinary bladder and PIP and flu tumors were quickly removed. A 0.1 mL sample of blood was also collected. The organs were weighed and the tissue radioactivity measured with an automated gamma counter (1282 Compugamma CS, Pharmacia/LKB Nuclear, Inc, Gaithersburg, Md.). The percent-injected dose per gram of tissue (% ID/g) was calculated by comparison with samples of a standard dilution of the initial dose. All measurements were corrected for decay.

Table 2 outlines the ex vivo rodent tissue distribution results of [$^{125}$I]3. The blood, kidney, urinary bladder, spleen and $PSMA^+$ PC-3 PIP tumor display high uptake at the initial, 30 min postinjection (p.i.) time point. By 60 min p.i., the urinary bladder displays the highest uptake while the uptake in $PSMA^+$ PC-3 PIP tumor also achieves its highest absolute value. The kidney achieves its maximal uptake at 24 h p.i. The values noted in the kidney are largely due to specific binding rather than renal clearance, due to the expression of high amounts of PSMA in the proximal renal tubule (31)(32). Urinary bladder uptake represents excretion at all time points, i.e., there was no specific binding to bladder wall. Tumor uptake demonstrates a high degree of specificity represented by the PIP:flu ratio of 10:1 at 60 min and rising to 140:1 at 48 h. Radiopharmaceutical uptake within tumor relative to other organs also increases with time. Site-specific blockade studies were not performed as they were perceived to be redundant in light of the use of engineered (PC-3 PIP and PC-3 flu) tumors to determine binding specificity.

TABLE 2

Ex vivo biodistribution of [$^{125}$I]3 in tumor-bearing mice.[a,b]

| Organ | 30 min | 60 min | 2 h | 5 h | 12 h | 24 h | 48 h |
|---|---|---|---|---|---|---|---|
| blood | 0.9 ± 0.8 (10) | 0.6 ± 0.2 (22) | 0.3 ± 0.1 (36) | 0.4 ± 0.2 (31) | 0.1 ± 0.03 (125) | ND | ND |
| heart | 2.7 ± 0.9 (3) | 1.9 ± 0.3 (7) | 1.4 ± 0.7 (8) | 0.9 ± 0.2 (14) | 0.5 ± 0.2 (25) | 0.5 ± 0.2 (28) | 0.1 ± 0.1 (100) |
| lung | 5.8 ± 2.4 (1.5) | 4.5 ± 0.5 (3) | 3.6 ± 2.8 (3) | 3.5 ± 0.6 (3.5) | 2.6 ± 0.8 (5) | 1.1 ± 0.8 (12) | 0.5 ± 0.04 (22) |
| liver | 7.7 ± 3.1 (1) | 7.5 ± 0.8 (2) | 5.9 ± 3.5 (2) | 4.5 ± 1.0 (3) | 1.4 ± 0.2 (9) | 1.4 ± 0.6 (9) | 0.7 ± 0.1 (16) |
| stomach | 1.5 ± 0.9 (6) | 1.5 ± 0.3 (9) | 1.6 ± 1.5 (8) | 0.8 ± 0.03 (15) | 0.3 ± 0.06 (39) | 0.7 ± 0.6 (18) | 0.4 ± 0.2 (25) |
| pancreas | 2.0 ± 0.3 (4) | 2.3 ± 0.3 (6) | 2.0 ± 0.7 (6) | 1.6 ± 0.5 (8) | 0.6 ± 0.2 (21) | 1.2 ± 0.7 (11) | 1.1 ± 0.6 (10) |
| spleen | 83 ± 8 (0.1) | 141 ± 14 (0.1) | 104 ± 43 (0.1) | 119 ± 9 (0.1) | 69 ± 39 (0.2) | 39 ± 6 (0.3) | 22 ± 8.6 (0.5) |
| fat | 4.5 ± 1.1 (2) | 5.6 ± 1.0 (2) | 6.2 ± 0.8 (2) | 6.8 ± 1.3 (2) | 3.8 ± 0.8 (3) | 1.6 ± 1.9 (8) | 2.8 ± 0.7 (4) |

TABLE 2-continued

Ex vivo biodistribution of [$^{125}$I]3 in tumor-bearing mice.[a,b]

| Organ | 30 min | 60 min | 2 h | 5 h | 12 h | 24 h | 48 h |
|---|---|---|---|---|---|---|---|
| kidney | 119 ± 15 (0.1) | 121 ± 17 (0.1) | 111 ± 34 (0.1) | 132 ± 12 (0.1) | 169 ± 29 (0.1) | 234 ± 140 (0.1) | 101 ± 30 (0.1) |
| muscle | 2.7 ± 2.4 (3) | 0.8 ± 0.2 (17) | 0.6 ± 0.2 (21) | 0.4 ± 0.1 (31) | 1.0 ± 0.1 (12.5) | 0.4 ± 0.1 (33) | 0.25 ± 0.03 (44) |
| small int. | 4.9 ± 1.9 (2) | 3.8 ± 0.4 (3.5) | 1.5 ± 0.3 (8) | 1.5 ± 0.2 (8) | 1.0 ± 0.4 (12.5) | 0.25 ± 0.1 (54) | 0.1 ± 0.1 (110) |
| large int. | 1.4 ± 0.6 (6) | 1.0 ± 0.2 (13.5) | 0.6 ± 0.1 (21) | 0.7 ± 0.6 (17) | 0.6 ± 0.2 (21) | 1.6 ± 1.9 (9) | 0.15 ± 0.1 (73) |
| bladder | 5.2 ± 1.7 (2) | 6.1 ± 0.8 (2) | 4.0 ± 2.6 (3) | 3.0 ± 1.7 (4) | 0.8 ± 0.3 (16) | 0.2 ± 0.2 (64) | 0.3 ± 0.04 (37) |
| PC-3 PIP | 8.8 ± 4.7 | 13.5 ± 2.1 | 11.8 ± 5.6 | 12.4 ± 6.4 | 12.5 ± 4.8 | 13.4 ± 5.1 | 11.0 ± 0.2 |
| PC-3 flu | 1.8 ± 1.0 | 1.2 ± 0.3 | 0.7 ± 0.3 | 0.6 ± 0.05 | 0.3 ± 0.1 | 0.1 ± 0.06 | 0.08 ± 0.06 |
| PIP:flu | 5 | 11 | 18 | 19 | 48 | 131 | 140 |

[a]Values are in % ID/g ± SD; ND = not determined; n = 4 except at 48 h where n = 3. Int. = intestine.
[b]Pip tumor:organ ratios are in parentheses

Example 20

Compound [$^{18}$F]6

Ex vivo biodistribution proceeded as for [$^{125}$I]3 with the following exceptions: Mice were injected with 3.7 MBq (100 μCi) of [$^{18}$F]6 and uptake times were 30, 60, 120 and 300 minutes p.i.

Table 3 illustrates tissue uptake of [$^{18}$F]6. This radiopharmaceutical also displayed rapid, specific uptake within PSMA$^+$ PIP tumors (8.58±3.09% ID/g at 30 min. p.i.) and kidney (72.05±3.19% ID/g at 30 min. p.i.). Uptake in and washout from nonspecific tissues was low and fast, respectively. Only the liver and spleen display uptake values that rival those seen in PIP tumor. The spleen exhibits the highest uptake of any nonspecific tissue (12.67±0.36% ID/g at 30 min. p.i.), perhaps due to the presence of GCPIII, a close homolog of GCPII/PSMA (33). It is speculated that [$^{18}$F]6 may bind to GCPIII as well as to GCPII, as several other PSMA ligands have been shown to do so (34).

TABLE 3

Ex vivo biodistribution of [$^{18}$F]6 in tumor-bearing mice.[a,b]

| Organ | 30 min | 60 min | 2 h | 5 h |
|---|---|---|---|---|
| blood | 2.5 ± 1.7 (3) | 0.7 ± 0.5 (9) | 0.4 ± 0.2 (9) | 0.03 ± 0.00 (117) |
| heart | 0.8 ± 0.1 (11) | 0.2 ± 0.02 (35) | 0.15 ± 0.05 (25) | 0.03 ± 0.01 (117) |
| lung | 1.7 ± 0.3 (5) | 0.5 ± 0.1 (13) | 1.0 ± 0.9 (4) | 0.1 ± 0.1 (35) |
| liver | 8.7 ± 1.8 (1) | 5.8 ± 0.6 (1) | 11.7 ± 7.0 (0.3) | 1.0 ± 0.6 (3.5) |
| stomach | 0.8 ± 0.1 (11) | 0.25 ± 0.1 (26) | 0.3 ± 0.1 (13) | 0.04 ± 0.02 (88) |
| pancreas | 0.8±0.1 (11) | 0.3 ± 0.1 (21) | 0.15 ± 0.03 (25) | 0.05 ± 0.03 (70) |
| spleen | 12.7 ± 0.4 (0.7) | 7.2 ± 1.6 (1) | 4.4 ± 1.2 (1) | 1.0 ± 0.6 (3.5) |
| kidney | 72 ± 3 (0.1) | 48 ± 5 (0.1) | 29 ± 12 (0.1) | 14 ± 9 (0.3) |
| muscle | 2.4 ± 3.1 (4) | 0.5 ± 0.7 (13) | 0.2 ± 0.1 (19) | 0.1 ± 0.1 (35) |
| small int. | 1.7 ± 0.7 (5) | 0.6 ± 0.2 (11) | 0.3 ± 0.2 (12) | 0.1 ± 0.04 (35) |
| large int. | 1.2 ± 0.8 (7) | 0.5 ± 0.1 (13) | 0.2 ± 0.1 (19) | 0.6 ± 0.6 (6) |
| bladder | 6.8 ± 3.5 (1) | 17 ± 21 (0.4) | 11 ± 8 (0.3) | 5.2 ± 8.9 (0.7) |
| PC-3 PIP | 8.6 ± 3.1 | 6.4 ± 0.9 | 3.7 ± 1.2 | 3.5 ± 2.3 |

TABLE 3-continued

Ex vivo biodistribution of [$^{18}$F]6 in tumor-bearing mice.[a,b]

| Organ | 30 min | 60 min | 2 h | 5 h |
|---|---|---|---|---|
| PC-3 flu | 0.8 ± 0.3 | 0.3 ± 0.05 | 0.25 ± 0.1 | 0.1 ± 0.1 |
| PIP:flu | 11 | 21 | 15 | 35 |

[a]Values are in % ID/g ± SD, n = 4, int. = intestine.
[b]Pip tumor:organ ratios are in parentheses.

Example 21

Compound [$^{125}$I]8

PC-3 PIP and PC-3 flu xenograft-bearing SCID mice were injected via the tail vein with 74 KBq (2 μCi) of [$^{125}$I]8. Four mice each were sacrificed by cervical dislocation at 30, 60, 240 min., 8 and 24 hours p.i. The heart, lungs, liver, stomach, pancreas, spleen, fat, kidney, muscle, small and large intestines, urinary bladder and PIP and flu tumors were quickly removed. A 0.1 mL sample of blood was also collected. All the organs were weighed and the tissue radioactivity measured with an automated gamma counter (1282 Compugamma CS, Pharmacia/LKB Nuclear, Inc, Gaithersburg, Md.). The % ID/g was calculated by comparison with samples of a standard dilution of the initial dose. All measurements were corrected for decay.

Table 4 outlines the ex vivo rodent tissue distribution results of [$^{125}$I]8. The liver, spleen, kidney and PSMA$^+$ PC-3 PIP tumor displayed high uptake at the initial, 30 min p.i. time point. By 60 min p.i., the kidney displayed the highest uptake while that in PSMA$^+$ PC-3 PIP tumor remained steady, showing a similar value to that at 30 min. By 24 h, there was complete clearance of radioactivity from the individual, nontarget organs. The values noted in the kidney are largely due to specific binding rather than renal clearance, as for the other radiopharmaceuticals discussed above. Urinary bladder uptake represented excretion at all time points, i.e., there was no specific binding to bladder wall, while tumor uptake demonstrated a high degree of specificity represented by the PIP:flu uptake ratio of 18:1 at 30 min, rising to 48:1 at 24 h. As for [$^{125}$I]3, the radiopharmaceutical uptake within tumor relative to other organs increases with time.

TABLE 4

Ex vivo biodistribution of [$^{125}$I]8 in tumor-bearing mice.[a,b]

| Organ | 30 min | 60 min | 4 h | 8 h | 24 h |
|---|---|---|---|---|---|
| blood | 2.5 ± 1.4 (6) | 1.1 ± 0.5 (11) | 0.25 ± 0.2 (17) | 0.06 ± 0.01 (23) | 0.00 ± 0.00 |
| heart | 0.9 ± 0.2 (16) | 0.4 ± 0.3 (30) | 0.06 ± 0.02 (20) | 0.02 ± 0.01 (70) | 0.00 ± 0.00 |
| lung | 2.7 ± 3.2 (5) | 2.3 ± 1.0 (5) | 0.3 ± 0.1 (14) | 0.1 ± 0.05 (12) | 0.01 ± 0.00 (9) |
| liver | 8.2 ± 1.2 (2) | 9.7 ± 1.2 (1) | 4.8 ± 0.9 (1) | 1.6 ± 0.4 (1) | 0.04 ± 0.03 (2) |
| stomach | 0.8 ± 0.3 (18) | 0.5 ± 0.3 (23) | 0.1 ± 0.05 (42) | 0.06 ± 0.02 (23) | 0.01 ± 0.01 (9) |
| pancreas | 0.9 ± 0.2 (15) | 0.8 ± 0.3 (16) | 0.3 ± 0.3 (14) | 0.03 ± 0.00 (47) | 0.00 ± 0.00 |
| spleen | 26 ± 12 (0.5) | 13.0 ± 6.8 (1) | 1.25 ± 0.4 (3) | 0.5 ± 0.2 (3) | 0.03 ± 0.02 (3) |
| fat | 3.5 ± 0.2 (4) | 1.4 ± 0.5 (8) | 0.04 ± 0.1 (105) | 0.2 ± 0.2 (7) | 0.00 ± 0.01 |
| kidney | 160 ± 27 (0.1) | 205 ± 46 (0.06) | 71 ± 27 (0.06) | 24 ± 10 (0.06) | 0.97 ± 0.94 (0.1) |
| muscle | 1.9 ± 2.4 (7) | 0.9 ± 0.7 (13) | 0.2 ± 0.3 (21) | 0.1 ± 0.1 (14) | 0.00 ± 0.00 |
| small int. | 0.8 ± 0.2 (18) | 1.1 ± 1.3 (11) | 0.2 ± 0.05 (21) | 0.1 ± 0.02 (14) | 0.01 ± 0.01 (9) |
| Large int. | 0.9 ± 0.4 (16) | 0.6 ± 0.3 (21) | 0.2 ± 0.1 (21) | 0.1 ± 0.1 (14) | 0.00 ± 0.00 |
| bladder | 1.9 ± 0.4 (8) | 4.8 ± 4.9 (2.5) | 7.0 ± 3.6 (0.6) | 2.8 ± 2.1 (0.5) | 0.05 ± 0.01 (2) |
| PC-3 PIP | 14.2 ± 9.5 | 12.1 ± 4.9 | 4.2 ± 1.5 | 1.4 ± 0.4 | 0.09 ± 0.04 |
| PC-3 flu | 0.8 ± 0.1 | 0.6 ± 0.25 | 0.1 ± 0.02 | 0.03 ± 0.01 | 0.00 ± 0.00 |
| PIP:flu | 18 | 20 | 42 | 47 | |

[a]Values are in % ID/g ± SD; n = 4; int. = intestine.
[b]Pip tumor:organ ratios are in parentheses.

Figure 3:
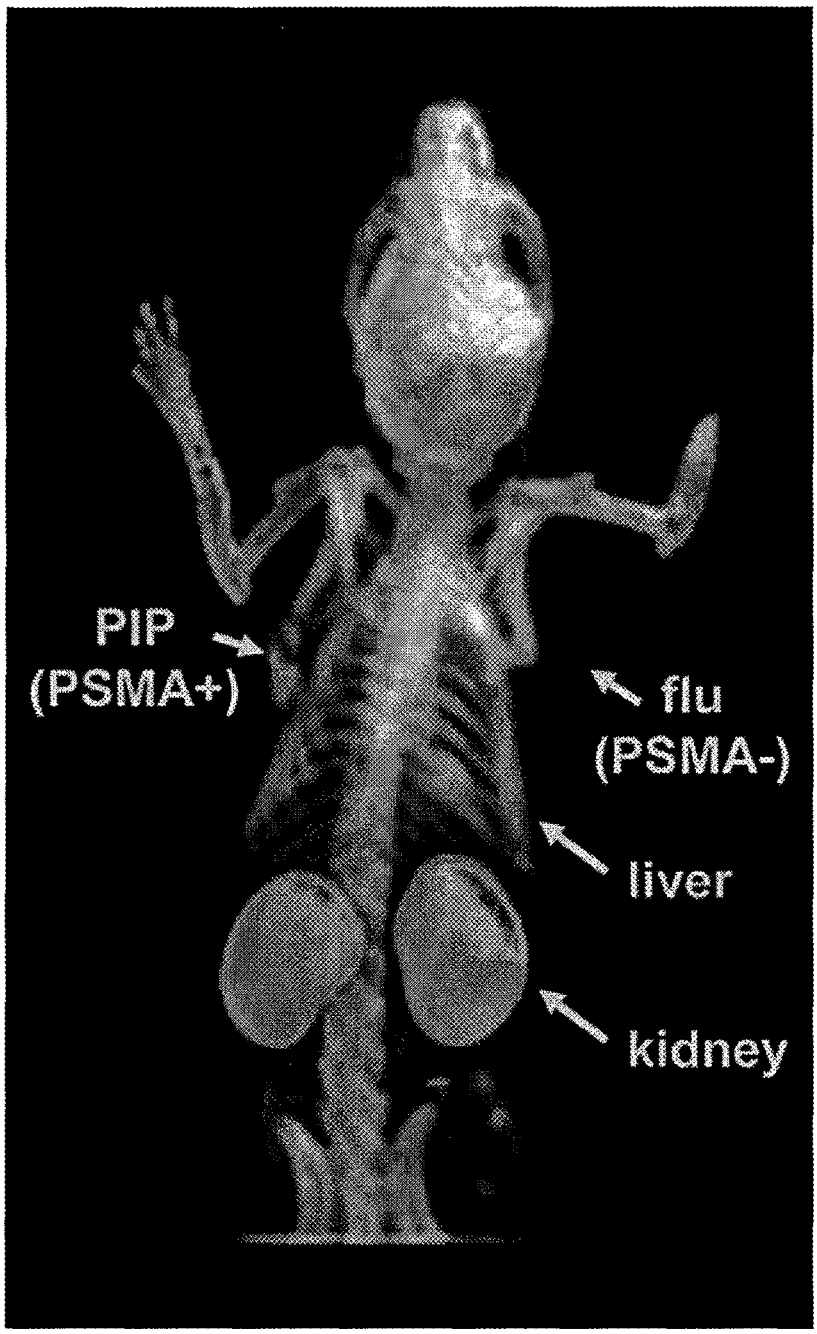
FIG. 3 shows [$^{125}$I]3 SPECT-CT in PCa tumor models (4 h postinjection). Note uptake within the PSMA+ PIP tumor only. Uptake within kidneys is due in large measure to the specific binding of [$^{125}$I]3 to renal cortex.
Figure 4:
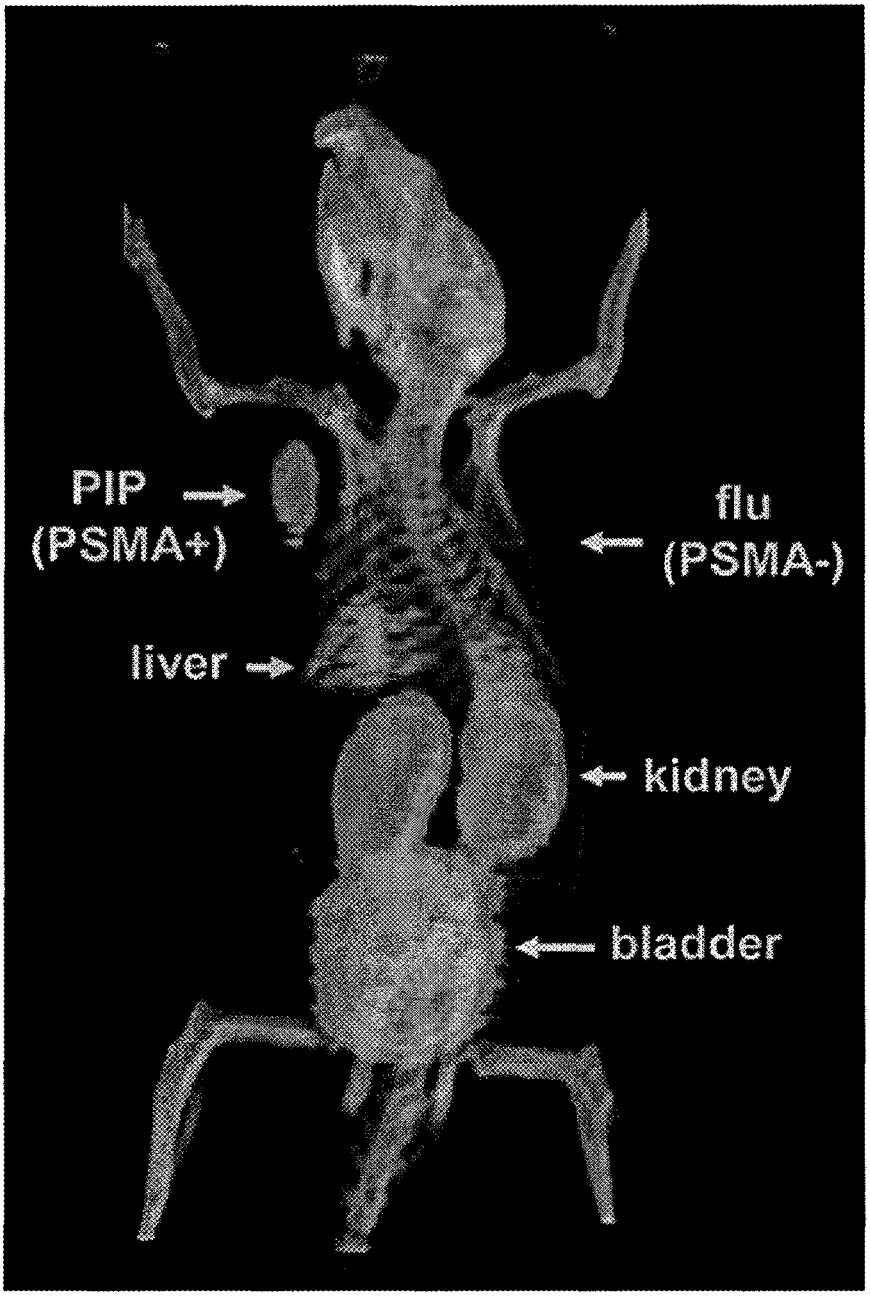
FIG. 4 shows [$^{18}$F]6 PET coregistered to CT in PCa tumor models (~100 min postinjection). Note uptake within the PSMA+ PIP tumor only. Uptake within kidneys is due in large measure to the specific binding of [$^{125}$I]3 to renal cortex. There is more intense tumor uptake and less liver seen with this agent than with [$^{125}$I]3.

Regarding ex vivo biodistribution, 3 demonstrates only about twice the tumor uptake at 1 h p.i. as 6, while its affinity is about twenty-five times higher. The target to nontarget (PIP:flu) ratio for 6, however, is higher than for 3, reflecting lower nonspecific binding. Those target to nontarget ratios rise to approximately 140 at 48 hours p.i. for 3 and to 31 at 5 hours p.i. for 6. Compound 8 differs from 3 in that the aromatic ring is a pyridine and the iodine is substituted at the three-position. At one hour p.i. 8 demonstrated a similarly high tumor uptake (12.05±4.92% ID/g) compared to 3, but had a much higher target to nontarget (PIP:flu) ratio at that time (22), which rose to 48.3 at 24 h p.i. Interestingly, the affinity of 8 is the lowest among the three compounds tested (Table 1), however, it provides the highest target to nontarget ratio at 1 h p.i. As demonstrated in previous work with $^{99m}$Tc-labeled compounds of this series, it is again shown that there is not a clear relationship between affinity and in vivo tumor uptake selectivity. Notably, all of these affinities are quite high and the tumors are clearly delineated (FIGS. 3-5).

In Vivo Biodistribution and Imaging

Example 22

Compound [$^{125}$I]3

A single SCID mouse implanted with both a PC-3 PIP and a PC-3 flu xenograft was injected intravenously with 37 MBq (1 mCi) of [$^{125}$I]3 in saline. At 4 and 6 h p.i. the mouse was anesthetized with isoflurane and maintained under 1% isoflurane in oxygen. The mouse was positioned on the X-SPECT (Gamma Medica, Northridge, Calif.) gantry and was scanned using two low energy, high-resolution pinhole collimators (Gamma Medica) rotating through 360° in 6° increments for 45 seconds per increment. All gamma images were reconstructed using Lunagem software (Gamma Medica, Northridge, Calif.). Immediately following SPECT acquisition, the mice were then scanned by CT (X-SPECT) over a 4.6 cm field-of-view using a 600 μA, 50 kV beam. The SPECT and CT data were then coregistered using the supplier's software (Gamma Medica, Northridge, Calif.) and displayed using AMIDE (http://amide.sourceforge.net/). Data were reconstructed using the Ordered Subsets-Expectation Maximization (OS-EM) algorithm.

FIG. 3 shows a SPECT-CT image of radiopharmaceutical uptake at 4 h p.i. Note the intense uptake in the PC-3 PIP and absence of uptake in the PC-3 flu tumor. Thyroid uptake of the radiotracer indicates the presence of free [$^{125}$I]iodide due to deiodination by dehalogenases (35)(36). The amount of free [$^{125}$I]iodide, however, is small in comparison to the amount of PC-3 PIP tumor uptake (thyroid:muscle=2; PIP tumor:thyroid=12.5). The small amount of radiopharmaceutical uptake seen in the liver, with no concurrent gastrointestinal uptake, is likely due to the hydrophilic nature of [$^{125}$I]3 (ClogD=−5.16 at pH 7.4).

Example 23

Compound [$^{18}$F]6

In vivo PET-CT: A SCID mouse bearing subcutaneous PC-3 PIP and PC-3 flu xenografts was anesthetized using 3% isoflurane in oxygen for induction and 1.5% isoflurane in oxygen at 0.8 L/min flow for maintenance and positioned prone on the gantry of a GE eXplore Vista small animal PET scanner (GE Healthcare, Milwaukee, Wis.). The mouse was injected intravenously with 7.4 MBq (200 μCi) of [$^{18}$F]6 followed by image acquisition using the following protocol: The images were acquired as a pseudodynamic scan, i.e., a sequence of successive whole-body images acquired in three bed positions for a total of 90 min. The dwell time at each position was 5 minutes, such that a given bed position (or mouse organ) was revisited every 15 min. An energy window of 250-700 keV was used. Images were reconstructed using the FORE/2D-OSEM method (2 iterations, 16 subsets) and included corrections for radioactive decay, scanner dead time and scattered radiation.

FIG. 4 shows the averaged results of the dynamic scan from 94-120 min p.i. The uptake pattern for [$^{18}$F]6 is very similar to that seen for [$^{125}$I]3: easily observed within PIP tumor, none within flu tumor, high renal uptake and a modest degree of liver uptake. That result was expected due to similar ClogD values for [$^{18}$F]6 (−5.64 at pH 7.4) and [$^{125}$I]3. As for [$^{125}$I]3, the urinary bladder is visualized due to the continually accumulating presence of radioactive urine, however, specific binding to bladder wall was not demonstrated.

Example 24

Compound [$^{125}$I]8

A single SCID mouse implanted with a LNCaP xenograft was injected intravenously with 37 MBq (1 mCi) of [$^{125}$I]8 in saline. At 4 h p.i., the mouse was anesthetized with isoflurane and maintained under 1% isoflurane in oxygen. The mouse was positioned on the X-SPECT (Gamma Medica, Northridge, Calif.) gantry and was scanned using two low energy, high-resolution pinhole collimators (Gamma Medica) rotating through 360° in 6° increments for 45 seconds per increment. All gamma images were reconstructed using Lunagem software (Gamma Medica, Northridge, Calif.). Immediately following SPECT acquisition, the mice were then scanned by CT (X-SPECT) over a 4.6 cm field-of-view using a 600 μA, 50 kV beam. The SPECT and CT data were then coregistered using the supplier's software (Gamma Medica, Northridge, Calif.) and displayed using AMIDE (http://amide.sourceforge.net/). Data were reconstructed using the Ordered Subsets-Expectation Maximization (OS-EM) algorithm.

FIG. 5 shows a SPECT-CT image of radiopharmaceutical uptake at 4 h p.i. Tumor uptake and retention was high, with slow washout, while the washout of [$^{125}$I]8 from nontarget tissue was rapid.

Comparative Data for Target/Nontarget Ratios for Phenyl Versus Pyridine Analogs.

Target/non-target ratios are given for compound 3 (4-iodobenzoyl derivative) at 5 hours post injection and compound 8 (3-iodo-5-carboxyl-pyridyl derivative) at 4 hour post-injection. The target/non-target ratios are shown in Table 5 below.

TABLE 5

| Tumor (T)/organ | Cmpd. 3 (5 hours post injection) | Cmpd. 8 (4 hours post injection) |
|---|---|---|
| T/blood | 31 | 17 |
| T/heart | 14 | 20 |
| T/Lung | 3.5 | 14 |
| T/liver | 3 | 1 |
| T/stomach | 15 | 42 |
| T/Pancreas | 8 | 14 |
| T/Spleen | 0.1 | 3 |
| T/fat | 2 | 105 |

TABLE 5-continued

| Tumor (T)/organ | Cmpd. 3 (5 hours post injection) | Cmpd. 8 (4 hours post injection) |
|---|---|---|
| T/kidney | 0.1 | 0.1 |
| T/muscle | 31 | 21 |
| T/small Intest | 8 | 21 |
| T/large Intest | 17 | 21 |

It appears that the improved target/non-target ratios for 8 versus 3 is due to the faster non-target clearance of 8 even though the blood clearance of each are comparable and 3 has higher tumor retention especially at later time points. Compound 3 is more lipophilic than 8 and has higher uptake in fat. The retention of 3 in fat could be providing a slow release of 3 for uptake in tumor and normal organs.

The high and prolonged tumor and kidney (PSMA rich in mice) uptake of 3 is due to this compounds tight binding to PSMA. The 4-iodophenyl moiety resides in a hydrophobic pocket accessory to the Si binding site and provides additional hydrophobic-hydrophobic interactions (39). Pyridine analogs are more polar than 3 so they should have reduced hydrophobic-hydrophobic interactions in this binding site.

Compound 6 has even better target/non-target ratios than compound 8. Therefore the background clearance of the more polar pyridine analog of 6 should give even better tumor-non-target ratios.

REFERENCES

1. Jemal, A., Murray, T., Samuels, A., Ghafoor, A., Ward, E., and Thun, M. J. (2003) Cancer statistics, 2003. CA Cancer J Clin 53, 5-26.
2. Geus-Oei, L. F., and Oyen, W. J. (2008) Predictive and prognostic value of FDG-PET. Cancer Imaging 8, 70-80
3. Larson, S. M., Morris, M., Gunther, I., Beattie, B., Humm, J. L., Akhurst, T. A., Finn, R. D., Erdi, Y., Pentlow, K., Dyke, J., Squire, O., Bornmann, W., McCarthy, T., Welch, M., and Scher, H. (2004) Tumor localization of 16beta-18F-fluoro-5alpha-dihydrotestosterone versus 18F-FDG in patients with progressive, metastatic prostate cancer. J Nucl Med 45, 366-373
4. Scher, B., Seitz, M., Albinger, W., Tiling, R., Scherr, M., Becker, H. C., Souvatzogluou, M., Gildehaus, F. J., Wester, H. J., and Dresel, S. (2007) Value of 11C-choline PET and PET/CT in patients with suspected prostate cancer. Eur J Nucl Med Mol Imaging 34, 45-53
5. Reske, S. N., Blumstein, N. M., Neumaier, B., Gottfried, H. W., Finsterbusch, F., Kocot, D., Moller, P., Glatting, G., and Perner, S. (2006) Imaging prostate cancer with 11C-choline PET/CT. J Nucl Med 47, 1249-1254
6. Vees, H., Buchegger, F., Albrecht, S., Khan, H., Husarik, D., Zaidi, H., Soloviev, D., Hany, T. F., and Miralbell, R. (2007) 18F-choline and/or 11C-acetate positron emission tomography: detection of residual or progressive subclinical disease at very low prostate-specific antigen values (<1 ng/mL) after radical prostatectomy. BJU Int 99, 1415-1420
7. Ponde, D. E., Dence, C. S., Oyama, N., Kim, J., Tai, Y. C., Laforest, R., Siegel, B. A., and Welch, M. J. (2007) 18F-fluoroacetate: a potential acetate analog for prostate tumor imaging—in vivo evaluation of 18F-fluoroacetate versus 11C-acetate. J Nucl Med 48, 420-428
8. Schuster, D. M., Votaw, J. R., Nieh, P. T., Yu, W., Nye, J. A., Master, V., Bowman, F. D., Issa, M. M., and Goodman, M. M. (2007) Initial experience with the radiotracer anti-1-amino-3-18F-fluorocyclobutane-1-carboxylic acid with PET/CT in prostate carcinoma. J Nucl Med 48, 56-63

9. Oka, S., Hattori, R., Kurosaki, F., Toyama, M., Williams, L. A., Yu, W., Votaw, J. R., Yoshida, Y., Goodman, M. M., and Ito, O. (2007) A preliminary study of anti-1-amino-3-18F-fluorocyclobutyl-1-carboxylic acid for the detection of prostate cancer. J Nucl Med 48, 46-55
10. Tehrani, O. S., Muzik, O., Heilbrun, L. K., Douglas, K. A., Lawhorn-Crews, J. M., Sun, H., Mangner, T. J., and Shields, A. F. (2007) Tumor imaging using 1-(2'-deoxy-2'-18F-fluoro-beta-D-arabinofuranosyl)thymine and PET. J Nucl Med 48, 1436-1441
11. Chang, S. S., Reuter, V. E., Heston, W. D., Bander, N. H., Grauer, L. S., and Gaudin, P. B. (1999) Five different anti-prostate-specific membrane antigen (PSMA) antibodies confirm PSMA expression in tumor-associated neovasculature. Cancer Res 59, 3192-3198.
12. Zhou, J., Neale, J. H., Pomper, M. G., and Kozikowski, A. P. (2005) NAAG peptidase inhibitors and their potential for diagnosis and therapy. Nat Rev Drug Discov 4, 1015-1026
13. Chang, S. S. (2004) Overview of prostate-specific membrane antigen. Rev Urol 6 Suppl 10, S13-18
14. Murphy, G. P., Kenny, G. M., Ragde, H., Wolfert, R. L., Boynton, A. L., Holmes, E. H., Misrock, S. L., Bartsch, G., Klocker, H., Pointner, J., Reissigl, A., McLeod, D. G., Douglas, T., Morgan, T., and Gilbaugh, J., Jr. (1998) Measurement of serum prostate-specific membrane antigen, a new prognostic marker for prostate cancer. Urology 51, 89-97.
15. Galsky, M. D., Eisenberger, M., Moore-Cooper, S., Kelly, W. K., Slovin, S. F., DeLaCruz, A., Lee, Y., Webb, I. J., and Scher, H. I. (2008) Phase I trial of the prostate-specific membrane antigen-directed immunoconjugate MLN2704 in patients with progressive metastatic castration-resistant prostate cancer. J Clin Oncol 26, 2147-2154
16. Lange, P. H. (2001) PROSTASCINT scan for staging prostate cancer. Urology 57, 402-406.
17. Haseman, M. K., Rosenthal, S. A., and Polascik, T. J. (2000) Capromab Pendetide imaging of prostate cancer. Cancer Biother Radiopharm 15, 131-140.
18. Rosenthal, S. A., Haseman, M. K., and Polascik, T. J. (2001) Utility of capromab pendetide (ProstaScint) imaging in the management of prostate cancer. Tech Urol 7, 27-37.
19. Banerjee, S. R., Foss, C. A., Mease, R. C., Fox, J., Kozikowski, A. P., and Pomper, M. G. (2008) Synthesis and evaluation of 99 mTc/Re labeled PSMA inhibitors. J Med Chem 51, 4504-4517.
20. Vaidyanathan, G., and Zalutsky, M. R. (1994) Improved synthesis of N-succinimidyl 4-[18F]fluorobenzoate and its application to the labeling of a monoclonal antibody fragment. Bioconjug Chem 5, 352-356
21. Vaidyanathan, G., and Zalutsky, M. R. (2006) Synthesis of N-succinimidyl 4-[18F]fluorobenzoate, an agent for labeling proteins and peptides with 18F. Nature protocols 1, 1655-1661
22. Vaidyanathan, G., and Zalutsky, M. R. (1992) Labeling proteins with fluorine-18 using N-succinimidyl-4-[18F] fluorobenzoate. Int J Rad Appl Instrum Part B 19, 275-281
23. Chen, X., Park, R., Shahinian, A. H., Tohme, M., Khankaldyyan, V., Bozorgzadeh, M. H., Bading, J. R., Moats, R., Laug, W. E., and Conti, P. S. (2004) 18F-labeled RGD peptide: initial evaluation for imaging brain tumor angiogenesis. Nucl Med Biol 31, 179-189
24. Dekker, B., Keen, H., Shaw, D., Disley, L., Hastings, D., Hadfield, J., Reader, A., Allan, D., Julyan, P., Watson, A., and Zweit, J. (2005) Functional comparison of annexin V analogues labeled indirectly and directly with iodine-124. Nucl Med Biol 32, 403-413
25. Garg, S., Garg, P. K., and Zalutsky, M. R. (1991) N-succinimidyl 5-(trialkylstannyl)-3-pyridinecarboxylates: a new class of reagents for protein radioiodination. Bioconjug Chem 2, 50-56
26. Lupold, S. E., Hicke, B. J., Lin, Y., and Coffey, D. S. (2002) Identification and characterization of nuclease-stabilized RNA molecules that bind human prostate cancer cells via the prostate-specific membrane antigen. Cancer Res 62, 4029-4033
27. Robinson, M. B., Blakely, R. D., Couto, R., and Coyle, J. T. (1987) Hydrolysis of the brain dipeptide N-acetyl-L-aspartyl-L-glutamate. Identification and characterization of a novel N-acetylated alpha-linked acidic dipeptidase activity from rat brain. J Biol Chem 262, 14498-14506
28. Cheng, H. C. (2001) determination of KB or Ki from IC50. A closer look at the Cheng-Prusoff equation, the Schild plot and related power equations. J. Pharmacol. Toxicol. Methods 46, 61-71
29. Kozikowski, A. P., Nan, F., Conti, P., Zhang, J., Ramadan, E., Bzdega, T., Wroblewska, B., Neale, J. H., Pshenichkin, S., and Wroblewski, J. T. (2001) Design of remarkably simple, yet potent urea-based inhibitors of glutamate carboxypeptidase II (NAALADase). J Med Chem 44, 298-301.
30. Kozikowski, A. P., Zhang, J., Nan, F., Petukhov, P. A., Grajkowska, E., Wroblewski, J. T., Yamamoto, T., Bzdega, T., Wroblewska, B., and Neale, J. H. (2004) Synthesis of urea-based inhibitors as active site probes of glutamate carboxypeptidase II: efficacy as analgesic agents. J Med Chem 47, 1729-1738
31. Slusher, B. S., Tsai, G., Yoo, G., and Coyle, J. T. (1992) Immunocytochemical localization of the N-acetyl-aspartyl-glutamate (NAAG) hydrolyzing enzyme N-acetylated alpha-linked acidic dipeptidase (NAALADase). J Comp Neurol 315, 217-229
32. Silver, D. A., Pellicer, I., Fair, W. R., Heston, W. D., and Cordon-Cardo, C. (1997) Prostate-specific membrane antigen expression in normal and malignant human tissues. Clin Cancer Res 3, 81-85
33. Bzdega, T., Crowe, S. L., Ramadan, E. R., Sciarretta, K. H., Olszewski, R. T., Ojeifo, O. A., Rafalski, V. A., Wroblewska, B., and Neale, J. H. (2004) The cloning and characterization of a second brain enzyme with NAAG peptidase activity. J Neurochem 89, 627-635
34. Hlouchova, K., Barinka, C., Klusak, V., Sacha, P., Mlcochova, P., Majer, P., Rulisek, L., and Konvalinka, J. (2007) Biochemical characterization of human glutamate carboxypeptidase III. J Neurochem 101, 682-696
35. Bakker, W. H., Krenning, E. P., Breeman, W. A., Koper, J. W., Kooij, P. P., Reubi, J. C., Klijn, J. G., Visser, T. J., Docter, R., and Lamberts, S. W. (1990) Receptor scintigraphy with a radioiodinated somatostatin analogue: radiolabeling, purification, biologic activity, and in vivo application in animals. J Nucl Med 31, 1501-1509
36. Bakker, W. H., Krenning, E. P., Breeman, W. A., Kooij, P. P., Reubi, J. C., Koper, J. W., de Jong, M., Lameris, J. S., Visser, T. J., and Lamberts, S. W. (1991) In vivo use of a radioiodinated somatostatin analogue: dynamics, metabolism, and binding to somatostatin receptor-positive tumors in man. J Nucl Med 32, 1184-1189.

37. Garg, S., Garg, P. K., Zhao, X-G., Friedman, H. S., Bigner, D. D., and Zalutsky, M. R., Radioiodination of a monoclonal antibody using N-succinimidyl 5-iodo-3-pyridinecarboxylate Nucl. Med. Biol. 20: 835-842 (1993);

38. Ghirmai, S., Mume, E., Tolmachev, V., and Sjoberg, S., Synthesis and radioiodination of some daunorubicin and doxorubicin derivatives Carbohydrate Research 340 15-24 (2005).

39. Barinka, C., Byun, Y., Dusich, C. L., Banerjee, S. R., Chen, Y., Castanares, M., Kozikowski, A. P., Mease, R. C., Pomper, Martin G., and Lubkowski, J., Interactions between human glutamate carboxypeptidase II and urea-based inhibitors: Structural Characterizations. J. Med. Chem. 51: 7737-7743 (2008).

The invention claimed is:

1. A compound having the structure

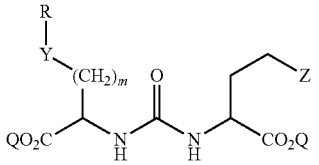

Wherein Z is tetrazole or $CO_2Q$;

each Q is independently selected from hydrogen or a protecting group; and wherein (A) m is 0, 1, 2, 3, 4, 5, or 6;

R is a pyridine ring selected from the group consisting of

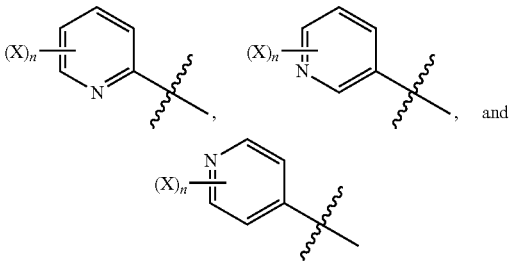

wherein X is fluorine, iodine, a radioisotope of fluorine, a radioisotope of iodine, chlorine, bromine, a radioisotope of bromine, a radioisotope of astatine, $NO_2$, $NH_2$, $N^+(R^2)_3$, $Sn(R^2)_3$, $Si(R^2)_3$, $Hg(R^2)$, $B(OH)_2$, —$NHNH_2$, —NHN═$CHR^3$, —NHNH—$CH_2R^3$;

n is 1, 2, 3, 4, or 5;

Y is O, S, N(R'), C(O), NR'C(O), C(O)N(R'), OC(O), C(O)O, NR'C(O)NR', NR'C(S)NR', $NR'S(O)_2$, $S(CH_2)_p$, $NR'(CH_2)_p$, $O(CH_2)_p$, $OC(O)CHR^8NHC(O)$, $NHC(O)CHR^8NHC(O)$, or a covalent bond; wherein p is 1, 2, or 3, R' is H or $C_1$-$C_6$ alkyl, and $R^8$ is hydrogen, alkyl, aryl or heteroaryl, each of which may be substituted;

$R^2$ is $C_1$-$C_6$ alkyl; and $R_3$ is alkyl, alkenyl, alkynyl, aryl, or heteroaryl each of which is substituted by fluorine, iodine, a radioisotope of fluorine, a radioisotope of iodine, chlorine, bromine, a radioisotope of bromine, or a radioisotope of astatine, $NO_2$, $NH_2$, $N^+(R^2)_3$, $Sn(R^2)_3$, $Si(R^2)_3$, $Hg(R^2)$, or $B(OH)_2$.

2. A compound according to claim 1, wherein Z is $CO_2Q$.

3. A compound according to claim 1, wherein Q is hydrogen.

4. A compound according to claim 1, where m is 1, 2, 3, or 4.

5. A compound according to claim 1, having the structure

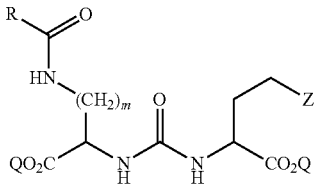

wherein m is not 0.

6. A compound according to claim 5, where Z is $CO_2Q$, Q is hydrogen, and m is 4.

7. A compound according to claim 1, having the structure

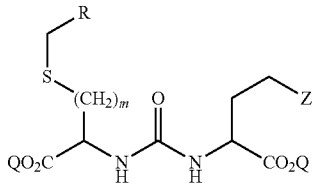

wherein m is not 0.

8. A compound according to claim 7, where Z is $CO_2Q$, Q is hydrogen, and m is 1, 2, or 3.

9. A compound according to claim 1, wherein n is 1.

10. A compound according to claim 1, wherein X or X' is fluorine, iodine, or a radioisotope of fluorine or iodine, bromine, a radioisotope of bromine, or a radioisotope of astatine.

11. A compound according to claim 1, wherein X or X' is fluorine, iodine, or a radioisotope of fluorine or iodine.

12. A compound according to claim 1, wherein R comprises a radioisotope.

13. A compound according to claim 12, wherein the radioisotope is selected from the group consisting of $^{18}F$, $^{123}I$, $^{124}I$, $^{125}I$, $^{126}I$, $^{131}I$, $^{75}Br$, $^{76}Br$, $^{77}Br$, $^{80}Br$, $^{80m}Br$, $^{82}Br$, $^{83}Br$ and $^{211}At$.

14. A method of imaging one or more cells, organs or tissues comprising exposing the cell to or administering to a organism an effective amount of a compound according to claim 12.

15. The method according to claim 14, wherein the one or more organs or tissues includes prostate tissue, kidney tissue, brain tissue vascular tissue or tumor tissue.

16. A compound according to claim 1 selected from the group consisting of

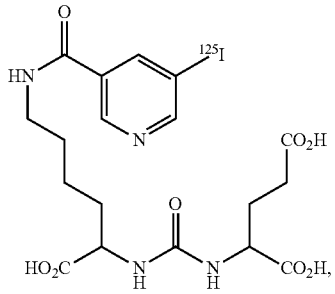

-continued

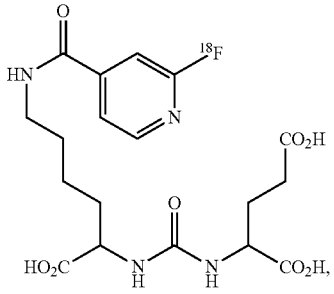

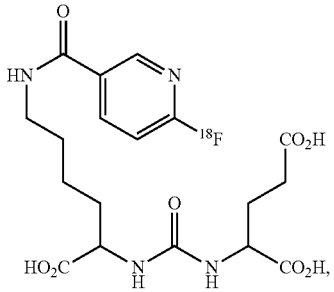

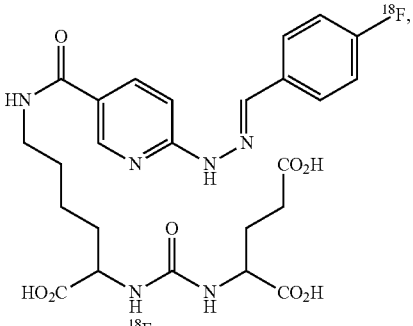

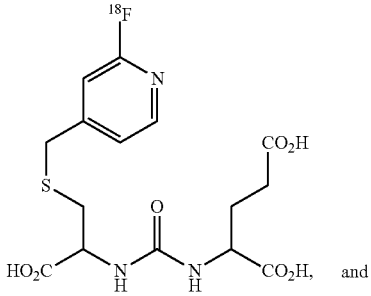

and

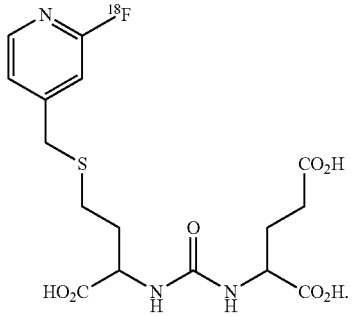

17. A method of treating a tumor comprising administering a therapeutically effective amount of a compound according to claim 1 comprising a therapeutically effective radioisotope.

18. A kit comprising a compound according to claim 1.

*19. A compound according to claim 6, wherein n is 1.*

*20. A compound according to claim 19, wherein R is a pyridine ring selected from the group consisting of*

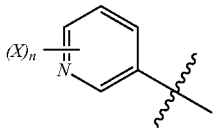

*and*

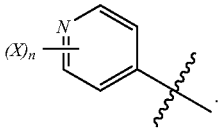

*21. A compound according to claim 20, wherein X is a radioisotope of fluorine or a radioisotope of iodine.*

*22. A compound according to claim 21, wherein X is $^{125}I$ or $^{18}F$.*

*23. A compound according to claim 22, wherein R is a pyridine ring selected from*

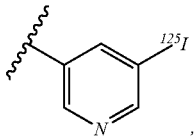

,

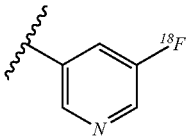

*and*

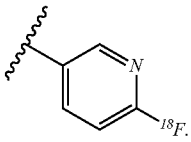

*24. A compound acording to claim 19, wherein R is*

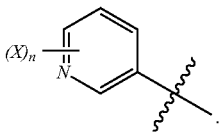

*25. A compound according to claim 24, wherein X is a radioisotope of fluorine or a radioisotope of iodine.*

*26. A compound according to claim 25, wherein X is $^{125}I$ or $^{18}F$.*

*27. A compound according to claim 26, wherein X is $^{18}F$.*

*28. A compound according to claim 27, wherein R is*

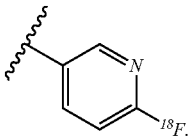

*29. A compound according to claim 16 selected from the group consisting of*

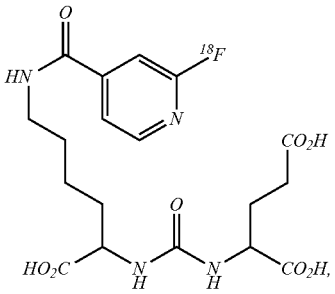
and
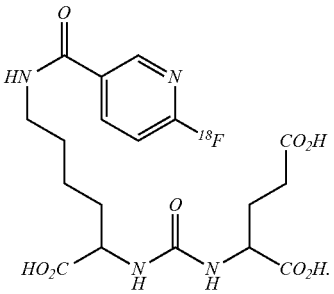
*30. A compound according to claim 29, wherein the compound has the formula*
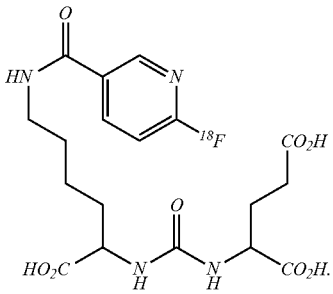
* * * * *